United States Patent
Canfield

(10) Patent No.: US 6,670,165 B2
(45) Date of Patent: Dec. 30, 2003

(54) METHODS FOR PRODUCING HIGHLY PHOSPHORYLATED LYSOSOMAL HYDROLASES

(75) Inventor: William M. Canfield, Oklahoma City, OK (US)

(73) Assignee: Genzyme Glycobiology Research Institute, Inc., Oklahoma City, OK (US)

( * ) Notice: Subject to any disclaimer, the term of this patent is extended or adjusted under 35 U.S.C. 154(b) by 0 days.

(21) Appl. No.: 09/986,552

(22) Filed: Nov. 9, 2001

(65) Prior Publication Data

US 2002/0150981 A1 Oct. 17, 2002

Related U.S. Application Data

(62) Division of application No. 09/635,872, filed on Aug. 10, 2000, now Pat. No. 6,534,300.
(60) Provisional application No. 60/153,831, filed on Sep. 14, 1999.

(51) Int. Cl.$^7$ ................................................. C12N 9/14
(52) U.S. Cl. ....................................................... 435/195
(58) Field of Search ........................................ 435/195

(56) References Cited

U.S. PATENT DOCUMENTS

| | | | |
|---|---|---|---|
| 3,957,578 A | 5/1976 | Narita et al. ................... 195/11 |
| 3,966,555 A | 6/1976 | Arnaud et al. ............. 195/66 B |
| 3,972,777 A | 8/1976 | Yamada et al. ........... 195/66 B |
| 4,140,107 A | 2/1979 | Lancee et al. ............... 128/2 V |
| 4,156,013 A | 5/1979 | Bruinvels et al. ............ 424/319 |
| 4,195,126 A | 3/1980 | Hall .............................. 435/11 |
| 4,328,215 A | 5/1982 | Bueding ........................ 424/181 |
| 4,332,894 A | 6/1982 | Whistler ......................... 435/99 |
| 4,401,662 A | 8/1983 | Lormeau et al. ............. 424/183 |
| 4,401,758 A | 8/1983 | Lormeau et al. ............. 435/84 |
| 4,431,737 A | 2/1984 | Olivieri et al. .............. 435/208 |
| 4,433,946 A | 2/1984 | Christianson et al. ......... 466/43 |
| 4,452,794 A | 6/1984 | Kort et al. .................... 424/240 |
| 4,474,770 A | 10/1984 | Lormeau et al. ............. 424/183 |
| 4,492,761 A | 1/1985 | Durack ........................ 436/519 |
| 4,496,722 A | 1/1985 | Gallop et al. ................... 545/69 |
| 4,595,015 A | 6/1986 | Jansen et al. ................ 128/713 |
| 4,615,884 A | 10/1986 | Harshman .................... 424/92 |
| 4,639,420 A | 1/1987 | Schaffner ........................ 435/2 |
| 4,659,817 A | 4/1987 | Gallop et al. ................ 540/541 |
| 4,749,570 A | 6/1988 | Poznansky .................. 424/94.3 |
| 4,798,169 A | 1/1989 | Rosen et al. ................... 119/3 |
| 4,851,390 A | 7/1989 | Morishige ..................... 514/44 |
| 4,866,042 A | 9/1989 | Neuwelt ........................ 514/44 |
| 4,975,441 A | 12/1990 | Gibson ........................ 514/328 |
| 4,981,801 A | 1/1991 | Suzuki et al. ................ 435/290 |
| 4,986,274 A | 1/1991 | Stephens ............... 128/660.18 |
| 4,987,223 A | 1/1991 | Choay et al. ................ 536/177 |
| 4,997,760 A | 3/1991 | Hirabayashi et al. ....... 435/227 |
| 5,001,072 A | 3/1991 | Olson .......................... 438/500 |
| 5,015,470 A | 5/1991 | Gibson ......................... 424/10 |
| 5,055,401 A | 10/1991 | Liljestrom et al. ........ 435/172.3 |
| 5,060,428 A | 10/1991 | Arthur, Jr. et al. ......... 52/125.6 |
| 5,061,625 A | 10/1991 | Mattes et al. ............. 435/172.3 |
| 5,075,231 A | 12/1991 | Moreau et al. .............. 435/198 |
| 5,077,200 A | 12/1991 | Habenstein .................... 435/14 |
| 5,082,778 A | 1/1992 | Overbeeke et al. ...... 435/172.3 |
| 5,089,392 A | 2/1992 | Miller et al. ................... 435/21 |
| 5,126,247 A | 6/1992 | Palmer et al. ................. 435/25 |
| 5,143,841 A | 9/1992 | Hirabayashi et al. ....... 435/222 |
| 5,166,320 A | 11/1992 | Wu et al. ..................... 530/395 |
| 5,179,023 A | 1/1993 | Calhoun et al. .......... 435/320.1 |
| 5,202,253 A | 4/1993 | Esmon et al. ........... 435/204.27 |
| 5,205,917 A | 4/1993 | Klock, Jr. ................ 204/182.8 |
| 5,208,148 A | 5/1993 | Haugland et al. .............. 435/14 |
| 5,217,865 A | 6/1993 | Myerowitz ..................... 435/6 |
| 5,242,805 A | 9/1993 | Naleway et al. .............. 435/18 |
| 5,260,447 A | 11/1993 | Nakajima et al. ........... 548/222 |
| 5,281,394 A | 1/1994 | Holub .......................... 422/65 |
| 5,296,365 A | 3/1994 | Overbeeke et al. ......... 435/208 |
| 5,310,646 A | 5/1994 | Whitley .......................... 435/4 |
| 5,316,906 A | 5/1994 | Haugland et al. ............... 435/4 |
| 5,344,352 A | 9/1994 | Horne et al. .................. 445/24 |
| 5,356,804 A | 10/1994 | Desnick et al. ............. 435/208 |
| 5,362,628 A | 11/1994 | Haugland ..................... 435/18 |
| 5,366,883 A | 11/1994 | Asada et al. ................. 435/202 |
| 5,382,524 A | 1/1995 | Desnick et al. ............. 435/200 |
| 5,401,650 A | 3/1995 | Desnick et al. ............. 435/208 |
| 5,405,751 A | 4/1995 | Roncarolo .................. 435/7.24 |
| 5,420,112 A | 5/1995 | Lewis et al. ................... 514/12 |
| 5,433,946 A | 7/1995 | Allen, Jr. et al. .......... 424/94.3 |
| 5,439,935 A | 8/1995 | Rawlings et al. ............ 514/451 |
| 5,443,986 A | 8/1995 | Haughland et al. ............. 435/4 |
| 5,449,604 A | 9/1995 | Schellenberg et al. ......... 435/6 |
| 5,466,809 A | 11/1995 | Dime .......................... 546/183 |
| 5,475,095 A | 12/1995 | Myerowitz .................. 536/23.1 |
| 5,491,075 A | 2/1996 | Desnick et al. ............. 435/69.7 |
| 5,494,810 A | 2/1996 | Barany et al. ............. 435/91.52 |
| 5,501,957 A | 3/1996 | Dennis et al. ................. 435/15 |
| 5,512,471 A | 4/1996 | Smith ......................... 435/208 |
| 5,534,615 A | 7/1996 | Baker et al. ................. 530/350 |
| 5,545,402 A | 8/1996 | Watkinson ............... 424/94.63 |
| 5,554,366 A | 9/1996 | Rawlings et al. ........ 404/78.03 |
| 5,565,362 A | 10/1996 | Rosen ..................... 435/320.1 |
| 5,569,648 A | 10/1996 | Lewis et al. ................... 514/12 |
| 5,571,675 A | 11/1996 | Baker et al. | |

(List continued on next page.)

FOREIGN PATENT DOCUMENTS

WO    99 31117    6/1999

OTHER PUBLICATIONS

Bischoff, J., et al. (1984) Biochem. Biophy. Res. Comm. 125(1), 324–331.*

(List continued on next page.)

Primary Examiner—Charles L. Patterson, Jr.
(74) Attorney, Agent, or Firm—Oblon, Spivak, McClelland, Maier & Neustadt, P.C.

(57) ABSTRACT

The present invention provides highly phosphorylated lysosomal hydrolases, methods of modifying lysosomal hydrolases with the lysosomal targeting pathway enzymes GlcNAc-phosphotransferase and/or phosphodiester α-GlcNAcase.

42 Claims, 4 Drawing Sheets

U.S. PATENT DOCUMENTS

Figure 1:
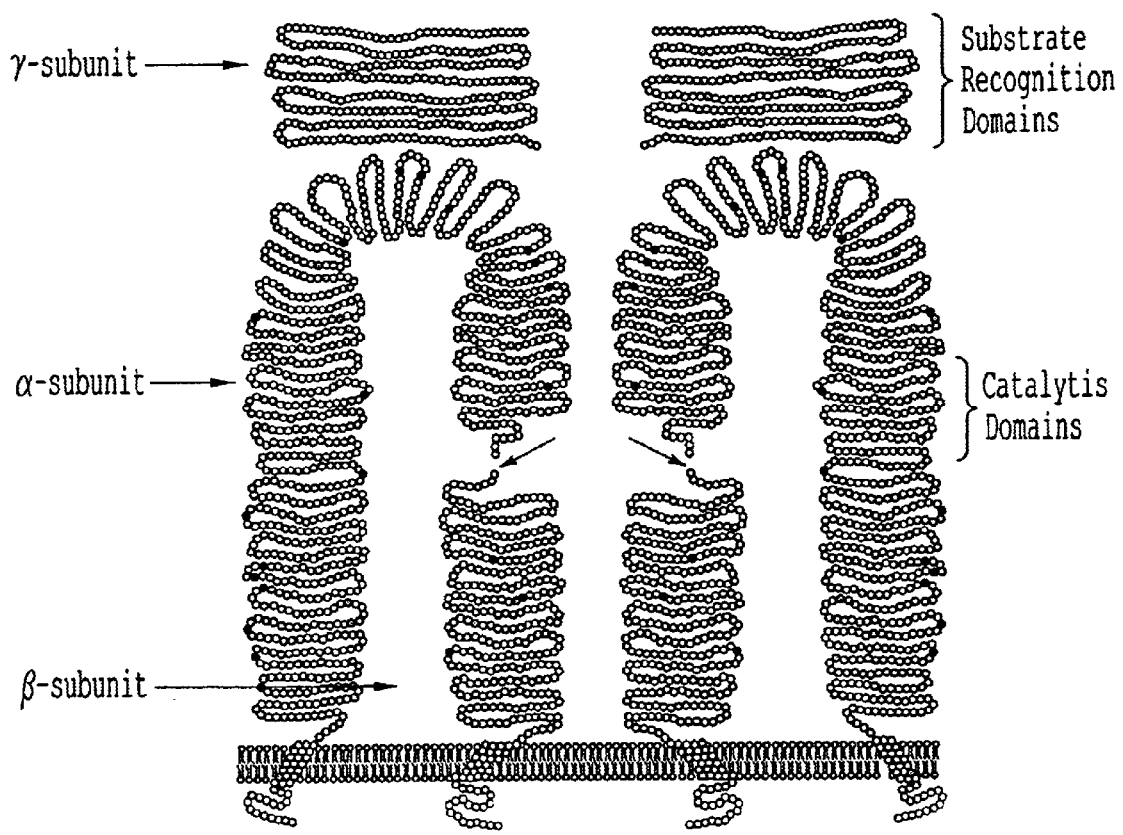

| | | | |
|---|---|---|---|
| 5,571,893 A | 11/1996 | Baker et al. | 530/350 |
| 5,576,424 A | 11/1996 | Mao et al. | 536/17.9 |
| 5,578,479 A | 11/1996 | Laderman et al. | 435/202 |
| 5,580,757 A | 12/1996 | Desnick et al. | 435/69.2 |
| 5,583,160 A | 12/1996 | Igarashi et al. | 514/869 |
| 5,585,247 A | 12/1996 | Habenstein | 435/18 |
| 5,612,206 A | 3/1997 | Valerio et al. | 435/172.13 |
| 5,621,106 A | 4/1997 | Dime | 546/183 |
| 5,624,806 A | 4/1997 | Baker et al. | 435/2.1 |
| 5,627,073 A | 5/1997 | Baker et al. | 435/351 |
| 5,627,171 A | 5/1997 | Park et al. | 514/114 |
| 5,633,228 A | 5/1997 | Lewis et al. | 514/12 |
| 5,633,261 A | 5/1997 | Dime | 514/299 |
| 5,639,607 A | 6/1997 | Desnick et al. | 435/6 |
| 5,639,939 A | 6/1997 | McCune, III | 800/2 |
| 5,648,229 A | 7/1997 | Habenstein | 435/18 |
| 5,648,335 A | 7/1997 | Lewis et al. | 514/12 |
| 5,658,567 A | 8/1997 | Calhoun et al. | 424/94.61 |
| 5,663,076 A | 9/1997 | Rostoker et al. | 438/14 |
| 5,663,254 A | 9/1997 | Lee et al. | 526/238.2 |
| 5,665,366 A | 9/1997 | Rawlings et al. | 424/401 |
| 5,679,545 A | 10/1997 | Baker et al. | 435/69.1 |
| 5,686,240 A | 11/1997 | Schuchman et al. | 435/6 |
| 5,691,181 A | 11/1997 | Lowe | 435/240.1 |
| 5,693,622 A | 12/1997 | Wolff et al. | 514/44 |
| 5,696,001 A | 12/1997 | Habenstein | 436/518 |
| 5,704,910 A | 1/1998 | Humes | 604/52 |
| 5,707,865 A | 1/1998 | Kohn et al. | 435/325 |
| 5,716,614 A | 2/1998 | Katz et al. | 424/94.3 |
| 5,719,031 A | 2/1998 | Haugland et al. | 435/7.4 |
| 5,721,367 A | 2/1998 | Kay et al. | 800/2 |
| 5,723,585 A | 3/1998 | Baker et al. | 530/413 |
| 5,728,381 A | 3/1998 | Wilson et al. | 424/94.6 |
| RE35,770 E | 4/1998 | Lormeau et al. | 514/56 |
| 5,736,360 A | 4/1998 | Gaulton et al. | 495/69.1 |
| 5,741,957 A | 4/1998 | Deboer et al. | 800/2 |
| 5,750,172 A | 5/1998 | Meade et al. | 426/580 |
| 5,759,775 A | 6/1998 | Caras et al. | 435/6 |
| 5,773,236 A | 6/1998 | Diwu et al. | 435/15 |
| 5,773,278 A | 6/1998 | Schuchman et al. | 435/358 |
| 5,792,647 A | 8/1998 | Roseman et al. | 435/252.3 |
| 5,798,239 A | 8/1998 | Wilson et al. | 435/183 |
| 5,798,366 A | 8/1998 | Platt et al. | 514/315 |
| 5,798,448 A | 8/1998 | Caras et al. | 530/388.1 |
| 5,807,943 A | 9/1998 | Lee et al. | 526/238.2 |
| 5,830,711 A | 11/1998 | Barany et al. | 435/91.1 |
| 5,830,850 A | 11/1998 | Gelb et al. | 514/2 |
| 5,830,916 A | 11/1998 | Hannum et al. | 514/625 |
| 5,840,578 A | 11/1998 | Desnick | 435/325 |
| 5,849,885 A | 12/1998 | Nuyens et al. | 530/416 |
| 5,851,782 A | 12/1998 | Hannun et al. | 435/2.96 |
| 5,854,207 A | 12/1998 | Lee et al. | 514/2 |
| 5,858,351 A | 1/1999 | Podsakoff et al. | 424/93.2 |
| 5,858,744 A | 1/1999 | Baum et al. | 435/122.13 |
| 5,858,755 A | 1/1999 | Lowe | 435/198 |
| 5,861,491 A | 1/1999 | Nuijens et al. | 530/417 |
| 5,871,946 A | 2/1999 | Lucas et al. | 435/18 |
| 5,874,297 A | 2/1999 | Wu et al. | 435/320.11 |
| 5,879,937 A | 3/1999 | Roncarolo | 435/325 |
| 5,906,817 A | 5/1999 | Moullier et al. | 424/93.21 |
| 5,911,704 A | 6/1999 | Humes | 604/93 |
| 5,912,146 A | 6/1999 | Nishimura et al. | 435/914 |
| 5,914,231 A | 6/1999 | Hennink et al. | 435/6 |
| 5,916,870 A | 6/1999 | Lee et al. | 514/2 |
| 5,916,911 A | 6/1999 | Shayman et al. | 514/428 |
| 5,917,122 A | 6/1999 | Byrne | 800/18 |
| 5,919,690 A | 7/1999 | Knap et al. | 435/208 |
| 5,919,913 A | 7/1999 | Nuyens et al. | 530/395 |
| 5,928,928 A | 7/1999 | Aerts | 435/201 |
| 5,929,036 A | 7/1999 | McEver | 514/25 |
| 5,929,304 A | 7/1999 | Radin et al. | 800/288 |
| 5,932,211 A | 8/1999 | Wilson et al. | 424/946 |
| 5,939,279 A | 8/1999 | Smith et al. | 435/7.32 |
| 5,968,502 A | 10/1999 | Treco et al. | 424/93.21 |
| 6,118,045 A | 9/2000 | Reuser et al. | 800/14 |

OTHER PUBLICATIONS

Schutzbach, J.S., et al. (1990) J. Biol. Chem. 265(5), 2546–2549.*

Alan D. Elbein et al, "Kifunensine, A Potent Inhibitor of the Glycoprotein Processing Mannosidase I", The Journal of Biological Chemistry, vol. 265, No. 26, Issue of Sep. 15, 1990 pp. 15599–15605.

Sly, "The Missing Link in Lysosomal Enzyme Targeting", The Journal of Clinical Investigation, vol. 105, No. 5, pp. 563–564, Mar. 2000.

Raas–Rothschild et al., "Molecular Basis of Variant Pseudo–Hurler Polydystrophy (Mucolipidosis IIIC)", The Journal of Clinical Investigation, vol. 105, pp. 673–681, Mar. 2000.

Bao et al., "Bovine Udp–N–Acetyglucosamine: Lysosoma-l–Enzyme N–Acetylglucosamine–1–Phosphotransferase", The Journal of Biological Chemistry, vol. 271, No. 49, pp. 31446–31451, Dec. 6, 1996.

Kornfeld, R. et al. "Molecular Cloning and Functional Expression of Two Splice Forms of Human N–Acetylglucosamine–1–phophodiester alpha–N–Acetyl-glucosaminidase" J. Biol. Chem., Nov. 1999. vol. 274, No. 46, pp. 32778–32785.

Cuozzo, J.W. et al. "Lysine is a Common Determinant for Mannose Phosphorylation of Lysosomal Proteins" J. Biol. Chem., May 1994. Vol. 269, No. 20. Pp. 14490–14496.

Kornfeld, S. "Trafficking of Lysosomal Enzymes in Normal and Disease States", J. Clin. Invest., vol. 77, Jan. 1986, pp. 1–6.

Kornfeld, S. "Lysosomal Enzyme Targeting", Biochemical Society Transactions, Jubilee Lecture Delivered on Dec. 19, 1989, vol. 18, pp. 367–374.

Jin Kyu Lee et al., "Purification and Characterization of Human Serum N–Acetylglucosamine–1–phosphodiester α–N–Acetylglucosaminidase", Archives of Biochemistry and Biophysics, vol. 319, No. 2, Jun. 1, 1995, pp. 412–425.

Karen Ghessling Mullis et al., "Characterization and Immunolocalization of Bovine N–Acetylglucosamine–1–phosphodiesterα–N–Acetylglucosaminidase", The Journal of Biological Chemistry, vol. 269, No. 3, Issue of Jan. 21, 1994, pp. 1727–1733.

Zhao K–W, et al., "Purification and Characterization of Human Lymphoblast N Acetylglucosamine–1–Phosphotransferase", Glycobiology, vol. 2, No. 2, (1992), pp. 119–125.

Nagase T, et al., "Prediction of the Coding Sequences of Unidentified Human Genes XV. the Complete Sequence of 100 New CDNA Clones from Brain which Code for Large Proteins in Vivo", DNA Research, vol. 6, No. 5, Oct. (1999), pp. 337–345.

Database SWALLPROT 'Online!, Nov. 1, 1996 retrieved from EBI Database accession No. Q61340.

* cited by examiner

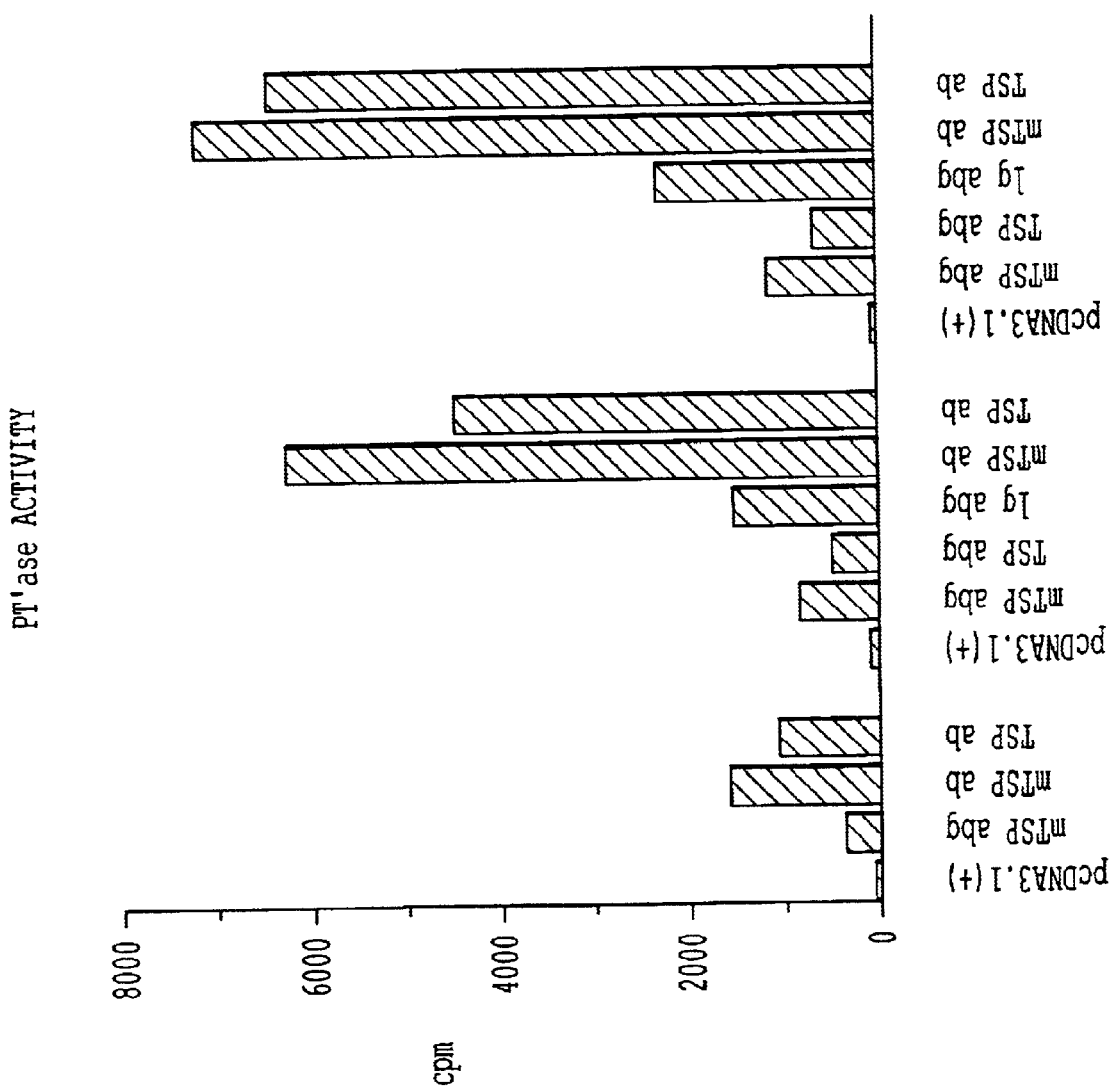

SEQUENCE LISTING

```
<160> NUMBER OF SEQ ID NOS: 52

<210> SEQ ID NO 1
<211> LENGTH: 928
<212> TYPE: PRT
<213> ORGANISM: Homo sapiens

<400> SEQUENCE: 1

Met Leu Phe Lys Leu Leu Gln Arg Gln Thr Tyr Thr Cys Leu Ser His
1               5                   10                  15

Arg Tyr Gly Leu Tyr Val Cys Phe Leu Gly Val Val Val Thr Ile Val
            20                  25                  30

Ser Ala Phe Gln Phe Gly Glu Val Val Leu Glu Trp Ser Arg Asp Gln
        35                  40                  45

Tyr His Val Leu Phe Asp Ser Tyr Arg Asp Asn Ile Ala Gly Lys Ser
    50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
                85                  90                  95

Arg Glu Gln Met Glu Glu Glu Gln Lys Ala Met Arg Glu Ile Leu Gly
            100                 105                 110

Lys Asn Thr Thr Glu Pro Thr Lys Lys Ser Glu Lys Gln Leu Glu Cys
        115                 120                 125

Leu Leu Thr His Cys Ile Lys Val Pro Met Leu Val Leu Asp Pro Ala
    130                 135                 140

Leu Pro Ala Asn Ile Thr Leu Lys Asp Val Pro Ser Leu Tyr Pro Ser
145                 150                 155                 160

Phe His Ser Ala Ser Asp Ile Phe Asn Val Ala Lys Pro Lys Asn Pro
                165                 170                 175
```

-continued

```
Ser Thr Asn Val Ser Val Val Phe Asp Ser Thr Lys Asp Val Glu
            180                 185                 190

Asp Ala His Ser Gly Leu Leu Lys Gly Asn Ser Arg Gln Thr Val Trp
        195                 200                 205

Arg Gly Tyr Leu Thr Thr Asp Lys Glu Val Pro Gly Leu Val Leu Met
        210                 215                 220

Gln Asp Leu Ala Phe Leu Ser Gly Phe Pro Pro Thr Phe Lys Glu Thr
225                 230                 235                 240

Asn Gln Leu Lys Thr Lys Leu Pro Glu Asn Leu Ser Ser Lys Val Lys
                245                 250                 255

Leu Leu Gln Leu Tyr Ser Glu Ala Ser Val Ala Leu Leu Lys Leu Asn
            260                 265                 270

Asn Pro Lys Asp Phe Gln Glu Leu Asn Lys Gln Thr Lys Lys Asn Met
        275                 280                 285

Thr Ile Asp Gly Lys Glu Leu Thr Ile Ser Pro Ala Tyr Leu Leu Trp
        290                 295                 300

Asp Leu Ser Ala Ile Ser Gln Ser Lys Gln Asp Glu Asp Ile Ser Ala
305                 310                 315                 320

Ser Arg Phe Glu Asp Asn Glu Glu Leu Arg Tyr Ser Leu Arg Ser Ile
                325                 330                 335

Glu Arg His Ala Pro Trp Val Arg Asn Ile Phe Ile Val Thr Asn Gly
            340                 345                 350

Gln Ile Pro Ser Trp Leu Asn Leu Asp Asn Pro Arg Val Thr Ile Val
        355                 360                 365

Thr His Gln Asp Val Phe Arg Asn Leu Ser His Leu Pro Thr Phe Ser
        370                 375                 380

Ser Pro Ala Ile Glu Ser His Ile His Arg Ile Glu Gly Leu Ser Gln
385                 390                 395                 400

Lys Phe Ile Tyr Leu Asn Asp Asp Val Met Phe Gly Lys Asp Val Trp
                405                 410                 415

Pro Asp Asp Phe Tyr Ser His Ser Lys Gly Gln Lys Val Tyr Leu Thr
            420                 425                 430

Trp Pro Val Pro Asn Cys Ala Glu Gly Cys Pro Gly Ser Trp Ile Lys
        435                 440                 445

Asp Gly Tyr Cys Asp Lys Ala Cys Asn Asn Ser Ala Cys Asp Trp Asp
        450                 455                 460

Gly Gly Asp Cys Ser Gly Asn Ser Gly Gly Ser Arg Tyr Ile Ala Gly
465                 470                 475                 480

Gly Gly Gly Thr Gly Ser Ile Gly Val Gly His Pro Trp Gln Phe Gly
                485                 490                 495

Gly Gly Ile Asn Ser Val Ser Tyr Cys Asn Gln Gly Cys Ala Asn Ser
            500                 505                 510

Trp Leu Ala Asp Lys Phe Cys Asp Gln Ala Cys Asn Val Leu Ser Cys
        515                 520                 525

Gly Phe Asp Ala Gly Asp Cys Gly Gln Asp His Phe His Glu Leu Tyr
        530                 535                 540

Lys Val Ile Leu Leu Pro Asn Gln Thr His Tyr Ile Ile Pro Lys Gly
545                 550                 555                 560

Glu Cys Leu Pro Tyr Phe Ser Phe Ala Glu Val Ala Lys Arg Gly Val
                565                 570                 575

Glu Gly Ala Tyr Ser Asp Asn Pro Ile Ile Arg His Ala Ser Ile Ala
            580                 585                 590
```

```
Asn Lys Trp Lys Thr Ile His Leu Ile Met His Ser Gly Met Asn Ala
            595                 600                 605

Thr Thr Ile His Phe Asn Leu Thr Phe Gln Asn Thr Asn Asp Glu Glu
    610                 615                 620

Phe Lys Met Gln Ile Thr Val Glu Val Asp Thr Arg Glu Gly Pro Lys
625                 630                 635                 640

Leu Asn Ser Thr Ala Gln Lys Gly Tyr Glu Asn Leu Val Ser Pro Ile
            645                 650                 655

Thr Leu Leu Pro Glu Ala Glu Ile Leu Phe Glu Asp Ile Pro Lys Glu
                660                 665                 670

Lys Arg Phe Pro Lys Phe Lys Arg His Asp Val Asn Ser Thr Arg Arg
            675                 680                 685

Ala Gln Glu Glu Val Lys Ile Pro Leu Val Asn Ile Ser Leu Leu Pro
            690                 695                 700

Lys Asp Ala Gln Leu Ser Leu Asn Thr Leu Asp Leu Gln Leu Glu His
705                 710                 715                 720

Gly Asp Ile Thr Leu Lys Gly Tyr Asn Leu Ser Lys Ser Ala Leu Leu
                725                 730                 735

Arg Ser Phe Leu Met Asn Ser Gln His Ala Lys Ile Lys Asn Gln Ala
                740                 745                 750

Ile Ile Thr Asp Glu Thr Asn Asp Ser Leu Val Ala Pro Gln Glu Lys
            755                 760                 765

Gln Val His Lys Ser Ile Leu Pro Asn Ser Leu Gly Val Ser Glu Arg
    770                 775                 780

Leu Gln Arg Leu Thr Phe Pro Ala Val Ser Val Lys Val Asn Gly His
785                 790                 795                 800

Asp Gln Gly Gln Asn Pro Pro Leu Asp Leu Glu Thr Thr Ala Arg Phe
                805                 810                 815

Arg Val Glu Thr His Thr Gln Lys Thr Ile Gly Gly Asn Val Thr Lys
            820                 825                 830

Glu Lys Pro Pro Ser Leu Ile Val Pro Leu Glu Ser Gln Met Thr Lys
            835                 840                 845

Glu Lys Lys Ile Thr Gly Lys Glu Lys Glu Asn Ser Arg Met Glu Glu
850                 855                 860

Asn Ala Glu Asn His Ile Gly Val Thr Val Leu Leu Gly Arg Lys
865                 870                 875                 880

Leu Gln His Tyr Thr Asp Ser Tyr Leu Gly Phe Leu Pro Trp Glu Lys
                885                 890                 895

Lys Lys Tyr Phe Gln Asp Leu Leu Asp Glu Glu Ser Leu Lys Thr
            900                 905                 910

Gln Leu Ala Tyr Phe Thr Asp Ser Lys Asn Thr Gly Arg Gln Leu Lys
            915                 920                 925

<210> SEQ ID NO 2
<211> LENGTH: 328
<212> TYPE: PRT
<213> ORGANISM: Homo sapiens

<400> SEQUENCE: 2

Asp Thr Phe Ala Asp Ser Leu Arg Tyr Val Asn Lys Ile Leu Asn Ser
1               5                   10                  15

Lys Phe Gly Phe Thr Ser Arg Lys Val Pro Ala His Met Pro His Met
            20                  25                  30

Ile Asp Arg Ile Val Met Gln Glu Leu Gln Asp Met Phe Pro Glu Glu
        35                  40                  45
```

-continued

```
Phe Asp Lys Thr Ser Phe His Lys Val Arg His Ser Glu Asp Met Gln
    50                  55                  60
Phe Ala Phe Ser Tyr Phe Tyr Leu Met Ser Ala Val Gln Pro Leu
65                  70                  75                  80
Asn Ile Ser Gln Val Phe Asp Glu Val Asp Thr Asp Gln Ser Gly Val
                    85                  90                  95
Leu Ser Asp Arg Glu Ile Arg Thr Leu Ala Thr Arg Ile His Glu Leu
                100                 105                 110
Pro Leu Ser Leu Gln Asp Leu Thr Gly Leu Glu His Met Leu Ile Asn
            115                 120                 125
Cys Ser Lys Met Leu Pro Ala Asp Ile Thr Gln Leu Asn Asn Ile Pro
    130                 135                 140
Pro Thr Gln Glu Ser Tyr Tyr Asp Pro Asn Leu Pro Pro Val Thr Lys
145                 150                 155                 160
Ser Leu Val Thr Asn Cys Lys Pro Val Thr Asp Lys Ile His Lys Ala
                165                 170                 175
Tyr Lys Asp Lys Asn Lys Tyr Arg Phe Glu Ile Met Gly Glu Glu Glu
                180                 185                 190
Ile Ala Phe Lys Met Ile Arg Thr Asn Val Ser His Val Val Gly Gln
            195                 200                 205
Leu Asp Asp Ile Arg Lys Asn Pro Arg Lys Phe Val Cys Leu Asn Asp
    210                 215                 220
Asn Ile Asp His Asn His Lys Asp Ala Gln Thr Val Lys Ala Val Leu
225                 230                 235                 240
Arg Asp Phe Tyr Glu Ser Met Phe Pro Ile Pro Ser Gln Phe Glu Leu
                245                 250                 255
Pro Arg Glu Tyr Arg Asn Arg Phe Leu His Met His Glu Leu Gln Glu
                260                 265                 270
Trp Arg Ala Tyr Arg Asp Lys Leu Lys Phe Trp Thr His Cys Val Leu
            275                 280                 285
Ala Thr Leu Ile Met Phe Thr Ile Phe Ser Phe Ala Glu Gln Leu
    290                 295                 300
Ile Ala Leu Lys Arg Lys Ile Phe Pro Arg Arg Ile His Lys Glu
305                 310                 315                 320
Ala Ser Pro Asn Arg Ile Arg Val
                325

<210> SEQ ID NO 3
<211> LENGTH: 305
<212> TYPE: PRT
<213> ORGANISM: Homo sapiens
<220> FEATURE:
<221> NAME/KEY: SIGNAL
<222> LOCATION: (1)..(24)
<223> OTHER INFORMATION:

<400> SEQUENCE: 3

Met Ala Ala Gly Leu Ala Arg Leu Leu Leu Leu Leu Gly Leu Ser Ala
1               5                   10                  15
Gly Gly Pro Ala Pro Ala Gly Ala Ala Lys Met Lys Val Val Glu Glu
                20                  25                  30
Pro Asn Ala Phe Gly Val Asn Asn Pro Phe Leu Pro Gln Ala Ser Arg
            35                  40                  45
Leu Gln Ala Lys Arg Asp Pro Ser Pro Val Ser Gly Pro Val His Leu
    50                  55                  60
```

Phe Arg Leu Ser Gly Lys Cys Phe Ser Leu Val Glu Ser Thr Tyr Lys
65                  70                  75                  80

Tyr Glu Phe Cys Pro Phe His Asn Val Thr Gln His Glu Gln Thr Phe
                85                  90                  95

Arg Trp Asn Ala Tyr Ser Gly Ile Leu Gly Ile Trp His Glu Trp Glu
            100                 105                 110

Ile Ala Asn Asn Thr Phe Thr Gly Met Trp Met Arg Asp Gly Asp Ala
        115                 120                 125

Cys Arg Ser Arg Ser Arg Gln Ser Lys Val Glu Leu Ala Cys Gly Lys
    130                 135                 140

Ser Asn Arg Leu Ala His Val Ser Glu Pro Ser Thr Cys Val Tyr Ala
145                 150                 155                 160

Leu Thr Phe Glu Thr Pro Leu Val Cys His Pro His Ala Leu Leu Val
                165                 170                 175

Tyr Pro Thr Leu Pro Glu Ala Leu Gln Arg Gln Trp Asp Gln Val Glu
            180                 185                 190

Gln Asp Leu Ala Asp Glu Leu Ile Thr Pro Gln Gly His Glu Lys Leu
        195                 200                 205

Leu Arg Thr Leu Phe Glu Asp Ala Gly Tyr Leu Lys Thr Pro Glu Glu
    210                 215                 220

Asn Glu Pro Thr Gln Leu Glu Gly Gly Pro Asp Ser Leu Gly Phe Glu
225                 230                 235                 240

Thr Leu Glu Asn Cys Arg Lys Ala His Lys Glu Leu Ser Lys Glu Ile
                245                 250                 255

Lys Arg Leu Lys Gly Leu Leu Thr Gln His Gly Ile Pro Tyr Thr Arg
            260                 265                 270

Pro Thr Glu Thr Ser Asn Leu Glu His Leu Gly His Glu Thr Pro Arg
        275                 280                 285

Ala Lys Ser Pro Glu Gln Leu Arg Gly Asp Pro Gly Leu Arg Gly Ser
    290                 295                 300

Leu
305

<210> SEQ ID NO 4
<211> LENGTH: 5597
<212> TYPE: DNA
<213> ORGANISM: Homo sapiens

<400> SEQUENCE: 4
cggagccgag cgggcgtccg tcgccggagc tgcaatgagc ggcgcccgga ggctgtgacc      60
tgcgcgcggc ggcccgaccg gggcccctga atggcggctc gctgaggcgg cggcggcggc     120
ggcggctcag gctcctcggg gcgtggcgtg gcggtgaagg ggtgatgctg ttcaagctcc     180
tgcagagaca aacctatacc tgcctgtccc acaggtatgg gctctacgtg tgcttcttgg     240
gcgtcgttgt caccatcgtc tccgccttcc agttcggaga ggtggttctg gaatggagcc     300
gagatcaata ccatgttttg tttgattcct atagagacaa tattgctgga agtcctttc      360 agaatcggct ttgtctgccc atgccgattg acgttgttta cacctgggtg aatggcacag     420
atcttgaact actgaaggaa ctacagcagg tcagagaaca gatggaggag gagcagaaag     480
caatgagaga aatccttggg aaaaacacaa cggaacctac taagaagagt gagaagcagt     540
tagagtgttt gctaacacac tgcattaagg tgccaatgct tgtactggac ccagccctgc     600
cagccaacat caccctgaag gacgtgccat ctctttatcc ttcttttcat tctgccagtg     660
acattttcaa tgttgcaaaa ccaaaaaacc cttctaccaa tgtctcagtt gttgttttttg    720

```
acagtactaa ggatgttgaa gatgcccact ctggactgct taaaggaaat agcagacaga    780
cagtatggag ggggtacttg acaacagata agaagtccc tggattagtg ctaatgcaag     840
atttggcttt cctgagtgga tttccaccaa cattcaagga aacaaatcaa ctaaaaacaa    900
aattgccaga aaatctttcc tctaaagtca aactgttgca gttgtattca gaggccagtg    960
tagcgcttct aaaactgaat aaccccaagg attttcaaga attgaataag caaactaaga   1020
agaacatgac cattgatgga aaagaactga ccataagtcc tgcatattta ttatgggatc   1080
tgagcgccat cagccagtct aagcaggatg aagacatctc tgccagtcgt tttgaagata   1140
acgaagaact gaggtactca ttgcgatcta tcgagaggca tgcaccatgg gttcggaata   1200
ttttcattgt caccaacggg cagattccat cctggctgaa ccttgacaat cctcgagtga   1260
caatagtaac acaccaggat gttttcgaa atttgagcca cttgcctacc tttagttcac    1320
ctgctattga aagtcacatt catcgcatcg aagggctgtc ccagaagttt atttacctaa   1380
atgatgatgt catgtttggg aaggatgtct ggccagatga ttttacagt cactccaaag    1440 gccagaaggt ttatttgaca tggcctgtgc caaactgtgc cgagggctgc ccaggttcct   1500
ggattaagga tggctattgt gacaaggctt gtaataattc agcctgcgat tgggatggtg   1560
gggattgctc tggaaacagt ggagggagtc gctatattgc aggaggtgga ggtactggga   1620
gtattggagt tggacacccc tggcagtttg gtggaggaat aaacagtgtc tcttactgta   1680
atcagggatg tgcgaattcc tggctcgctg ataagttctg tgaccaagca tgcaatgtct   1740
tgtcctgtgg gtttgatgct ggcgactgtg ggcaagatca ttttcatgaa ttgtataaag   1800
tgatccttct cccaaaccag actcactata ttattccaaa aggtgaatgc ctgccttatt   1860
tcagctttgc agaagtagcc aaaagaggag ttgaaggtgc ctatagtgac aatccaataa   1920
ttcgacatgc ttctattgcc aacaagtgga aaaccatcca cctcataatg cacagtggaa   1980
tgaatgccac cacaatacat tttaatctca cgtttcaaaa tacaaacgat gaagagttca   2040
aaatgcagat aacagtggag gtggacacaa gggagggacc aaaactgaat tctacggccc   2100
agaagggtta cgaaaattta gttagtccca taacacttct tccagaggcg gaaatccttt   2160
ttgaggatat tcccaaagaa aaacgcttcc cgaagtttaa gagacatgat gttaactcaa   2220
caaggagagc ccaggaagag gtgaaaattc ccctggtaaa tatttcactc cttccaaaag   2280
acgcccagtt gagtctcaat accttggatt tgcaactgga acatggagac atcactttga   2340
aaggatacaa tttgtccaag tcagccttgc tgagatcatt tctgatgaac tcacagcatg   2400
ctaaaataaa aaatcaagct ataataacag atgaaacaaa tgacagtttg gtggctccac   2460
aggaaaaaca ggttcataaa agcatcttgc caaacagctt aggagtgtct gaaagattgc   2520
agaggttgac ttttcctgca gtgagtgtaa aagtgaatgg tcatgaccag ggtcagaatc   2580 caccctgga cttggagacc acagcaagat ttagagtgga aactcacacc caaaaaacca   2640
taggcggaaa tgtgacaaaa gaaaagcccc catctctgat tgttccactg gaaagccaga   2700
tgacaaaaga aagaaaatc acaggaaag aaaagagaa cagtagaatg gaggaaaatg      2760
ctgaaaatca cataggcgtt actgaagtgt tacttggaag aaagctgcag cattacacag   2820
atagttactt gggctttttg ccatgggaga aaaaaagta tttccaagat cttctcgacg    2880
aagaagagtc attgaagaca caattggcat acttcactga tagcaaaaat actgggaggc   2940
aactaaaaga tacatttgca gattccctca gatatgtaaa taaaattcta aatagcaagt   3000
ttggattcac atcgcggaaa gtccctgctc acatgcctca catgattgac cggattgtta   3060
```

-continued

```
tgcaagaact gcaagatatg ttccctgaag aatttgacaa gacgtcattt cacaaagtgc    3120
gccattctga ggatatgcag tttgccttct cttattttta ttatctcatg agtgcagtgc    3180
agccactgaa tatatctcaa gtctttgatg aagttgatac agatcaatct ggtgtcttgt    3240
ctgacagaga aatccgaaca ctggctacca gaattcacga actgccgtta agtttgcagg    3300
atttgacagg tctggaacac atgctaataa attgctcaaa aatgcttcct gctgatatca    3360
cgcagctaaa taatattcca ccaactcagg aatcctacta tgatcccaac ctgccaccgg    3420
tcactaaaag tctagtaaca aactgtaaac cagtaactga caaaatccac aaagcatata    3480
aggacaaaaa caaatatagg tttgaaatca tgggagaaga agaaatcgct tttaaaatga    3540
ttcgtaccaa cgtttctcat gtggttggcc agttggatga cataagaaaa accctagga    3600
agtttgtttg cctgaatgac aacattgacc acaatcataa agatgctcag acagtgaagg    3660
ctgttctcag ggacttctat gaatccatgt tccccatacc ttcccaattt gaactgccaa    3720
gagagtatcg aaaccgtttc cttcatatgc atgagctgca ggaatggagg cttatcgag    3780
acaaattgaa gttttggacc cattgtgtac tagcaacatt gattatgttt actatattct    3840
cattttttgc tgagcagtta attgcactta gcggaagat atttcccaga aggaggatac    3900
acaaagaagc tagtcccaat cgaatcagag tatagaagat cttcatttga aaaccatcta    3960
cctcagcatt tactgagcat tttaaaactc agcttcacag agatgtcttt gtgatgtgat    4020
gcttagcagt ttggcccgaa gaaggaaaat atccagtacc atgctgtttt gtggcatgaa    4080
tatagcccac tgactaggaa ttatttaacc aacccactga aaacttgtgt gtcgagcagc    4140
tctgaactga ttttactttt aaagaatttg ctcatggacc tgtcatcctt tttataaaaa    4200
ggctcactga caagagacag ctgttaattt cccacagcaa tcattgcaga ctaacttat    4260
taggagaagc ctatgccagc tgggagtgat tgctaagagg ctccagtctt tgcattccaa    4320
agccttttgc taaagtttg cacttttttt ttttcatttc ccattttaa gtagttacta    4380
agttaactag ttattcttgc ttctgagtat aacgaattgg gatgtctaaa cctattttta    4440
tagatgttat ttaaataatg cagcaatatc acctcttatt gacaatacct aaattatgag    4500
ttttattaat atttaagact gtaaatggtc ttaaaccact aactactgaa gagctcaatg    4560
attgacatct gaaatgcttt gtaattattg acttcagccc ctaagaatgc tatgatttca    4620
cgtgcaggtc taatttcaac aggctagagt tagtactact taccagatgt aattatgttt    4680
tggaaatgta catattcaaa cagaagtgcc tcattttaga aatgagtagt gctgatggca    4740
ctggcacatt acagtggtgt cttgtttaat actcattggt atattccagt agctatctct    4800
ctcagttggt ttttgataga acagaggcca gcaaactttc tttgtaaaag gctggttagt    4860
aaattattgc aggccacctg tgtctttgtc atacattctt cttgctgttg tttagtttgt    4920
ttttttttcaa acaaccctct aaaaatgtaa aaaccatgtt tagcttgcag ctgtacaaaa    4980
actgcccacc agccagatgt gaccctcagg ccatcatttg ccaatcactg agaattattt    5040
ttgttgttgt tgttgttgtt gtttttgaga cagagtctct ctctgttgcc caggctggag    5100
tgcagtggcg caatctcagc tcactgcaac ctccgcctcc cgggttcaag cagttctgtc    5160
tcagccttct gagtagctgg gactacaggt gcatgccacc acaccctgct aattttgta    5220
tttttagtag agacgggggt tccaccatat tggtcaggct tatcttgaac tcctgacctc    5280
aggtgatcca cctgcctctg cctcccaaag tgctgagatt acaggcataa gccagtgcac    5340
ccagccgaga attagtattt ttatgtatgg ttaaaccttg gcgtctagcc atattttatg    5400
tcataataca atggatttgt gaagagcaga ttccatgagt aactctgaca ggtattttag    5460
```

```
atcatgatct caacaatatt cctcccaaat ggcatacatc ttttgtacaa agaacttgaa      5520
atgtaaatac tgtgtttgtg ctgtaagagt tgtgtatttc aaaaactgaa atctcataaa      5580
aagttaaatt ttgaaaa                                                    5597
```

<210> SEQ ID NO 5
<211> LENGTH: 1219
<212> TYPE: DNA
<213> ORGANISM: Homo sapiens
<220> FEATURE:
<221> NAME/KEY: sig_peptide
<222> LOCATION: (24)..(95)
<223> OTHER INFORMATION:

<400> SEQUENCE: 5

```
gtagagcgca ggtgcgcggc tcgatggcgg cggggctggc gcggctcctg ttgctcctcg       60
ggctctcggc cggcgggccc cgccggcag gtgcagcgaa gatgaaggtg gtggaggagc      120
ccaacgcgtt tggggtgaac aacccgttct tgcctcaggc cagtcgcctc caggccaaga     180
gggatccttc acccgtgtct ggacccgtgc atctcttccg actctcgggc aagtgcttca     240
gcctggtgga gtccacgtac aagtatgagt tctgcccgtt ccacaacgtg acccagcacg     300
agcagacctt ccgctggaac gcctacagtg ggatcctcgg catctggcac gagtgggaga     360
tcgccaacaa caccttcacg ggcatgtgga tgagggacgg tgacgcctgc cgttcccgga     420
gccggcagag caagtggag ctggcgtgtg gaaaaagcaa ccggctggcc catgtgtccg     480
agccgagcac ctgcgtctat cgcctgacgt tcgagacccc cctcgtctgc cacccccacg     540
ccttgctagt gtacccaacc ctgccagagg ccctgcagcg gcagtgggac caggtagagc     600
aggacctggc cgatgagctg atcaccccc agggccatga aagttgctg aggacacttt       660 ttgaggatgc tggctactta aagacccag aagaaaatga acccacccag ctggagggag     720
gtcctgacag cttggggttt gagaccctgg aaaactgcag gaaggctcat aaagaactct     780
caaaggagat caaaggctg aaaggttgc tcacccagca cggcatcccc tacacgaggc      840
ccacagaaac ttccaacttg gagcacttgg gccacgagac gcccagagcc aagtctccag     900
agcagctgcg gggtgaccca ggactgcgtg ggagtttgtg accttgtggt gggagagcag    960
aggtggacgc ggccgagagc cctacagaga agctggctgg taggacccgc aggaccagct   1020
gaccaggctt gtgctcagag aagcagacaa aacaaagatt caaggtttta attaattccc   1080
atactgataa aaataactcc atgaattctg taaaccattg cataaatgct atagtgtaaa   1140
aaaatttaaa caagtgttaa ctttaaacag ttcgctacaa gtaaatgatt ataaatacta   1200
aaaaaaaaaa aaaaaaaaa                                                 1219
```

<210> SEQ ID NO 6
<211> LENGTH: 515
<212> TYPE: PRT
<213> ORGANISM: Homo sapiens
<220> FEATURE:
<221> NAME/KEY: SIGNAL
<222> LOCATION: (1)..(24)
<223> OTHER INFORMATION:
<221> NAME/KEY: PROPEP
<222> LOCATION: (25)..(49)
<223> OTHER INFORMATION:

<400> SEQUENCE: 6

```
Met Ala Thr Ser Thr Gly Arg Trp Leu Leu Leu Arg Leu Ala Leu Phe
1               5                   10                  15
```

```
Gly Phe Leu Trp Glu Ala Ser Gly Gly Leu Asp Ser Gly Ala Ser Arg
            20                  25                  30

Asp Asp Asp Leu Leu Leu Pro Tyr Pro Arg Ala Arg Ala Arg Leu Pro
            35                  40                  45

Arg Asp Cys Thr Arg Val Arg Ala Gly Asn Arg Glu His Glu Ser Trp
50                  55                  60

Pro Pro Pro Pro Ala Thr Pro Gly Ala Gly Leu Ala Val Arg Thr
65                  70                  75                  80

Phe Val Ser His Phe Arg Asp Arg Ala Val Ala Gly His Leu Thr Arg
                    85                  90                  95

Ala Val Glu Pro Leu Arg Thr Phe Ser Val Leu Glu Pro Gly Gly Pro
                    100                 105                 110

Gly Gly Cys Ala Ala Arg Arg Ala Thr Val Glu Thr Ala Arg
                    115                 120                 125

Ala Ala Asp Cys Arg Val Ala Gln Asn Gly Gly Phe Phe Arg Met Asn
            130                 135                 140

Ser Gly Glu Cys Leu Gly Asn Val Val Ser Asp Glu Arg Arg Val Ser
145                 150                 155                 160

Ser Ser Gly Gly Leu Gln Asn Ala Gln Phe Gly Ile Arg Arg Asp Gly
                    165                 170                 175

Thr Leu Val Thr Gly Tyr Leu Ser Glu Glu Val Leu Asp Thr Glu
            180                 185                 190

Asn Pro Phe Val Gln Leu Leu Ser Gly Val Val Trp Leu Ile Arg Asn
            195                 200                 205

Gly Ser Ile Tyr Ile Asn Glu Ser Gln Ala Thr Glu Cys Asp Glu Thr
            210                 215                 220

Gln Glu Thr Gly Ser Phe Ser Lys Phe Val Asn Val Ile Ser Ala Arg
225                 230                 235                 240

Thr Ala Ile Gly His Asp Arg Lys Gly Gln Leu Val Leu Phe His Ala
                    245                 250                 255

Asp Gly His Thr Glu Gln Arg Gly Ile Asn Leu Trp Glu Met Ala Glu
            260                 265                 270

Phe Leu Leu Lys Gln Asp Val Val Asn Ala Ile Asn Leu Asp Gly Gly
            275                 280                 285

Gly Ser Ala Thr Phe Val Leu Asn Gly Thr Leu Ala Ser Tyr Pro Ser
            290                 295                 300

Asp His Cys Gln Asp Asn Met Trp Arg Cys Pro Arg Gln Val Ser Thr
305                 310                 315                 320

Val Val Cys Val His Glu Pro Arg Cys Gln Pro Asp Cys His Gly
                    325                 330                 335

His Gly Thr Cys Val Asp Gly His Cys Gln Cys Thr Gly His Phe Trp
            340                 345                 350

Arg Gly Pro Gly Cys Asp Glu Leu Asp Cys Gly Pro Ser Asn Cys Ser
            355                 360                 365

Gln His Gly Leu Cys Thr Glu Thr Gly Cys Arg Cys Asp Ala Gly Trp
            370                 375                 380

Thr Gly Ser Asn Cys Ser Glu Glu Cys Pro Leu Gly Trp His Gly Pro
385                 390                 395                 400

Gly Cys Gln Arg Arg Cys Lys Cys Glu His His Cys Pro Cys Asp Pro
                    405                 410                 415

Lys Thr Gly Asn Cys Ser Val Ser Arg Val Lys Gln Cys Leu Gln Pro
            420                 425                 430

Pro Glu Ala Thr Leu Arg Ala Gly Glu Leu Ser Phe Phe Thr Arg Thr
```

```
                435                 440                 445
Ala Trp Leu Ala Leu Thr Leu Ala Leu Ala Phe Leu Leu Leu Ile Ser
        450                 455                 460

Ile Ala Ala Asn Leu Ser Leu Leu Leu Ser Arg Ala Glu Arg Asn Arg
465                 470                 475                 480

Arg Leu His Gly Asp Tyr Ala Tyr His Pro Leu Gln Glu Met Asn Gly
                485                 490                 495

Glu Pro Leu Ala Ala Glu Lys Glu Gln Pro Gly Gly Ala His Asn Pro
            500                 505                 510

Phe Lys Asp
        515

<210> SEQ ID NO 7
<211> LENGTH: 2183
<212> TYPE: DNA
<213> ORGANISM: Homo sapiens

<400> SEQUENCE: 7
```

| | | | | | |
|---|---|---|---|---|---|
| atggcgacct | ccacgggtcg | ctggcttctc | ctccggcttg | cactattcgg | cttcctctgg | 60 |
| gaagcgtccg | gcggcctcga | ctcggggggcc | tcccgcgacg | acgacttgct | actgccctat | 120 |
| ccacgcgcgc | gcgcgcgcct | ccccgggac | tgcacacggg | tgcgcgccgg | caaccgcgag | 180 |
| cacgagagtt | ggcctccgcc | tcccgcgact | cccggcgccg | gcggtctggc | cgtgcgcacc | 240 |
| ttcgtgtcgc | acttcaggga | ccgcgcgtg | gccgccacc | tgacgcgggc | cgttgagccc | 300 |
| ctgcgcacct | tctcggtgct | ggagcccggt | ggacccggcg | gctgcgcggc | gagacgacgc | 360 |
| gccaccgtgg | aggagacggc | gcgggcggcc | gactgccgtg | tcgcccagaa | cggcggcttc | 420 |
| ttccgcatga | actcgggcga | gtgcctgggg | aacgtggtga | gcgacgagcg | gcgggtgagc | 480 |
| agctccgggg | ggctgcagaa | cgcgcagttc | gggatccgcc | gcgacgggac | cctggtcacc | 540 |
| gggtacctgt | ctgaggagga | ggtgctggac | actgagaacc | catttgtgca | gctgctgagt | 600 |
| ggggtcgtgt | ggctgattcg | taatggaagc | atctacatca | cgagagcca | agccacagag | 660 |
| tgtgacgaga | cacaggagac | aggttccttt | agcaaatttg | tgaatgtgat | atcagccagg | 720 |
| acggccattg | ccacgaccg | gaaagggcag | ctggtgctct | tcatgcagca | cggcctacg | 780 |
| gagcagcgtg | gcatcaacct | gtgggaaatg | gcggagttcc | tgctgaaaca | ggacgtggtc | 840 |
| aacgccatca | acctgatgg | gggtggctct | gccacctttg | tgctcaacgg | gaccttggcc | 900 |
| agttaccccgt | cagatcactg | ccaggacaac | atgtggcgct | gtcccgcca | agtgtccacc | 960 |
| gtggtgtgtg | tgcacgaacc | ccgctgccag | ccgcctgact | gccacggcca | cgggacctgc | 1020 |
| gtggacgggc | actgccaatg | caccgggcac | ttctggcggg | gtcccggctg | tgatgagctg | 1080 |
| gactgtggcc | cctctaactg | cagccagcac | ggactgtgca | cggagaccgg | ctgccgctgt | 1140 |
| gatgccggat | ggaccgggtc | caactgcagt | gaagagtgtc | cccttggctg | gcatgggccg | 1200 |
| ggctgccaga | ggcgttgtaa | gtgtgagcac | cattgtccct | gtgaccccaa | gactggcaac | 1260 |
| tgcagcgtct | ccagagtaaa | gcagtgtctc | cagcccacct | aagccaccct | gagggcggga | 1320 |
| gaactctcct | ttttcaccag | gaccgcctgg | ctagccctca | ccctggcgct | ggccttcctc | 1380 |
| ctgctgatca | gcattgcagc | aaacctgtcc | ttgctcctgt | ccagagcaga | gaggaaccgg | 1440 |
| cgcctgcatg | ggactatgc | ataccacccg | ctgcaggaga | tgaacgggga | gcctctggcc | 1500 |
| gcagagaagg | agcagccagg | gggcgcccac | aaccccttca | aggactgaag | cctcaagctg | 1560 |
| cccggggtgg | cacgtcgcga | aagcttgttt | ccccacggtc | tggcttctgc | agggggaaatt | 1620 |

-continued

| | |
|---|---|
| tcaaggccac tggcgtggac catctgggtg tcctcaatgg ccctgtggg gcagccaagt | 1680 |
| tcctgatagc acttgtgcct cagcccctca cctggccacc tgccagggca cctgcaaccc | 1740 |
| tagcaatacc atgctcgctg agaggctca gctgcctgct tctcgcctgc ctgtgtctgc | 1800 |
| tgccgagaag cccgtgcccc cgggagggct gccgcactgc caaagagtct ccctcctcct | 1860 |
| ggggaagggg ctgccaacga accagactca gtgaccacgt catgacagaa cagcacatcc | 1920 |
| tggccagcac ccctggctgg agtgggttaa agggacgagt ctgccttcct ggctgtgaca | 1980 |
| cgggaccct tttctacaga cctcatcact ggatttgcca actagaattc gatttcctgt | 2040 |
| cataggaagc tccttggaag aagggatggg gggatgaaat catgtttaca gacctgtttt | 2100 |
| gtcatcctgc tgccaagaag ttttttaatc acttgaataa attgatataa taaaggagc | 2160 |
| caccaggtgg tgtgtggatt ctg | 2183 |

<210> SEQ ID NO 8
<211> LENGTH: 328
<212> TYPE: PRT
<213> ORGANISM: Mus musculus

<400> SEQUENCE: 8

```
Asp Thr Phe Ala Asp Ser Leu Arg Tyr Val Asn Lys Ile Leu Asn Ser
1               5                   10                  15

Lys Phe Gly Phe Thr Ser Arg Lys Val Pro Ala His Met Pro His Met
                20                  25                  30

Ile Asp Arg Ile Val Met Gln Glu Leu Gln Asp Met Phe Pro Glu Glu
            35                  40                  45

Phe Asp Lys Thr Ser Phe His Lys Val Arg His Ser Glu Asp Met Gln
        50                  55                  60

Phe Ala Phe Ser Tyr Phe Tyr Leu Met Ser Ala Val Gln Pro Leu
65                  70                  75                  80

Asn Ile Ser Gln Val Phe His Glu Val Asp Thr Asp Gln Ser Gly Val
                85                  90                  95

Leu Ser Asp Arg Glu Ile Arg Thr Leu Ala Thr Arg Ile His Asp Leu
            100                 105                 110

Pro Leu Ser Leu Gln Asp Leu Thr Gly Leu Glu His Met Leu Ile Asn
        115                 120                 125

Cys Ser Lys Met Leu Pro Ala Asn Ile Thr Gln Leu Asn Asn Ile Pro
    130                 135                 140

Pro Thr Gln Glu Ala Tyr Tyr Asp Pro Asn Leu Pro Pro Val Thr Lys
145                 150                 155                 160

Ser Leu Val Thr Asn Cys Lys Pro Val Thr Asp Lys Ile His Lys Ala
                165                 170                 175

Tyr Lys Asp Lys Asn Lys Tyr Arg Phe Glu Ile Met Gly Glu Glu Glu
            180                 185                 190

Ile Ala Phe Lys Met Ile Arg Thr Asn Val Ser His Val Val Gly Gln
        195                 200                 205

Leu Asp Asp Ile Arg Lys Asn Pro Arg Lys Phe Val Cys Leu Asn Asp
    210                 215                 220

Asn Ile Asp His Asn His Lys Asp Ala Arg Thr Val Lys Ala Val Leu
225                 230                 235                 240

Arg Asp Phe Tyr Glu Ser Met Phe Pro Ile Pro Ser Gln Phe Glu Leu
                245                 250                 255

Pro Arg Glu Tyr Arg Asn Arg Phe Leu His Met His Glu Leu Gln Glu
            260                 265                 270
```

```
Trp Arg Ala Tyr Arg Asp Lys Leu Lys Phe Trp Thr His Cys Val Leu
            275                 280                 285

Ala Thr Leu Ile Ile Phe Thr Ile Phe Ser Phe Phe Ala Glu Gln Ile
        290                 295                 300

Ile Ala Leu Lys Arg Lys Ile Phe Pro Arg Arg Ile His Lys Glu
305                 310                 315                 320

Ala Ser Pro Asp Arg Ile Arg Val
                325

<210> SEQ ID NO 9
<211> LENGTH: 307
<212> TYPE: PRT
<213> ORGANISM: Mus musculus

<400> SEQUENCE: 9

Met Ala Gly Arg Leu Ala Gly Phe Leu Met Leu Leu Gly Leu Ala Ser
1               5                   10                  15

Gln Gly Pro Ala Pro Ala Cys Ala Gly Lys Met Lys Val Val Glu Glu
            20                  25                  30

Pro Asn Thr Phe Gly Leu Asn Asn Pro Phe Leu Pro Gln Ala Ser Arg
        35                  40                  45

Leu Gln Pro Lys Arg Glu Pro Ser Ala Val Ser Gly Pro Leu His Leu
    50                  55                  60

Phe Arg Leu Ala Gly Lys Cys Phe Ser Leu Val Glu Ser Thr Tyr Lys
65                  70                  75                  80

Tyr Glu Phe Cys Pro Phe His Asn Val Thr Gln His Glu Gln Thr Phe
                85                  90                  95

Arg Trp Asn Ala Tyr Ser Gly Ile Leu Gly Ile Trp His Glu Trp Glu
            100                 105                 110

Ile Ile Asn Asn Thr Phe Lys Gly Met Trp Met Thr Asp Gly Asp Ser
        115                 120                 125

Cys His Ser Arg Ser Arg Gln Ser Lys Val Glu Leu Thr Cys Gly Lys
    130                 135                 140

Ile Asn Arg Leu Ala His Val Ser Glu Pro Ser Thr Cys Val Tyr Ala
145                 150                 155                 160

Leu Thr Phe Glu Thr Pro Leu Val Cys His Pro His Ser Leu Leu Val
                165                 170                 175

Tyr Pro Thr Leu Ser Glu Ala Leu Gln Gln Arg Leu Asp Gln Val Glu
            180                 185                 190

Gln Asp Leu Ala Asp Glu Leu Ile Thr Pro Gln Gly Tyr Glu Lys Leu
        195                 200                 205

Leu Arg Val Leu Phe Glu Asp Ala Gly Tyr Leu Lys Val Pro Gly Glu
    210                 215                 220

Thr His Pro Thr Gln Leu Ala Gly Gly Ser Lys Gly Leu Gly Leu Glu
225                 230                 235                 240

Thr Leu Asp Asn Cys Arg Lys Ala His Ala Glu Leu Ser Gln Glu Val
                245                 250                 255

Gln Arg Leu Thr Ser Leu Leu Gln Gln His Gly Ile Pro His Thr Gln
            260                 265                 270

Pro Thr Glu Thr Thr His Ser Gln His Leu Gly Gln Gln Leu Pro Ile
        275                 280                 285

Gly Ala Ile Ala Ala Glu His Leu Arg Ser Asp Pro Gly Leu Arg Gly
    290                 295                 300

Asn Ile Leu
305
```

<210> SEQ ID NO 10
<211> LENGTH: 2070
<212> TYPE: DNA
<213> ORGANISM: Mus musculus
<220> FEATURE:
<221> NAME/KEY: misc_feature
<222> LOCATION: (186)..(186)
<223> OTHER INFORMATION: n is a, t, g, or c

<400> SEQUENCE: 10

| | | | | | |
|---|---|---|---|---|---|
| gtgagaccct | aggagcaatg | gccgggcggc | tggctggctt | cctgatgttg | ctggggctcg | 60 |
| cgtcgcaggg | gcccgcgccg | gcatgtgccg | ggaagatgaa | ggtggtggag | gagcctaaca | 120 |
| cattcgggtg | agcggatcac | ggtcctgcgg | cttggggacc | gagcctggct | ggttcttctg | 180 |
| accttntcaa | ttccataggc | tgaataaccc | gttcttgccc | caggcaagcc | gccttcagcc | 240 |
| caagagagag | ccttcagctg | tatcccgcaa | attaagagaa | attaatttca | aacgatttag | 300 |
| aaagtattct | agccaggcga | tgatggcgca | cgcctttaat | cccagcactt | gggaggcaga | 360 |
| ggcaggcaga | tttccgagtt | caaggccatc | agaactgact | gtacatctta | gtacagttta | 420 |
| gcatgtgatc | agagatctga | atcacaaagc | tgggcctgcg | tggtaaagca | ggtcctttct | 480 |
| aataaggttg | cagtttagat | tttctttctt | aactctttta | ttctttgaga | cagggttttct | 540 |
| caacagtggg | tgtcctggaa | ctcacttttg | taaaccaggc | tgcccttaaa | ctcacaaagc | 600 |
| tctgtcagcc | tctgcctcct | gagtgctggg | attaaaggtc | cacaccctgt | tcattcattt | 660 |
| ttaattttg | agactgggtc | tcattatgtg | gccctagaca | gatactgaga | gcctcctcca | 720 |
| caggaacaag | catgggaatc | ctgccacaga | caaccagttc | tgtggtctgg | agatgagttt | 780 |
| gtcagtccct | aggagttagg | tcagcctgcc | tctgcattcc | caataattta | ggaaaggagc | 840 |
| ttggggcgtt | ctggccttga | tggttagtgc | cctcctgcca | accttagctt | ccagctttag | 900 |
| gggtagcaga | gtttataccg | atgctaaact | gctgttgtgt | tcttcccag | ggcccctgca | 960 |
| tctcttcaga | cttgctggca | agtgcttag | cctagtggag | tccacgtgag | tgccaggctg | 1020 |
| gtgggtggag | tgggcggagt | ctgcagagct | cctgatgtgc | ctgtgtttcc | caggtacaag | 1080 |
| tatgaattct | gcccttttcca | caacgtcacc | cagcacgagc | agaccttccg | ctggaatgcc | 1140 |
| tacagcggga | tccttggcat | ctggcatgag | tgggaaatca | tcaacaatac | cttcaagggc | 1200 |
| atgtggatga | ctgatgggga | ctcctgccac | tcccggagcc | ggcagagcaa | ggtggagctc | 1260 |
| acctgtggaa | agatcaaccg | actggcccac | gtgtctgagc | caagcacctg | tgtctatgca | 1320 |
| ttgacattcg | agacccctct | tgtttgccat | ccccactctt | tgttagtgta | tccaactctg | 1380 |
| tcagaagccc | tgcagcagcc | cttggaccag | gtggaacagg | acctggcaga | tgaactgatc | 1440 |
| acaccacagg | gctatgagaa | gttgctaagg | gtacttttg | aggatgctgg | ctacttaaag | 1500 |
| gtcccaggag | aaacccatcc | cacccagctg | gcaggaggtt | ccaagggcct | ggggcttgag | 1560 |
| actctggaca | actgtagaaa | ggcacatgca | gagctgtcac | aggaggtaca | aagactgacg | 1620 |
| agtctgctgc | aacagcatgg | aatcccccac | actcagccca | caggtcagtc | tgcctgccct | 1680 |
| ggtcagctgc | cagccactcc | ggggcctgca | gcactgggc | agatctttat | tgctacccat | 1740 |
| tctggcagaa | accactcact | ctcagcacct | gggtcagcag | ctccccatag | gtgcaatcgc | 1800 |
| agcagagcat | ctgcggagtg | acccaggact | acgtgggaac | atcctgtgag | caaggtggcc | 1860 |
| acgaagaata | gaaatatcct | gagctttgag | tgtcctttca | cagagtgaac | aaaactggtg | 1920 |
| tggtgtagac | acggcttctt | ttggcatatt | ctagatcaga | cagtgtcact | gacaaacaag | 1980 |

```
agggacctgc tggccagcct ttgttgtgcc caaagatcca gacaaaataa agattcaaag    2040 tttttaattaa aaaaaaaaaa aaaggaattc                                    2070
```

<210> SEQ ID NO 11
<211> LENGTH: 113
<212> TYPE: PRT
<213> ORGANISM: Rattus rattus

<400> SEQUENCE: 11

```
Phe Pro Pro Thr Phe Lys Glu Thr Ser Gln Leu Lys Thr Lys Leu Pro
1               5                   10                  15

Glu Asn Leu Ser Ser Lys Ile Lys Leu Leu Gln Leu Tyr Ser Glu Ala
            20                  25                  30

Ser Val Ala Leu Leu Lys Leu Asn Asn Pro Lys Gly Phe Pro Glu Leu
        35                  40                  45

Asn Lys Gln Thr Lys Lys Asn Met Ser Ile Ser Gly Lys Glu Leu Ala
    50                  55                  60

Ile Ser Pro Ala Tyr Leu Leu Trp Asp Leu Ser Ala Ile Ser Gln Ser
65                  70                  75                  80

Lys Gln Asp Glu Asp Val Ser Ala Ser Arg Phe Glu Asp Asn Glu Glu
                85                  90                  95

Leu Arg Tyr Ser Leu Arg Ser Ile Glu Arg His Asp Ser Met Ser Pro
            100                 105                 110

Leu
```

<210> SEQ ID NO 12
<211> LENGTH: 460
<212> TYPE: DNA
<213> ORGANISM: Rattus rattus

<400> SEQUENCE: 12

```
attcccacca acattcaagg agacgagtca gctgaagaca aaactgccag aaaatctttc     60
ttctaaaata aaactgttgc agctgtactc ggaggccagc gtcgctcttc tgaaattgaa    120
taaccccaaa ggtttccccg agctgaacaa gcagaccaag aagaacatga gcatcagtgg    180
gaaggaactg gccatcagcc ctgcctatct gctgtgggac ctgagcgcca tcagccagtc    240
caagcaggat gaagatgtgt ctgccagccg cttcgaggat aacgaagagc tgaggtactc    300
actgagatct atcgagagac atgattccat gagtcccttta tgaattctgg ccatatcttc    360
aatcatgatc tcagtagtat tcctctgaaa tggcacacat ttttctaatg agaacttgaa    420
atgtaaatat tgtgtttgtg ctgtaaattt tgtgtatttc                          460
```

<210> SEQ ID NO 13
<211> LENGTH: 502
<212> TYPE: PRT
<213> ORGANISM: Drosophila melanogaster

<400> SEQUENCE: 13

```
Gly Thr Arg Arg Phe Asp Asp Lys Asn Glu Leu Arg Tyr Ser Leu Arg
1               5                   10                  15

Ser Leu Glu Lys His Ala Ala Trp Ile Arg His Val Tyr Ile Val Thr
            20                  25                  30

Asn Gly Gln Ile Pro Ser Trp Leu Asp Leu Ser Tyr Glu Arg Val Thr
        35                  40                  45

Val Val Pro His Glu Val Leu Ala Pro Asp Pro Asp Gln Leu Pro Thr
    50                  55                  60
```

-continued

```
Phe Ser Ser Ser Ala Ile Glu Thr Phe Leu His Arg Ile Pro Lys Leu
 65                  70                  75                  80

Ser Lys Arg Phe Leu Tyr Leu Asn Asp Asp Ile Phe Leu Gly Ala Pro
                 85                  90                  95

Leu Tyr Pro Glu Asp Leu Tyr Thr Glu Ala Glu Gly Val Arg Val Tyr
            100                 105                 110

Gln Ala Trp Met Val Pro Gly Cys Ala Leu Asp Cys Pro Trp Thr Tyr
            115                 120                 125

Ile Gly Asp Gly Ala Cys Asp Arg His Cys Asn Ile Asp Ala Cys Gln
        130                 135                 140

Phe Asp Gly Gly Asp Cys Ser Glu Thr Gly Pro Ala Ser Asp Ala His
145                 150                 155                 160

Val Ile Pro Pro Ser Lys Glu Val Leu Glu Val Gln Pro Ala Ala Val
                165                 170                 175

Pro Gln Ser Arg Val His Arg Phe Pro Gln Met Gly Leu Gln Lys Leu
            180                 185                 190

Phe Arg Arg Ser Ser Ala Asn Phe Lys Asp Val Met Arg His Arg Asn
        195                 200                 205

Val Ser Thr Leu Lys Glu Leu Arg Arg Ile Val Glu Arg Phe Asn Lys
210                 215                 220

Ala Lys Leu Met Ser Leu Asn Pro Glu Leu Glu Thr Ser Ser Ser Glu
225                 230                 235                 240

Pro Gln Thr Thr Gln Arg His Gly Leu Arg Lys Glu Asp Phe Lys Ser
                245                 250                 255

Ser Thr Asp Ile Tyr Ser His Ser Leu Ile Ala Thr Asn Met Leu Leu
            260                 265                 270

Asn Arg Ala Tyr Gly Phe Lys Ala Arg His Val Leu Ala His Val Gly
        275                 280                 285

Phe Leu Ile Asp Lys Asp Ile Val Glu Ala Met Gln Arg Arg Phe His
        290                 295                 300

Gln Gln Ile Leu Asp Thr Ala His Gln Arg Phe Arg Ala Pro Thr Asp
305                 310                 315                 320

Leu Gln Tyr Ala Phe Ala Tyr Tyr Ser Phe Leu Met Ser Glu Thr Lys
            325                 330                 335

Val Met Ser Val Glu Glu Ile Phe Asp Glu Phe Asp Thr Asp Gly Ser
            340                 345                 350

Ala Thr Trp Ser Asp Arg Glu Val Arg Thr Phe Leu Thr Arg Ile Tyr
        355                 360                 365

Gln Pro Pro Leu Asp Trp Ser Ala Met Arg Tyr Phe Glu Glu Val Val
        370                 375                 380

Gln Asn Cys Thr Arg Asn Leu Gly Met His Leu Lys Val Asp Thr Val
385                 390                 395                 400

Glu His Ser Thr Leu Val Tyr Glu Arg Tyr Glu Asp Ser Asn Leu Pro
            405                 410                 415

Thr Ile Thr Arg Asp Leu Val Val Arg Cys Pro Leu Leu Ala Glu Ala
            420                 425                 430

Leu Ala Ala Asn Phe Ala Val Arg Pro Lys Tyr Asn Phe His Val Ser
        435                 440                 445

Pro Lys Arg Thr Ser His Ser Asn Phe Met Met Leu Thr Ser Asn Leu
        450                 455                 460

Thr Glu Val Val Glu Ser Leu Asp Arg Leu Arg Arg Asn Pro Arg Lys
465                 470                 475                 480

Phe Asn Cys Ile Asn Asp Asn Leu Asp Ala Asn Arg Gly Glu Asp Asn
```

485                 490                 495
Glu Asp Gly Ala Pro Ser
            500

<210> SEQ ID NO 14
<211> LENGTH: 9792
<212> TYPE: DNA
<213> ORGANISM: Mus musculus

<400> SEQUENCE: 14

| | | | | | |
|---|---|---|---|---|---|
| caggctcggg | acttactata | acacaggaca | cttgtcacct | gaaagcttga | gtcagtcagt | 60 |
| tattatggtc | tgtgtgtgag | atacaagtgg | gtgcataggc | agtggtgcac | acatgtagat | 120 |
| cagactttct | acagccaatt | ctcttcttcc | tcctctccat | gggttcaggg | tcttcatctc | 180 |
| aggttgcaca | gcgagttcat | ttatgtgctg | tgccatctcg | ccagtcgttc | ctatatccta | 240 |
| gaggaaaact | agtttcttct | ggtcaagagg | aggaaagagt | ggagacctgt | cattctaaga | 300 |
| tacccaaaac | agggccaggt | tggggacctg | tgcctttaat | cccatcactt | ggggattagg | 360 |
| tagaagcaag | aggctctaga | ccagtctaca | cactgaattt | caagccagcc | tacctataaa | 420 |
| tcagagaccc | tgcttcaaaa | ataaaattaa | acaaaaacga | agataaaacca | agctacccaa | 480 |
| aacacaagag | ttaatccagt | cagacaggtc | tagcaaatgc | taggatgaaa | ggtgtgcacc | 540 |
| accacgagtg | ggctgcaagc | ctctctctct | ctctctctct | ctctctctct | ctcgtttgtt | 600 |
| ttgtttttcg | agacaaggtt | tctctgtgta | gccctggctg | tcctggaact | cactctgtag | 660 |
| accaggctgg | cctcgagctt | cactcttaaa | agttcctctt | cctcctcctc | catcttttcc | 720 |
| tcctcttacc | ccctaggctc | cttttcctct | tcttgtcttt | cagataaagt | ctcaagtagt | 780 |
| ccagactggt | ctcaaactaa | ctaactagcc | aagaatagcc | aacctcttaa | cttccgattc | 840 |
| tcctgcctct | gctgaatgct | ggggttgtgg | cgtgggccac | cacttctggt | ttgtgcaaca | 900 |
| cagaaggaac | tagggcttta | agcacgagaa | gcaagttctg | tacagactta | cacaggccca | 960 |
| gcatctgttc | ttgcaatttt | ctgtaagttt | gacataatat | gagaataaaa | agctatctat | 1020 |
| ctcccttcca | gccttaccct | ctctgatgga | attcgaatgc | gtaatcaaag | cacccaacag | 1080 |
| cctggcctga | aatcacgtgg | ggcaagccca | cgtgaccgga | gcaccaatcc | aatatggcgg | 1140 |
| cgcccagggg | gcccgggctg | ttcctcatac | ccgcgctgct | cggcttactc | ggggtggcgt | 1200 |
| ggtgcagctt | aagcttcggg | tgagtgcaag | ccgccggggc | cagcctggct | ggggtccacc | 1260 |
| tttcctgagc | gctctcaggc | acagccctcc | gacctcacga | tcgccccgtc | cctgcagggt | 1320 |
| ttcccgcgac | gatgacctgc | tgctgcctta | cccactagcg | cgcagacgtc | cctcgcgaga | 1380 |
| ctgcgcccgg | gtgcgctcag | gtagcccaga | gcaggagagc | tggcctccgc | cacctctggc | 1440 |
| cacccacgaa | ccccgggcgc | caagccacca | cgcggccgtg | cgcaccttcg | tgtcgcactt | 1500 |
| cgaggggcgc | gcggtggccg | gccacctgac | gcgggtcgcc | gatcccctac | gcactttctc | 1560 |
| ggtgctggag | cccggaggag | ccggggggctg | cggcggcaga | agcgccgcgg | ctactgtgga | 1620 |
| ggacacagcc | gtccgggccg | gttgccgcat | cgctcagaac | ggtggcttct | tccgcatgag | 1680 |
| cactggcgag | tgcttgggga | acgtggtgag | cgacgggcgg | ctggtgagca | gctcaggggg | 1740 |
| actgcagaac | gcgcagttcg | gtatccgacg | cgatggaacc | atagtcaccg | ggtgaggagg | 1800 |
| cagggagccc | cggggctgta | gagggcaaag | ggtctctgat | gttctttcag | agccatgcct | 1860 |
| ccgagtccag | gtccctaacc | aaacttcctg | tctttcttct | tccgagtaat | gacgctgaca | 1920 |
| ccttccttcc | tttaagttta | ttcatgtgcc | actgaataat | ctgtgatcag | gccgtgtgtg | 1980 |

-continued

```
gggacttggg gaggcgaccg tgagcctgaa cacagtttgt gccctagtga actttgtgta      2040
gtattagaga acatttcgt gttcaacgaa gccatggaac caattggaaa tagtgtagag      2100
tttatggagc agtcccagac agctagctgg aggccttttg ctgtcctgat aaaaatccag      2160
gttagacaag gagcttgttg agggcagcct ttggaagttt ctgtgtttct gaaatttga       2220
cagcagccag agttgacagc aggcaggcag gagtagaagg tagcgccatc tggtgttcca      2280
gttctcttcc aaggttccgt ttttttgccaa ggctgggaag tgggctttcc ccaactcttc     2340
tcagcccttg gttgcaattt ctgggcctgc ccatgtatct ggttcttcat ccttcaacat      2400
cagccagtgt caccactgtt gatcttaggt tttcacagat cctaaaactt ctgccagtga      2460
ccagcgcctg cagtttctct tccctggctc tgtccttcaa cctctctaca ttccagccat      2520
ctccctagct cctctcttgg actccctttc agacttgttg tcatgatcac tgtctcagaa      2580
cccctattgc tcctttacaa tggtccactg acctgctcac ctcctacttt ttttttttaa      2640
atgtgtgtgc atctgtgtgt gcctgagggg agaccagagt ttgatttcaa atgtcttcta      2700
ttctcttttc ctccatctta ttttctaaca caaaatctga atctagagat cactggttca      2760
gttaacctgg ctggccggta aaccccaggg ccctcctgct tccctctgtc cacccacccc      2820
cagcactaag gctacagtgt gtgctgttcc agccagcttt ctcatgggtg ctgaggatct      2880
gaacgcaggt tcacatgtgt ggtgggaagg cttttaccca atgctctgtc tttccagccc      2940
atcctccctt gttaactgcc aaacagctgc ctatcctgtc catgtgtagc tcactgctac      3000
ttcttttatt atgaggtcag cacatgttac taaagatggc aagagaagaa ggttcttca      3060
ttgtgtcata gctatagctc aggaggaatt ttatttcctg tgtaggcaca caggagagca      3120
tcttccagct cacactccaa ctgaactaac tgaacacctg cctatatatc caaagaaggg      3180
gtgtcagtgc caatcacagc acacctccag tgcaaatgaa ggtttgtgtt gcaccaatc      3240
acagccttgc ctctttagc atgcatcaca acaaagtcct cctagactat cagggatat      3300
gctctcttgg ccaagtagg aatagttgca gtgtcatctg gcacaaacca tttcaaacgg      3360
cctggctgag gttatgcctt cgggaacctg aagtctttgt gtggttgtct ccaagtgtct      3420
gtggagctcc aggcggctgg tgctgacaga cgctttgtct agttggctgt tgacttttg      3480
cttaagcagc cagggcagta gagtctaaca atgctaatt tcaggatcag gaagactgta      3540
gaaaaatgag catcaagaag cccctggtac ccaaagctgc tcttgccaat gagtgaacct      3600
ctgccttccc gcttccaggt cctgtcttga agaagaggtt ctggatcccg tgaatccgtt      3660
cgtgcagctg ctgagcggag tcgtgtggct catccgcaat ggaaacatct acatcaacga      3720
gagccaagcc atcgagtgtg acgagacaca ggagacaggt caggaagcac aggtgttctg      3780
ttttatttgt attaggtttt gatttgttta ttttgtgcat gcagcgggtg catgcatgct      3840
cctttccttt cgccatgtga gtcctgagta ttgaactcag actgttaagt gtgatgggag      3900
gcactttacc cactgagcca cttccccagc cctcagcatc agctttcttc agacccagga      3960
acagtgtgag tggttattc tttagtgttc ccaaacattt actgagcagc tatttactgt       4020
ttagcactat ggtgagagtc ctagggattc agtcttatgt agaatataga aggagaatcc      4080
ttggcaataa gctggaaaat tgtgacaagt gccaagaaag aaacaggaga aggggaccg       4140
gtggggacca gaagcacagg tatgaggaaa gtgcctgcag atttgctgta tggtggcctc      4200
cacatggcct aggagtttgt cataaatgca gagccatgag tccacctcc ctatacctcc       4260
catccagaaa ccactggtta aatcctaaca acttgggtgt gcaggcactc ccttggtgac      4320
tctgatggac actcaaggtc aagggccact tgggatggg ctgatgagtt ggcttggtca       4380
```

-continued

```
gtaaagtatt tgccttgaaa gtgtgaggac ctgagttgga gccccagaaa gaaacattaa    4440
aagccaagtg ctgggatgca cacttgcatt cccagggatg gagctggaag cagggatag    4500 gcagatccac ggccacacgg tgatattcta agctaacaag agacctgtct cacacagaaa    4560
gtgggtggca cctgaggacc aacacccagg gttatcctct gacgtacctc cagagtggaa    4620
aatactgggg tggtggaaaa ggacacttg gtcctgggaa tctggctatt cagggtatag    4680
tgtagaggga gagggagact caagaggctg tctttgagtc aaaggaacaa gctatcagaa    4740
gaactcaggg cagaggcctg tggttcccag gctcagggca gccttcaagg ccctaggcag    4800
agagtagctg ctgggtgaac aagtacagaa gtgaggcctg gggcctcagg caaggcctgt    4860
gaaatccttc caccaacata gaagtttctg gagactgaga tcacatgaag tgcttctggc    4920
tgtggcatgg aagctcactg gaggtggagc tgggatgtgg ctcagtgatc cagtgcttgc    4980
cacacgtgca cgaggaagg agccatcaaa agagagaaag tcgggagacc tgaggggtcc    5040
cctggagagc tgggtaacca ccccgggccc ttctccttta ggttctttta gcaaatttgt    5100
gaatgtgatg tcagccagga cagccgtggg tcatgaccgt gagggcagc ttatcctctt    5160 ccatgctgat ggacagacgg aacagcgtgg tgagtcccag gaaccttggg gctgtttgca    5220
cttcagccac cctacctttc cagtcggttc tggggtattg gtgggacaag acagctttcc    5280
ggccattttg gaagtttcat ctggaggcaa tagcatttac ctactagtga agaagccag    5340 ttaagccaga gaccacaggg gctcaagctg catacccct ctgcacagcc ttaacctatg    5400
ggagatggca gagttcctgc gtcaacaaga tgtcgtcaat gccatcaacc tggatggagg    5460
cggttctgct acttttgtgc tcaatgggac cctggccagt tacccttcag atcactggta    5520 agaaccctg agccaccttt gtggctctct cagactgtct cactcagtca atactgagac    5580
cctgttgtgt gccaggccct gggtatccaa aagtgagcag aagagccgag atctcttccc    5640
tcagggtgct gcacagccca tccctggaaa cctgagacag gtcaggaaag gcctccctga    5700
ggacagtgaa gtaagacctg aggagatggc tggccgggt tgagagagcc tttaccggaa    5760
gacaaactgt acgcaatggg gaaatccgct aagtggccca gggagaggct ggagctatag    5820
ctcaggagga aaagtacttg cctcgcaagc gaaggacctg agtttaaact ccaaaaccca    5880
tataaaaagc cagatacgag caagtggcac atgcttgcag tcccagcctt gttgaggaag    5940
agtcaggtga atcctgaccc tctggccagc cagcctagcc tacttttgg caaggtccag    6000 gccagcgaga aagataaata aaataaagtt ttaaatgaca tgtatctaag gttgtcctga    6060
ctccatatgc gcacgcacgc atgcacgcac gcacaactgg cagaatggaa agggaggcaa    6120
actggacagc ctttataggc tgcggcaggg accagcacca aggcctagac ctcgtctcac    6180
agtgaatccc ccacagccag acaacatgt ggcgctgtcc ccgccaagtg tccactgtgg    6240
tgtgtgtgca tgaaccgcgc tgccagccac ccgactgcag tggccatggg acctgtgtgg    6300
atggccactg tgaatgcacc agccacttct ggcggggcga ggcctgcagc gagctggact    6360
gtggcccctc caactgcagc cagcatgggc tgtgcacaga gagtgagtgg ggagcccaca    6420
ggagggtggt gctctggcgg gaccccagct cgcccatgct agactcccgc ctgtgtcctt    6480
acccagcctc tgtggtcttg ctttggtagc tggctgccac tgtgatgctg ggtggacagg    6540
atccaactgc agtgaaggtg agagctgcct gcaaacactc ctggagaggg tggcctggct    6600
gcacgcagct ggtatgacgc cttcgtccct ccttctggct tggaacttac cttcagagcc    6660
ttttctcatt tcgcatgtgg atacccgatg ttctacctac tgaaagagcc cacaagtagg    6720
```

```
aagccagatt ttcagtattg tcactcaact ctaaggacca atagcaaaaa acaaagtgg   6780 ccacgcccct gagggagatc caccaaagtc cttaactcct ggaaagcagc tcctggtgat   6840
cctaggcatg ggtagggtgg tttcagcatc agctcagtgg agttcccatt cataatttct   6900 tcatccttt  aaggtcataa gttctagagc ccaccttaaa tctaggcagt attcttggtg   6960
tttatctgag acaaagtctt atacagccca cgcagttctc taacttagta tgtaaccgag   7020
aatggcctca agcaacctgc ttcctccttt caagcgctgg gattataggc atagcaccaa   7080
cttatagggt gctagaagtc aaacccaggg ccctatgtat atgcagcaag cactctagaa   7140
actggaacac agccctgttt gcagcccggt taccttggag ggttgggtcc cagggatctg   7200
agggcatctc cttcagcatg gccatgtgca cacccaggag ccaggctgtc tgtgacagga   7260
gaccatgcca cccaaggtga gacctccctg ccaccatctc ctctccacag agtgtcctct   7320
gggctggtat gggccaggtt gccagaggcc ctgccagtgt gagcaccagt gtttctgtga   7380
cccgcagact ggcaactgca gcatctccca aggtatgcgg ccttaaaggt tcttgagctg   7440
ggagcccttg gggcaggtct ggggtaggtg gactctcccc agcccttctt tctggtgtct   7500
tgcagtgagg cagtgtctcc agccaactga ggctacgccg agggcaggag agctggcctc   7560
tttcaccagg taagtgtttt agcaggcact gagcccctat gtctcatccg tgaggcacta   7620
gccaggccag gaggtcacag gttaccctct actttgcaag ctcagggaca gtcacaggta   7680
aaactggcat ccaggaaaga ccctgagcta cccagtggaa ctcaaaggta gcaggctatg   7740
ggtgtcatgc ctctggctgc agagactcca cttagatgct ggagcagggc catagagaca   7800
ggaaggactc accttatttc tgaactcttc cgtgtgttca ggctttgtgt tgttgttgct   7860
tcctttctgc tgtttcctgg gtttccagct ccatccccac agggctcatg gaagaattg    7920 tgaagcaggg ggtgtggctc aattggcaga ttgattgcct ggcatgcaga aagccctagg   7980
ttcaatcccc agcatttcat atcataaccc aggcatggtg gcatcatgtg cctgtaagtc   8040
cagcacttgg gaggtagaag cagaaaagcc acgagtttaa gaatgttagg gagtcttagg   8100
ccaacctggg atacctaaga caagagatag atgtagggag atagattgac agacagacag   8160
acagacagac agacagacag atcttgagct ggaccttctg gcacaagcct gtcatcctag   8220
ctattccagg aagctgaagc aggaagatag caaattcaag gccagcttaa gccacagatt   8280
gagttcaaga tcaacctgag caactttatg aaatcctatt ataacataaa aagtaggggt   8340
gggaggttag gctgtagctc agtggtgagt gattgccta gcacgcacaa gacccaggtt    8400
caattcccag tactgcaaaa aatatattag gaacccccta aaagcagtaa cattcacatt   8460
agatgtgtgt gtgtgtgtgt gtgtgtgtgt gtgtgtgtgt gtgtgtgtgt gtgtgttttg   8520
ttgggtattt atttcattta catttccaat gctatcccaa aagtccccca catcctcccc   8580
cacccaccac cttgttttt tttttttttt tttttttttt tttgacctga aactcacagg    8640
ttaggttaga caagctgact ggtgagctcc aacttccaac gtaccatcat gcctggcttt   8700
tgttttggtg tctctgtgta accctggatg tcctggagct ctctctgtag accagcctgg   8760
ccttaaactc acagaaaccc acctgtttct gcctcccatg tgctgggatt aaaggcgtgt   8820
gccacctcac ccagccctgc tggacttaaa ttgggtcttc atttttataag acaagcatga   8880 gctaattccc cagttcctaa aatgttttta acatccttaa acatcagaga ctgtctgtgg   8940
tattccctcc atgtgtcttc agtataccta ctcccctccc tgcctactgg gttcaacatg   9000
cccagtttgg gttctggctg cctgccccca ctcaagactc tcttttccat ctcaggacca   9060
cctggctagc cctcaccctg acactaattt tcctgctgct gatcagcact ggggtcaacg   9120
```

```
tgtccttgtt cctgggctcc agggccgaga ggaaccggca cctcgacggg gactatgtgt    9180
atcacccact gcaggaggtg aacggggaag cgctgactgc agagaaggag cacatggagg    9240
aaactagcaa cccttcaag gactgaagag ctgccccaac ggcatgctcc agataatctt     9300
gtccctgctc ctcacttcca caggggacat tgtgaggcca ctggcatgga tgctatgcac    9360
cccacccttt gctggccata ttcctcctgt ccccatgctg tggctcatgc caacctagca    9420
ataaggagct ctggagagcc tgcacctgcc tcccgctcgc ctatatctgc tgcccagagg    9480
cctgtctcgc acagggtct cgccactgcc aaagactccc aggaagtcaa agactcccag     9540
taatccacta gcaaatggaa ctctgtaacg ccatcataac aagagtggcc actctccgcg    9600
tgcacaggta tgaaatataa atccttacac acacacacac acacccctc ggctcagcca     9660 cggcactcgc cttttataca gcgtcatcgc tggacagcca actagaactc tgcatcctgt    9720
cacaggaagc acctcataag aaggaatggg gagggaaggc agtcgccttg ttttcagacc    9780
ttagccgaat tc                                                        9792
```

<210> SEQ ID NO 15
<211> LENGTH: 908
<212> TYPE: PRT
<213> ORGANISM: Mus musculus

<400> SEQUENCE: 15

```
Met Leu Phe Lys Leu Leu Gln Arg Gln Thr Tyr Thr Cys Leu Ser His
1               5                   10                  15

Arg Tyr Gly Leu Tyr Val Cys Phe Val Gly Val Val Thr Ile Val
            20                  25                  30

Ser Ala Phe Gln Phe Gly Glu Val Leu Glu Trp Ser Arg Asp Gln
        35                  40                  45

Tyr His Val Leu Phe Asp Ser Tyr Arg Asp Asn Ile Ala Gly Lys Ser
    50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
                85                  90                  95

Arg Glu His Met Glu Glu Glu Gln Arg Ala Met Arg Glu Thr Leu Gly
            100                 105                 110

Lys Asn Thr Thr Glu Pro Thr Lys Lys Ser Glu Lys Gln Leu Glu Cys
        115                 120                 125

Leu Leu Thr His Cys Ile Lys Val Pro Met Leu Val Leu Asp Pro Ala
    130                 135                 140

Leu Pro Ala Thr Ile Thr Leu Lys Asp Leu Pro Thr Leu Tyr Pro Ser
145                 150                 155                 160

Phe His Ala Ser Ser Asp Met Phe Asn Val Ala Lys Pro Lys Asn Pro
                165                 170                 175

Ser Thr Asn Val Pro Val Val Phe Asp Thr Thr Lys Asp Val Glu
            180                 185                 190

Asp Ala His Ala Gly Pro Phe Lys Gly Gly Gln Gln Thr Asp Val Trp
        195                 200                 205

Arg Ala Tyr Leu Thr Thr Asp Lys Asp Ala Pro Gly Leu Val Leu Ile
    210                 215                 220

Gln Gly Leu Ala Phe Leu Ser Gly Phe Pro Pro Thr Phe Lys Glu Thr
225                 230                 235                 240

Ser Gln Leu Lys Thr Lys Leu Pro Arg Lys Ala Phe Pro Leu Lys Ile
```

-continued

```
                245                 250                 255
Lys Leu Leu Arg Leu Tyr Ser Glu Ala Ser Val Ala Leu Leu Lys Leu
                    260                 265                 270

Asn Asn Pro Lys Gly Phe Gln Glu Leu Asn Lys Gln Thr Lys Lys Asn
            275                 280                 285

Met Thr Ile Asp Gly Lys Glu Leu Thr Ile Ser Pro Ala Tyr Leu Leu
    290                 295                 300

Trp Asp Leu Ser Ala Ile Ser Gln Ser Lys Gln Asp Glu Asp Ala Ser
305                 310                 315                 320

Ala Ser Arg Phe Glu Asp Asn Glu Glu Leu Arg Tyr Ser Leu Arg Ser
                325                 330                 335

Ile Glu Arg His Ala Pro Trp Val Arg Asn Ile Phe Ile Val Thr Asn
            340                 345                 350

Gly Gln Ile Pro Ser Trp Leu Asn Leu Asp Asn Pro Arg Val Thr Ile
        355                 360                 365

Val Thr His Gln Asp Ile Phe Gln Asn Leu Ser His Leu Pro Thr Phe
    370                 375                 380

Ser Ser Pro Ala Ile Glu Ser His Ile His Arg Ile Glu Gly Leu Ser
385                 390                 395                 400

Gln Lys Phe Ile Tyr Leu Asn Asp Asp Val Met Phe Gly Lys Asp Val
                405                 410                 415

Trp Pro Asp Asp Phe Tyr Ser His Ser Lys Gly Gln Lys Val Tyr Leu
            420                 425                 430

Thr Trp Pro Val Pro Asn Cys Ala Glu Gly Cys Pro Gly Ser Trp Ile
        435                 440                 445

Lys Asp Gly Tyr Cys Asp Lys Ala Cys Asn Thr Ser Pro Cys Asp Trp
    450                 455                 460

Asp Gly Gly Asn Cys Ser Gly Asn Thr Ala Gly Asn Arg Phe Val Ala
465                 470                 475                 480

Arg Gly Gly Gly Thr Gly Asn Ile Gly Ala Gly Gln His Trp Gln Phe
                485                 490                 495

Gly Gly Gly Ile Asn Thr Ile Ser Tyr Cys Asn Gln Gly Cys Ala Asn
            500                 505                 510

Ser Trp Leu Ala Asp Lys Phe Cys Asp Gln Ala Cys Asn Val Leu Ser
        515                 520                 525

Cys Gly Phe Asp Ala Gly Asp Cys Gly Gln Asp His Phe His Glu Leu
    530                 535                 540

Tyr Lys Val Thr Leu Leu Pro Asn Gln Thr His Tyr Val Val Pro Lys
545                 550                 555                 560

Gly Glu Tyr Leu Ser Tyr Phe Ser Phe Ala Asn Ile Ala Arg Lys Arg
                565                 570                 575

Ile Glu Gly Thr Tyr Ser Asp Asn Pro Ile Ile Arg His Ala Ser Ile
            580                 585                 590

Ala Asn Lys Trp Lys Thr Leu His Leu Ile Met Pro Gly Gly Met Asn
        595                 600                 605

Ala Thr Thr Ile Tyr Phe Asn Leu Thr Leu Gln Asn Ala Asn Asp Glu
    610                 615                 620

Glu Phe Lys Ile Gln Ile Ala Val Glu Val Asp Thr Arg Glu Ala Pro
625                 630                 635                 640

Lys Leu Asn Ser Thr Thr Gln Lys Ala Tyr Glu Ser Leu Val Ser Pro
                645                 650                 655

Val Thr Pro Leu Pro Gln Ala Asp Val Pro Phe Glu Asp Val Pro Lys
            660                 665                 670
```

```
Glu Lys Arg Phe Pro Lys Ile Arg Arg His Asp Val Asn Ala Thr Gly
            675                 680                 685
Arg Phe Gln Glu Glu Val Lys Ile Pro Arg Val Asn Ile Ser Leu Leu
        690                 695                 700
Pro Lys Glu Ala Gln Val Arg Leu Ser Asn Leu Asp Leu Gln Leu Glu
705                 710                 715                 720
Arg Gly Asp Ile Thr Leu Lys Gly Tyr Asn Leu Ser Lys Ser Ala Leu
                    725                 730                 735
Leu Arg Ser Phe Leu Gly Asn Ser Leu Asp Thr Lys Ile Lys Pro Gln
                740                 745                 750
Ala Arg Thr Asp Glu Thr Lys Gly Asn Leu Glu Val Pro Gln Glu Asn
            755                 760                 765
Pro Ser His Arg Arg Pro His Gly Phe Ala Gly Glu His Arg Ser Glu
770                 775                 780
Arg Trp Thr Ala Pro Ala Glu Thr Val Thr Val Lys Gly Arg Asp His
785                 790                 795                 800
Ala Leu Asn Pro Pro Val Leu Glu Thr Asn Ala Arg Leu Ala Gln
                805                 810                 815
Pro Thr Leu Gly Val Thr Val Ser Lys Glu Asn Leu Ser Pro Leu Ile
                820                 825                 830
Val Pro Pro Glu Ser His Leu Pro Lys Glu Glu Ser Asp Arg Ala
            835                 840                 845
Glu Gly Asn Ala Val Pro Val Lys Glu Leu Val Pro Gly Arg Arg Leu
            850                 855                 860
Gln Gln Asn Tyr Pro Gly Phe Leu Pro Trp Glu Lys Lys Tyr Phe
865                 870                 875                 880
Gln Asp Leu Leu Asp Glu Glu Glu Ser Leu Lys Thr Gln Leu Ala Tyr
                885                 890                 895
Phe Thr Asp Arg Lys His Thr Gly Arg Gln Leu Lys
            900                 905

<210> SEQ ID NO 16
<211> LENGTH: 5229
<212> TYPE: DNA
<213> ORGANISM: Mus musculus

<400> SEQUENCE: 16
ggcggtgaag gggtgatgct gttcaagctc ctgcagagac agacctatac ctgcctatcc     60
cacaggtatg ggctctacgt ctgcttcgtg ggcgtcgttg tcaccatcgt ctcggctttc    120
cagttcggag aggtggttct ggaatggagc gagatcagt accatgtttt gtttgattcc    180
tacagagaca acattgctgg gaaatccttt cagaatcggc tctgtctgcc catgccaatc    240
gacgtggttt acacctgggt gaatggcact gaccttgaac tgctaaagga gctacagcag    300
gtccgagagc acatggagga gagcagaga gccatgcggg aaaccctcgg gaagaacaca    360
accgaaccga caagaagag tgagaagcag ctggaatgtc tgctgacgca ctgcattaag    420
gtgcccatgc ttgttctgga cccggccctg ccagccacca tcaccctgaa ggatctgcca    480
acccttacc catctttcca cgcgtccagc gacatgttca atgttgcgaa accaaaaaat    540
ccgtctacaa atgtccccgt tgtcgttttt gacactacta aggatgttga agacgcccat    600
gctggaccgt ttaagggagg ccagcaaaca gatgtttgga gagcctactt gacaacagac    660
aaagacgccc ctggcttagt gctgatacaa ggcttggcgt tcctgagtgg attcccaccg    720
accttcaagg agacgagtca actgaagaca agctgccaa gaaaagcttt ccctctaaaa    780
```

```
ataaagctgt tgcggctgta ctcggaggcc agtgtcgctc ttctgaaatt gaataatccc    840
aagggtttcc aagagctgaa caagcagacc aagaagaaca tgaccatcga tgggaaggaa    900
ctgaccatca gccctgcgta tctgctgtgg gacctgagtg ccatcagcca gtccaagcag    960
gatgaggacg cgtctgccag ccgctttgag gataatgaag agctgaggta ctcgctgcga   1020
tctatcgaga gacacgcgcc atgggtacgg aatattttca ttgtcaccaa cgggcagatt   1080
ccatcctggc tgaaccttga caaccctcga gtgaccatag tgaccaccac ggacattttc   1140
caaaatctga gccacttgcc tactttcagt tcccctgcta ttgaaagtca cattcaccgc   1200
atcgaagggc tgtcccagaa gtttatttat ctaaatgacg atgtcatgtt cggtaaggac   1260
gtctggccga acgattttta cagccactcc aaaggtcaaa aggtttattt gacatggcct   1320
gtgccaaact gtgcagaggg ctgcccgggc tcctggataa aggacggcta ttgtgataag   1380
gcctgtaata cctcaccctg tgactgggat ggcggaaact gctctggtaa tactgcaggg   1440
aaccggtttg ttgcaagagg tgggggtacc gggaatattg gagctggaca gcactggcag   1500
tttggtggag gaataaacac catctcttac tgtaaccaag gatgtgcaaa ctcctggctg   1560
gctgacaagt tctgtgacca agcctgtaac gtcttatcct gcgggtttga tgctggtgac   1620
tgtggacaag atcattttca tgaattgtat aaagtaacac ttctcccaaa ccagactcac   1680
tatgttgtcc ccaaaggtga atacctgtct tatttcagct ttgcaaacat agccagaaaa   1740
agaattgaag ggacctacag cgacaacccc atcatccgcc acgcgtccat tgcaaacaag   1800
tggaaaaccc tacacctgat aatgcccggg gggatgaacg ccaccacgat ctattttaac   1860
ctcactcttc aaaacgccaa cgacgaagag ttcaagatcc agatagcagt agaggtggac   1920
acgagggagg cgcccaaact gaattctaca acccagaagg cctatgaaag tttggttagc   1980
ccagtgacac ctcttcctca ggctgacgtc ccttttgaag atgtccccaa agagaaacgc   2040
ttccccaaga tcaggagaca tgatgtaaat gcaacaggga gattccaaga ggaggtgaaa   2100
atcccccggg taaatatttc actccttccc aaagaggccc aggtgaggct gagcaacttg   2160
gatttgcaac tagaacgtgg agacatcact ctgaaaggat ataacttgtc caagtcagcc   2220
ctgctaaggt ctttcctggg gaattcacta gatactaaaa taaaacctca agctaggacc   2280
gatgaaacaa aaggcaacct ggaggtccca caggaaaacc cttctcacag acgtccacat   2340
ggctttgctg gtgaacacag atcagagaga tggactgccc cagcagagac agtgaccgtg   2400
aaaggccgtg accacgcttt gaatccaccc ccggtgttgg agaccaatgc aagattggcc   2460
cagcctacac taggcgtgac tgtgtccaaa gagaaccttt caccgctgat cgttccccca   2520
gaaagccact tgccaaaaga agaggagagt gacagggcag aaggcaatgc tgtacctgta   2580
aaggagttag tgcctggcag acggttgcag cagaattatc caggcttttt gccctgggag   2640
aaaaaaaagt atttccaaga ccttcttgat gaggaagagt cattgaagac ccagttggcg   2700
tactttacag accgcaaaca taccgggagg caactaaaag atacatttgc agactccctc   2760
cgatacgtca ataaaattct caacagcaag tttggattca catccaggaa agtccctgca   2820
cacatgccgc acatgattga caggatcgtt atgcaagaac tccaagatat gttccctgaa   2880
gaatttgaca agacttcatt tcacaaggtg cgtcactctg aggacatgca gtttgccttc   2940
tcctactttt attacctcat gagtgcagtt cagcccctca atatttccca agtctttcat   3000
gaagtagaca cagaccaatc tggtgtcttg tctgatagggg aaatccgaac wctggccacg   3060
agaattcacg acctaccttt aagcttgcag gatttgacag gtttggaaca catgttaata   3120
```

-continued

```
aattgctcaa aaatgctccc cgctaatatc actcaactca acaacatccc accgactcag    3180
gaagcatact acgaccccaa cctgcctccg gtcactaaga gtcttgtcac caactgtaag    3240
ccagtaactg acaagatcca caaagcctat aaagacaaga acaaatacag gtttgaaatc    3300
atgggagagg aagaaatcgc tttcaagatg atacgaacca atgtttctca tgtggttggt    3360
cagttggatg acatcagaaa aaaccccagg aagttcgttt gtctgaatga caacattgac    3420
cacaaccata aagatgcccg gacagtgaag gctgtcctca gggacttcta tgagtccatg    3480
tttcccatac cttcccagtt tgagctgcca agagagtatc ggaaccgctt tctgcacatg    3540
catgagctcc aagaatggcg ggcatatcga gacaagctga agttttggac ccactgcgta    3600
ctagcaacgt tgattatatt tactatattc tcattttttg ctgaacagat aattgctctg    3660
aagcgaaaga tatttcccag gaggaggata cacaaagaag ctagtccaga ccgaatcagg    3720
gtgtagaaga tcttcatttg aaagtcacct accttagcat ctgtgaacat ctccctcctc    3780
gacaccacag cggagtccct gtgatgtggc acagaggcag cctcgtgggg agaagggaca    3840
tcgtgcagac cgggttcttc tgcaatggga agagagccca ctgacctgga attattcagc    3900
acactaagaa cctgtgtcaa tagcttgtac agcttgtact tttaaaggat ttgccgaagg    3960
acctgtcggc ttgttgacaa accctccctg acaagctgct ggtttcttcc cccagttact    4020
gcagactgag aaaccagtcc atcttgaaag caagtgcgga ggggccccag tctttgcatt    4080
ccaaagcttt ccagcataat ttctggcttg tctcctcctt tgatccattt cccattttt     4140 tttaaaaaac aataagtggc tactaagtta gtcattctca cttctcaaaa taacaaatca    4200
ggatgtcaaa acatttgtat agatcttatt taaataatat agaacgatta cttctttagc    4260
ctatctaaat tattgatttt tattaacagt caagtggtct tgaaccgcta acaactactg    4320
aagagctcga gattgacgtt gaaagtgctt tgagcttgtt taactcattc cccaagaata    4380
ctgtgacctc gtgtgcgggc ctgattgcga agggctagtg tcacgtagca gtgctgctca    4440
ccggatgtaa ttatgtcgtg gaaatgtaca tacagacaaa agtgcctcac ttcagaaatg    4500
agtagtgctg atggcaccag cgagtgatgg tgtccatttg gaaacccatg ataccttcca    4560
atgcccaccc tgcttacttt atacagagca ggggttaacc aacttctgtc aaagaacagt    4620
aaagaacttg agatacatcc atctttgtca aatagttttc cttgctaaca tttattattg    4680
ttggtgtttt gggaggttta ttttatttta ttgctttgtt attttttcaag acggggattc    4740 tctgtgtagc tctggctgtt tggtaattca ctctaaagac caggctggcc ttgaacttag    4800
agattcacct gcttctgctt cctgaatggt aggacatgtg cccacattgc ctacccaccc    4860
cccttttggg ggggtgagc aactcaataa aaagatgaaa acctgcttta gtttgcagct     4920
atacaaaagc agcaggcctc agccagactt gaccccggg gccattgttg cccacggga      4980 gaatcatttt tgacgtgggt aagcaaaccc tgatattggt catgctgtgt tatgtcatta    5040
tgtggtggtt ttgaattttg gaagatattt tcagtcatga tttcagtagt attcctccaa    5100
aatggcacac attttgtaa taagaacttg aaatgtaaat attgtgtttg tgctgtaaat     5160
tttgtgtatt tcaaaaactg aagtttcata aaaaacaca cttattggaa aaaaaaaaa     5220 aaaaaaaa                                                            5229
```

<210> SEQ ID NO 17
<211> LENGTH: 1105
<212> TYPE: DNA
<213> ORGANISM: Drosophila melanogaster
<220> FEATURE:
<221> NAME/KEY: misc_feature

```
<222> LOCATION: (903)..(903)
<223> OTHER INFORMATION: n is a, g, c, or t
<221> NAME/KEY: misc_feature
<222> LOCATION: (935)..(935)
<223> OTHER INFORMATION: n is a, g, c, or t
<221> NAME/KEY: misc_feature
<222> LOCATION: (1023)..(1023)
<223> OTHER INFORMATION: n is a, g, c, or t
<221> NAME/KEY: misc_feature
<222> LOCATION: (1035)..(1035)
<223> OTHER INFORMATION: n is a, g, c, or t
<221> NAME/KEY: misc_feature
<222> LOCATION: (1071)..(1071)
<223> OTHER INFORMATION: n is a, g, c, or t
<221> NAME/KEY: misc_feature
<222> LOCATION: (1100)..(1100)
<223> OTHER INFORMATION: n is a, g, c, or t

<400> SEQUENCE: 17
ctgcaggaat tcggcacgag gcggttcgat gacaagaatg agctgcggta ctctctgagg      60
tccctggaaa aacacgccgc atggatcagg catgtgtaca tagtaaccaa tggccagatt     120
ccaagttggc tggatctcag ctacgaaagg gtcacggtgg tgccccacga agtcctggct     180
cccgatcccg accagctgcc caccttctcc agctcggcca tcgagacatt tctgcaccgc     240
ataccaaagc tgtccaagag gttcctctac ctcaacgacg acatattcct gggagctccg     300
ctgtatccga aggacttgta cactgaagcg gagggagttc gcgtgtacca ggcatggatg     360
gtgcccggct cgcgccttga ttgccccctg acgtacatag gtgatggagc ttgcgatcgg     420
cactgcaaca ttgatgcgtg ccaatttgat ggaggcgact gcagtgaaac tgggccagcg     480
agcgatgccc acgtcattcc accaagcaaa gaagtgctcg aggtgcagcc tgccgctgtt     540
ccacaatcaa gagtccaccg atttcctcag atgggtctcc aaaagctgtt caggcgcagc     600
tctgccaatt ttaaggatgt tatgcggcac cgcaatgtgt ccacactcaa ggaactacgt     660
cgcattgtgg agcgttttaa caaggccaaa ctcatgtcgc tgaacccga actggagacc      720
tccagctccg agccacagac aactcagcgc cacgggctgc gcaaggagga ttttaagtct     780
tccaccgata tttactctca ctcgctgatt gccaccaata tgttgctgaa tagagcctat     840
ggctttaagg cacgccatgt cctggcgcac gtgggcttcc taattgacaa ggatattgtg     900
gangccatgc aacgacgttt taccagcgaa ttctngacac tggccattaa cgctttccga     960
gccccaacag atttgcagta cgcattcgct tactacttct ttctaatgag cgaaatccaa    1020
gtnatgagtg tagangaaat cttcgatgaa gtcgacaccg acggtttgg ncacctggtc    1080
ggatccagaa gtgcgaaccn tttta                                          1105

<210> SEQ ID NO 18
<211> LENGTH: 2005
<212> TYPE: DNA
<213> ORGANISM: Mus musculus

<400> SEQUENCE: 18
gtttcccgcg acgatgacct gctgctgcct tacccactag cgcgcagacg tccctcgcga      60
gactgcgccc gggtgcgctc aggtagccca gagcaggaga gctggcctcc gccacctctg     120
gccacccacg aaccccgggc gccaagccac cacgcggccg tgcgcacctt cgtgtcgcac     180
ttcgaggggc gcgcggtggc cggccacctg acgcgggtcg ccgatccct acgcactttc     240
tcggtgctgg agcccggagg agccggggc tgcggcggca aagcgccgc ggctactgtg     300
gaggacacag ccgtccgggc cggttgccgc atcgctcaga acgtggcttt cttccgcatg     360
agcactggcg agtgcttggg gaacgtggtg agcgacgggc ggctggtgag cagctcaggg     420
```

-continued

```
ggactgcaga acgcgcagtt cggtatccga cgcgatggaa ccatagtcac cgggtcctgt      480
cttgaagaag aggttctgga tcccgtgaat ccgttcgtgc agctgctgag cggagtcgtg      540
tggctcatcc gcaatggaaa catctacatc aacgagagcc aagccatcga gtgtgacgag      600
acacaggaga caggttcttt tagcaaattt gtgaatgtga tgtcagccag gacagccgtg      660
ggtcatgacc gtgaggggca gcttatcctc ttccatgctg atggacagac ggaacagcgt      720
ggccttaacc tatgggagat ggcagagttc ctgcgtcaac aagatgtcgt caatgccatc      780
aacctggatg gaggcggttc tgctactttt gtgctcaatg gaccctggc cagttaccct       840
tcagatcact gccaggacaa catgtggcgc tgtccccgcc aagtgtccac tgtggtgtgt      900
gtgcatgaac cgcgctgcca gccacccgac tgcagtggcc atgggacctg tgtggatggc      960
cactgtgaat gcaccagcca cttctggcgg ggcgaggcct gcagcgagct ggactgtggc     1020
ccctccaact gcagccagca tgggctgtgc acagctggct gccactgtga tgctgggtgg     1080
acaggatcca actgcagtga agagtgtcct ctgggctggt atgggccagg ttgccagagg     1140
ccctgccagt gtgagcacca gtgtttctgt gacccgcaga ctggcaactg cagcatctcc     1200
caagtgaggc agtgtctcca gccaactgag gctacgccga gggcaggaga gctggcctct     1260
ttcaccagga ccacctggct agccctcacc ctgacactaa ttttcctgct gctgatcagc     1320
actggggtca acgtgtcctt gttcctgggc tccagggccg agaggaaccg gcacctcgac     1380
ggggactatg tgtatcaccc actgcaggag gtgaacgggg aagcgctgac tgcagagaag     1440
gagcacatgg aggaaactag caaccccttc aaggactgaa gagctgcccc aacggcatgc     1500
tccagataat cttgtccctg ctcctcactt ccacagggga cattgtgagg ccactggcat     1560
ggatgctatg caccccaccc tttgctggcc atattcctcc tgtccccatg ctgtggctca     1620
tgccaaccta gcaataagga gctctggaga gcctgcacct gcctcccgct cgcctatatc     1680
tgctgcccag aggcctgtct cgcacagggg tctcgccact gccaaagact cccaggaagt     1740
caaagactcc cagtaatcca ctagcaaatg gaactctgta acgccatcat aacaagagtg     1800
gccactctcc gcgtgcacag gtatgaaata taaatcctta cacacacaca cacacacacc     1860
ctcggctcag ccacggcact cgccttttat acagcgtcat cgctggacag ccaactagaa     1920
ctctgcatcc tgtcacagga agcacctcat aagaaggaat ggggagggaa ggcagtcgcc     1980
ttgttttcag accttagccg aattc                                           2005
```

<210> SEQ ID NO 19
<211> LENGTH: 492
<212> TYPE: PRT
<213> ORGANISM: Mus musculus

<400> SEQUENCE: 19

Val Ser Arg Asp Asp Leu Leu Pro Tyr Pro Leu Ala Arg Arg
1               5                   10                  15

Arg Pro Ser Arg Asp Cys Ala Arg Val Arg Ser Gly Ser Pro Glu Gln
            20                  25                  30

Glu Ser Trp Pro Pro Pro Leu Ala Thr His Glu Pro Arg Ala Pro
        35                  40                  45

Ser His His Ala Ala Val Arg Thr Phe Val Ser His Phe Glu Gly Arg
    50                  55                  60

Ala Val Ala Gly His Leu Thr Arg Val Ala Asp Pro Leu Arg Thr Phe
65                  70                  75                  80

Ser Val Leu Glu Pro Gly Gly Ala Gly Gly Cys Gly Gly Arg Ser Ala

```
              85                  90                  95
Ala Ala Thr Val Glu Asp Thr Ala Val Arg Ala Gly Cys Arg Ile Ala
            100                 105                 110

Gln Asn Gly Gly Phe Phe Arg Met Ser Thr Gly Glu Cys Leu Gly Asn
            115                 120                 125

Val Val Ser Asp Gly Arg Leu Val Ser Ser Gly Gly Leu Gln Asn
            130                 135                 140

Ala Gln Phe Gly Ile Arg Arg Asp Gly Thr Ile Val Thr Gly Ser Cys
145                 150                 155                 160

Leu Glu Glu Glu Val Leu Asp Pro Val Asn Pro Phe Val Gln Leu Leu
                165                 170                 175

Ser Gly Val Val Trp Leu Ile Arg Asn Gly Asn Ile Tyr Ile Asn Glu
            180                 185                 190

Ser Gln Ala Ile Glu Cys Asp Glu Thr Gln Glu Thr Gly Ser Phe Ser
            195                 200                 205

Lys Phe Val Asn Val Met Ser Ala Arg Thr Ala Val Gly His Asp Arg
            210                 215                 220

Glu Gly Gln Leu Ile Leu Phe His Ala Asp Gly Gln Thr Glu Gln Arg
225                 230                 235                 240

Gly Leu Asn Leu Trp Glu Met Ala Glu Phe Leu Arg Gln Gln Asp Val
                245                 250                 255

Val Asn Ala Ile Asn Leu Asp Gly Gly Gly Ser Ala Thr Phe Val Leu
            260                 265                 270

Asn Gly Thr Leu Ala Ser Tyr Pro Ser Asp His Cys Gln Asp Asn Met
            275                 280                 285

Trp Arg Cys Pro Arg Gln Val Ser Thr Val Val Cys Val His Glu Pro
            290                 295                 300

Arg Cys Gln Pro Pro Asp Cys Ser Gly His Gly Thr Cys Val Asp Gly
305                 310                 315                 320

His Cys Glu Cys Thr Ser His Phe Trp Arg Gly Glu Ala Cys Ser Glu
                325                 330                 335

Leu Asp Cys Gly Pro Ser Asn Cys Ser Gln His Gly Leu Cys Thr Ala
                340                 345                 350

Gly Cys His Cys Asp Ala Gly Trp Thr Gly Ser Asn Cys Ser Glu Glu
            355                 360                 365

Cys Pro Leu Gly Trp Tyr Gly Pro Gly Cys Gln Arg Pro Cys Gln Cys
370                 375                 380

Glu His Gln Cys Phe Cys Asp Pro Gln Thr Gly Asn Cys Ser Ile Ser
385                 390                 395                 400

Gln Val Arg Gln Cys Leu Gln Pro Thr Glu Ala Thr Pro Arg Ala Gly
                405                 410                 415

Glu Leu Ala Ser Phe Thr Arg Thr Thr Trp Leu Ala Leu Thr Leu Thr
            420                 425                 430

Leu Ile Phe Leu Leu Leu Ile Ser Thr Gly Val Asn Val Ser Leu Phe
            435                 440                 445

Leu Gly Ser Arg Ala Glu Arg Asn Arg His Leu Asp Gly Asp Tyr Val
450                 455                 460

Tyr His Pro Leu Gln Glu Val Asn Gly Glu Ala Leu Thr Ala Glu Lys
465                 470                 475                 480

Glu His Met Glu Glu Thr Ser Asn Pro Phe Lys Asp
                485                 490

<210> SEQ ID NO 20
```

<211> LENGTH: 3783
<212> TYPE: DNA
<213> ORGANISM: Homo sapiens

<400> SEQUENCE: 20

| | | | | | |
|---|---|---|---|---|---|
| gccaccatgg | ggttcaagct | cttgcagaga | caaacctata | cctgcctgtc | ccacaggtat | 60 |
| gggctctacg | tgtgcttctt | gggcgtcgtt | gtcaccatcg | tctccgcctt | ccagttcgga | 120 |
| gaggtggttc | tggaatggag | ccgagatcaa | taccatgttt | tgtttgattc | ctatagagac | 180 |
| aatattgctg | gaaagtcctt | tcagaatcgg | ctttgtctgc | ccatgccgat | tgacgttgtt | 240 |
| tacacctggg | tgaatggcac | agatcttgaa | ctactgaagg | aactacagca | ggtcagagaa | 300 |
| cagatggagg | aggagcagaa | agcaatgaga | gaaatccttg | ggaaaaacac | aacggaacct | 360 |
| actaagaaga | gtgagaagca | gttagagtgt | ttgctaacac | actgcattaa | ggtgccaatg | 420 |
| cttgtcctgg | acccagccct | gccagccaac | atcaccctga | aggacctgcc | atctctttat | 480 |
| ccttcttttc | attctgccag | tgacattttc | aatgttgcaa | aaccaaaaaa | cccttctacc | 540 |
| aatgtctcag | ttgttgtttt | tgacagtact | aaggatgttg | aagatgccca | ctctggactg | 600 |
| cttaaaggaa | atagcagaca | gacagtatgg | agggctact | tgacaacaga | taagaagtc | 660 |
| cctggattag | tgctaatgca | agatttggct | ttcctgagtg | gatttccacc | aacattcaag | 720 |
| gaaacaaatc | aactaaaaac | aaaattgcca | gaaaatcttt | cctctaaagt | caaactgttg | 780 |
| cagttgtatt | cagaggccag | tgtagcgctt | ctaaaactga | ataacccaa | ggattttcaa | 840 |
| gaattgaata | agcaaactaa | gaagaacatg | accattgatg | gaaaagaact | gaccataagt | 900 |
| cctgcatatt | tattatggga | tctgagcgcc | atcagccagt | ctaagcagga | tgaagacatc | 960 |
| tctgccagtc | gttttgaaga | taacgaagaa | ctgaggtact | cattgcgatc | tatcgagagg | 1020 |
| catgcaccat | gggttcggaa | tatttcatt | gtcaccaacg | ggcagattcc | atcctggctg | 1080 |
| aaccttgaca | tcctcgagt | gacaatagta | acacaccagg | atgttttcg | aaatttgagc | 1140 |
| cacttgccta | cctttagttc | acctgctatt | gaaagtcacg | ttcatcgcat | cgaagggctg | 1200 |
| tcccagaagt | ttatttacct | aaatgatgat | gtcatgtttg | ggaaggatgt | ctggccagat | 1260 |
| gattttaca | gtcactccaa | aggccagaag | gtttatttga | catggcctgt | gccaaactgt | 1320 |
| gccgagggct | gccaggttc | ctggattaag | gatggctatt | gtgacaaggc | ttgtaataat | 1380 |
| tcagcctgcg | attgggatgg | tggggattgc | tctggaaaca | gtggagggag | tcgctatatt | 1440 |
| gcaggaggtg | gaggtactgg | gagtattgga | gttgacagc | cctggcagtt | tggtggagga | 1500 |
| ataaacagtg | tctcttactg | taatcaggga | tgtgcgaatt | cctggctcgc | tgataagttc | 1560 |
| tgtgaccaag | catgcaatgt | cttgtcctgt | gggtttgatg | ctggcgactg | tgggcaagat | 1620 |
| cattttcatg | aattgtataa | agtgatcctt | ctcccaaacc | agactcacta | tattattcca | 1680 |
| aaaggtgaat | gcctgcctta | tttcagcttt | gcagaagtag | ccaaaagagg | agttgaaggt | 1740 |
| gcctatagtg | acaatccaat | aattcgacat | gcttctattg | ccaacaagtg | gaaaaccatc | 1800 |
| cacctcataa | tgcacagtgg | aatgaatgcc | accacaatac | attttaatct | cacgtttcaa | 1860 |
| aatacaaacg | atgaagagtt | caaaatgcag | ataacagtgg | aggtggacac | aagggaggga | 1920 |
| ccaaaactga | attctacggc | ccagaagggt | tacgaaaatt | tagttagtcc | cataacactt | 1980 |
| cttccagagg | cggaaatcct | ttttgaggat | attcccaaag | aaaaacgctt | cccgaagttt | 2040 |
| aagagacatg | atgttaactc | aacaaggaga | gcccaggaag | aggtgaaaat | tcccctggta | 2100 |
| aatatttcac | tccttccaaa | agacgcccag | ttgagtctca | ataccttgga | tttgcaactg | 2160 |
| gaacatggag | acatcacttt | gaaaggatac | aatttgtcca | agtcagcctt | gctgagatca | 2220 |

-continued

```
tttctgatga actcacagca tgctaaaata aaaaatcaag ctataataac agatgaaaca      2280
aatgacagtt tggtggctcc acaggaaaaa caggttcata aaagcatctt gccaaacagc      2340
ttaggagtgt ctgaaagatt gcagaggttg acttttcctg cagtgagtgt aaaagtgaat      2400
ggtcatgacc agggtcagaa tccacccctg gacttggaga ccacagcaag atttagagtg      2460
gaaactcaca cccaaaaaac cataggcgga aatgtgacaa agaaaagcc cccatctctg      2520 attgttccac tggaaagcca gatgacaaaa gaaaagaaaa tcacagggaa agaaaaagag      2580
aacagtagaa tggaggaaaa tgctgaaaat cacataggcg ttactgaagt gttacttgga      2640
agaaagctgc agcattacac agatagttac ttgggctttt tgccatggga gaaaaaaaag      2700
tatttcctag atcttctcga cgaagaagag tcattgaaga cacaattggc atacttcact      2760
gatagcaaga atactgggag gcaactaaaa gatacatttg cagattccct cagatatgta      2820
aataaaattc taaatagcaa gtttggattc acatcgcgga aagtccctgc tcacatgcct      2880
cacatgattg accggattgt tatgcaagaa ctgcaagata tgttccctga agaatttgac      2940
aagacgtcat ttcacaaagt gcgccattct gaggatatgc agtttgcctt ctcttatttt      3000
tattatctca tgagtgcagt gcagccactg aatatatctc aagtctttga tgaagttgat      3060
acagatcaat ctggtgtctt gtctgacaga gaaatccgaa cactggctac cagaattcac      3120
gaactgccgt taagtttgca ggatttgaca ggtctggaac acatgctaat aaattgctca      3180
aaaatgcttc ctgctgatat cacgcagcta aataatattc caccaactca ggaatcctac      3240
tatgatccca acctgccacc ggtcactaaa agtctagtaa caaactgtaa accagtaact      3300
gacaaaatcc acaaagcata taggacaaa acaaatata ggtttgaaat catgggagaa       3360
gaagaaatcg cttttaaaat gattcgtacc aacgtttctc atgtggttgg ccagttggat      3420
gacataagaa aaaccctag gaagtttgtt tgcctgaatg acaacattga ccacaatcat       3480
aaagatgctc agacagtgaa ggctgttctc agggacttct atgaatccat gttccccata      3540
ccttcccaat ttgaactgcc aagagagtat cgaaaccgtt tccttcatat gcatgagctg      3600
caggaatgga gggcttatcg agacaaattg aagttttgga cccattgtgt actagcaaca      3660
ttgattatgt ttactatatt ctcatttttt gctgagcagt taattgcact taagcggaag      3720
atatttccca gaaggaggat acacaaagaa gctagtccca atcgaatcag agtatagaag      3780
atc                                                                   3783
```

<210> SEQ ID NO 21
<211> LENGTH: 3621
<212> TYPE: DNA
<213> ORGANISM: Homo sapiens

<400> SEQUENCE: 21

```
ctagccgcca ccatggagac agacacactc ctgctatggg tactgctgct ctggttccca       60
ggttccactg gtgacgaaga tcaggtagat ccgcggttaa tcgacggtaa gcttagccga      120
gatcaatacc atgttttgtt tgattcctat agagacaata ttgctggaaa gtcctttcag      180
aatcggcttt gtctgcccat gccgattgac gttgtttaca cctgggtgaa tggcacagat      240
cttgaactac tgaaggaact acagcaggtc agagaacaga tggaggagga gcagaaagca      300
atgagagaaa tccttgggaa aaacacaacg gaacctacta agaagagtga agcagttta       360 gagtgtttgc taacacactg cattaaggtg ccaatgcttg tcctggaccc agccctgcca      420
gccaacatca ccctgaagga cctgccatct ctttatcctt cttttcattc tgccagtgac      480
```

-continued

```
attttcaatg ttgcaaaacc aaaaaaccct tctaccaatg tctcagttgt tgtttttgac      540
agtactaagg atgttgaaga tgcccactct ggactgctta aaggaaatag cagacagaca      600
gtatggaggg gctacttgac aacagataaa gaagtccctg gattagtgct aatgcaagat      660
ttggctttcc tgagtggatt tccaccaaca ttcaaggaaa caaatcaact aaaaacaaaa      720
ttgccagaaa atctttcctc taaagtcaaa ctgttgcagt tgtattcaga ggccagtgta      780
gcgcttctaa aactgaataa ccccaaggat tttcaagaat tgaataagca aactaagaag      840
aacatgacca ttgatggaaa agaactgacc ataagtcctg catatttatt atgggatctg      900
agcgccatca gccagtctaa gcaggatgaa gacatctctg ccagtcgttt tgaagataac      960
gaagaactga ggtactcatt gcgatctatc gagaggcatg caccatgggt tcggaatatt     1020
ttcattgtca ccaacgggca gattccatcc tggctgaacc ttgacaatcc tcgagtgaca     1080
atagtaacac accaggatgt tttcgaaatt tgagccact tgcctacctt tagttcacct      1140
gctattgaaa gtcacgttca tcgcatcgaa gggctgtccc agaagtttat ttacctaaat     1200
gatgatgtca tgtttgggaa ggatgtctgg ccagatgatt tttacagtca ctccaaaggc     1260
cagaaggttt atttgacatg gcctgtgcca aactgtgccg agggctgccc aggttcctgg     1320
attaaggatg gctattgtga caaggcttgt aataattcag cctgcgattg ggatggtggg     1380
gattgctctg gaaacagtgg agggagtcgc tatattgcag gaggtggagg tactgggagt     1440
attggagttg gacagccctg gcagtttggt ggaggaataa acagtgtctc ttactgtaat     1500
cagggatgtg cgaattcctg gctcgctgat aagttctgtg accaagcatg caatgtcttg     1560
tcctgtgggt ttgatgctgg cgactgtggg caagatcatt ttcatgaatt gtataaagtg     1620
atccttctcc caaaccagac tcactatatt attccaaaag gtgaatgcct gccttatttc     1680
agctttgcag aagtagccaa agaggagtt gaaggtgcct atagtgacaa tccaataatt      1740
cgacatgctt ctattgccaa caagtggaaa accatccacc tcataatgca cagtggaatg     1800
aatgccacca caatacattt taatctcacg tttcaaaata caaacgatga agagttcaaa     1860
atgcagataa cagtggaggt ggacacaagg gagggaccaa aactgaattc tacggcccag     1920
aagggttacg aaaatttagt tagtcccata acacttcttc cagaggcgga aatccttttt     1980
gaggatattc ccaaagaaaa acgcttcccg aagtttaaga acatgatgt taactcaaca     2040 aggagagccc aggaagaggt gaaaattccc ctggtaaata tttcactcct tccaaaagac     2100
gcccagttga gtctcaatac cttggatttg caactggaac atggagacat cactttgaaa     2160
ggatacaatt tgtccaagtc agccttgctg agatcatttc tgatgaactc acagcatgct     2220 aaaataaaa atcaagctat aataacagat gaaacaaatg acagtttggt ggctccacag     2280
gaaaaacagg ttcataaaag catcttgcca aacagcttag gagtgtctga aagattgcag     2340
aggttgactt ttcctgcagt gagtgtaaaa gtgaatggtc atgaccaggg tcagaatcca     2400
cccctggact tggagaccac agcaagattt agagtggaaa ctcacaccca aaaaaccata     2460
ggcggaaatg tgacaaaaga aaagccccca tctctgattg ttccactgga aagccagatg     2520
acaaaagaaa agaaaatcac agggaaagaa aaagagaaca gtagaatgga ggaaaatgct     2580
gaaaatcaca taggcgttac tgaagtgtta cttggaagaa agctgcagca ttacacagat     2640
agttacttgg gctttttgcc atgggagaaa aaaagtatt tcctagatct tctcgacgaa      2700
gaagagtcat tgaagacaca attggcatac ttcactgata gcaagaatac tgggaggcaa     2760
ctaaaagata catttgcaga ttccctcaga tatgtaaata aaattctaaa tagcaagttt     2820
ggattcacat cgcggaaagt ccctgctcac atgcctcaca tgattgaccg gattgttatg     2880
```

| | | |
|---|---|---|
| caagaactgc aagatatgtt ccctgaagaa tttgacaaga cgtcatttca caaagtgcgc | 2940 |
| cattctgagg atatgcagtt tgccttctct tattttatt atctcatgag tgcagtgcag | 3000 |
| ccactgaata tatctcaagt ctttgatgaa gttgatacag atcaatctgg tgtcttgtct | 3060 |
| gacagagaaa tccgaacact ggctaccaga attcacgaac tgccgttaag tttgcaggat | 3120 |
| ttgacaggtc tggaacacat gctaataaat tgctcaaaaa tgcttcctgc tgatatcacg | 3180 |
| cagctaaata atattccacc aactcaggaa tcctactatg atcccaacct gccaccggtc | 3240 |
| actaaaagtc tagtaacaaa ctgtaaacca gtaactgaca aaatccacaa agcatataag | 3300 |
| gacaaaaaca aatataggtt tgaaatcatg ggagaagaag aaatcgcttt taaaatgatt | 3360 |
| cgtaccaacg tttctcatgt ggttggccag ttggatgaca aagaaaaaa ccctaggaag | 3420 |
| tttgtttgcc tgaatgacaa cattgaccac aatcataaag atgctcagac agtgaaggct | 3480 |
| gttctcaggg acttctatga atccatgttc cccatacctt cccaatttga actgccaaga | 3540 |
| gagtatcgaa accgtttcct tcatatgcat gagctgcagg aatggagggc ttatcgagac | 3600 |
| aaattgaagt agtagtctag a | 3621 |

<210> SEQ ID NO 22
<211> LENGTH: 1383
<212> TYPE: DNA
<213> ORGANISM: Homo sapiens

<400> SEQUENCE: 22

| | | |
|---|---|---|
| atggcgacct ccacgggtcg ctggcttctc ctccggcttg cactattcgg cttcctctgg | 60 |
| gaagcgtccg gcggcctcga ctcggggggcc tcccgcgacg acgacttgct actgccctat | 120 |
| ccacgcgcgc gcgcgcgcct cccccgggac tgcacacggg tgcgcgccgg caaccgcgag | 180 |
| cacgagagtt ggcctccgcc tcccgcgact cccggcgccg gcggtctggc cgtgcgcacc | 240 |
| ttcgtgtcgc acttcaggga ccgcgcggtg gccgccacc tgacgcgggc cgttgagccc | 300 |
| ctgcgcacct tctcggtgct ggagcccggt ggacccggcg gctgcgcggc gagacgacgc | 360 |
| gccaccgtgg aggagacggc gcgggcggcc gactgccgtg tcgcccagaa cggcggcttc | 420 |
| ttccgcatga actcgggcga gtgcctgggg aacgtggtga cgacgagcg gcgggtgagc | 480 |
| agctccgggg ggctgcagaa cgcgcagttc gggatccgcc gcgacgggac cctggtcacc | 540 |
| gggtacctgt ctgaggagga ggtgctggac actgagaacc catttgtgca gctgctgagt | 600 |
| ggggtcgtgt ggctgattcg taatggaagc atctacatca acgagagcca agccacagag | 660 |
| tgtgacgaga cacaggagac aggttccttt agcaaatttg tgaatgtgat atcagccagg | 720 |
| acggccattg gccacgaccg gaaagggcag ctggtgctct ttcatgcaga cggccatacg | 780 |
| gagcagcgtg gcatcaacct gtgggaaatg gcggagttcc tgctgaaaca ggacgtggtc | 840 |
| aacgccatca acctggatgg gggtggctct gccacctttg tgctcaacgg gccttggcc | 900 |
| agttacccgt cagatcactg ccaggacaac atgtggcgct gtccccgcca agtgtccacc | 960 |
| gtggtgtgtg tgcacgaacc ccgctgccag ccgcctgact gccacggcca cgggacctgc | 1020 |
| gtggacgggc actgccaatg caccgggcac ttctggcggg gtccggctg tgatgagctg | 1080 |
| gactgtggcc cctctaactg cagccagcac ggactgtgca cggagaccgg ctgccgctgt | 1140 |
| gatgccggat ggaccgggtc caactgcagt gaagagtgtc cccttggctg gcatgggccg | 1200 |
| ggctgccaga ggccttgtaa gtgtgagcac cattgtccct gtgaccccaa gactggcaac | 1260 |
| tgcagcgtct ccagagtaaa gcagtgtctc cagccacctg aagccaccct gagggcggga | 1320 | gaactctcct ttttcaccag ggaggaccag gtggacccca ggctgatcga cggcaaggat    1380 tga    1383

<210> SEQ ID NO 23
<211> LENGTH: 32
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa is any amino acid

<400> SEQUENCE: 23

Asp Xaa Thr Arg Val His Ala Gly Arg Leu Glu His Glu Ser Trp Pro
1               5                   10                  15

Pro Ala Ala Gln Thr Ala Gly Ala His Arg Pro Ser Val Arg Thr Phe
            20                  25                  30

<210> SEQ ID NO 24
<211> LENGTH: 20
<212> TYPE: PRT
<213> ORGANISM: Bos taurus

<400> SEQUENCE: 24

Arg Asp Gly Thr Leu Val Thr Gly Tyr Leu Ser Glu Glu Val Leu
1               5                   10                  15

Asp Thr Glu Asn
            20

<210> SEQ ID NO 25
<211> LENGTH: 13
<212> TYPE: PRT
<213> ORGANISM: Bos taurus

<400> SEQUENCE: 25

Gly Ile Asn Leu Trp Glu Met Ala Glu Phe Leu Leu Lys
1               5                   10

<210> SEQ ID NO 26
<211> LENGTH: 13
<212> TYPE: PRT
<213> ORGANISM: Bos taurus

<400> SEQUENCE: 26

Met Leu Leu Lys Leu Leu Gln Arg Gln Arg Gln Thr Tyr
1               5                   10

<210> SEQ ID NO 27
<211> LENGTH: 28
<212> TYPE: PRT
<213> ORGANISM: Bos taurus

<400> SEQUENCE: 27

Asp Thr Phe Ala Asp Ser Leu Arg Tyr Val Asn Lys Ile Leu Asn Ser
1               5                   10                  15

Lys Phe Gly Phe Thr Ser Arg Lys Val Pro Ala His
            20                  25

<210> SEQ ID NO 28
<211> LENGTH: 21
<212> TYPE: PRT
<213> ORGANISM: Bos taurus

<400> SEQUENCE: 28

```
Ala Lys Met Lys Val Glu Glu Pro Asn Thr Phe Gly Leu Asn Asn
1               5                   10                  15

Pro Phe Leu Pro Gln
            20

<210> SEQ ID NO 29
<211> LENGTH: 5
<212> TYPE: PRT
<213> ORGANISM: Bos taurus

<400> SEQUENCE: 29

Ile Leu Asn Ser Lys
1               5

<210> SEQ ID NO 30
<211> LENGTH: 5
<212> TYPE: PRT
<213> ORGANISM: Bos taurus

<400> SEQUENCE: 30

Thr Ser Phe His Lys
1               5

<210> SEQ ID NO 31
<211> LENGTH: 6
<212> TYPE: PRT
<213> ORGANISM: Bos taurus

<400> SEQUENCE: 31

Phe Gly Phe Thr Ser Arg
1               5

<210> SEQ ID NO 32
<211> LENGTH: 12
<212> TYPE: PRT
<213> ORGANISM: Bos taurus

<400> SEQUENCE: 32

Ser Leu Val Thr Asn Cys Lys Pro Val Thr Asp Lys
1               5                   10

<210> SEQ ID NO 33
<211> LENGTH: 12
<212> TYPE: PRT
<213> ORGANISM: Bos taurus

<400> SEQUENCE: 33

Leu Ala His Val Ser Glu Pro Ser Thr Cys Val Tyr
1               5                   10

<210> SEQ ID NO 34
<211> LENGTH: 13
<212> TYPE: PRT
<213> ORGANISM: Bos taurus

<400> SEQUENCE: 34

Asn Asn Pro Phe Leu Pro Gln Thr Ser Arg Leu Gln Pro
1               5                   10

<210> SEQ ID NO 35
<211> LENGTH: 17
<212> TYPE: PRT
<213> ORGANISM: Bos taurus
<220> FEATURE:
```

```
<221> NAME/KEY: misc_feature
<222> LOCATION: (8)..(8)
OTHER INFORMATION: Xaa is any amino acid
NAME/KEY: misc_feature
<222> LOCATION: (10)..(10)
<223> OTHER INFORMATION: Xaa is any amino acid
<221> NAME/KEY: misc_feature
<222> LOCATION: (13)..(13)
<223> OTHER INFORMATION: Xaa is any amino acid
<221> NAME/KEY: misc_feature
<222> LOCATION: (15)..(15)
<223> OTHER INFORMATION: Xaa is any amino acid

SEQUENCE: 35

Val Pro Met Leu Val Leu Asp Xaa Ala Xaa Pro Thr Xaa Val Xaa Leu
1               5                   10                  15

Lys

<210> SEQ ID NO 36
<211> LENGTH: 22
<212> TYPE: PRT
<213> ORGANISM: Bos taurus

<400> SEQUENCE: 36

Glu Leu Pro Ser Leu Tyr Pro Ser Phe Leu Ser Ala Ser Asp Val Phe
1               5                   10                  15

Asn Val Ala Lys Pro Lys
            20

<210> SEQ ID NO 37
<211> LENGTH: 25
<212> TYPE: DNA
<213> ORGANISM: Artificial Sequence
<220> FEATURE:
<223> OTHER INFORMATION: synthetic DNA

<400> SEQUENCE: 37
gcgaagatga aggtggtgga ggacc                                    25

<210> SEQ ID NO 38
<211> LENGTH: 24
<212> TYPE: DNA
<213> ORGANISM: Artificial Sequence
<220> FEATURE:
<223> OTHER INFORMATION: synthetic DNA

<400> SEQUENCE: 38
tgcagagaca gacctatacc tgcc                                     24

<210> SEQ ID NO 39
<211> LENGTH: 23
<212> TYPE: DNA
<213> ORGANISM: Artificial Sequence
<220> FEATURE:
<223> OTHER INFORMATION: synthetic DNA

<400> SEQUENCE: 39
actcacctct ccgaactgga aag                                      23

<210> SEQ ID NO 40
<211> LENGTH: 29
<212> TYPE: DNA
<213> ORGANISM: Artificial Sequence
<220> FEATURE:
<223> OTHER INFORMATION: synthetic DNA

<400> SEQUENCE: 40
```

```
ctagccacca tggggttcaa gctcttgca                                    29

<210> SEQ ID NO 41
<211> LENGTH: 21
<212> TYPE: DNA
<213> ORGANISM: Artificial Sequence
<220> FEATURE:
<223> OTHER INFORMATION: synthetic DNA

<400> SEQUENCE: 41
agagcttgaa ccccatggtg g                                            21

<210> SEQ ID NO 42
<211> LENGTH: 60
<212> TYPE: DNA
<213> ORGANISM: Artificial Sequence
<220> FEATURE:
<223> OTHER INFORMATION: synthetic DNA

<400> SEQUENCE: 42
gaagacacaa ttggcatact tcactgatag caagaatact gggaggcaac taaaagatac   60

<210> SEQ ID NO 43
<211> LENGTH: 20
<212> TYPE: DNA
<213> ORGANISM: Artificial Sequence
<220> FEATURE:
<223> OTHER INFORMATION: synthetic DNA

<400> SEQUENCE: 43
actgcatatc ctcagaatgg                                              20

<210> SEQ ID NO 44
<211> LENGTH: 33
<212> TYPE: DNA
<213> ORGANISM: Artificial Sequence
<220> FEATURE:
<223> OTHER INFORMATION: synthetic DNA

<400> SEQUENCE: 44
tggttctgaa gcttagccga gatcaatacc atg                               33

<210> SEQ ID NO 45
<211> LENGTH: 40
<212> TYPE: DNA
<213> ORGANISM: Artificial Sequence
<220> FEATURE:
<223> OTHER INFORMATION: synthetic DNA

<400> SEQUENCE: 45
tagtacactc tagactacta cttcaatttg tctcgataag                        40

<210> SEQ ID NO 46
<211> LENGTH: 218
<212> TYPE: DNA
<213> ORGANISM: hybrid
<220> FEATURE:
<221> NAME/KEY: misc_feature
<223> OTHER INFORMATION: mouse/human hybrid

<400> SEQUENCE: 46
ctagccgcca ccatggagac agacacactc ctgctatggg tactgctgct cggcggtggt   60
acctctgtct gtgtgaggac gatacccatg acgacgagtg ggttccaggt tccactggtg  120
acgaagatca ggtagatccg cggttaatca cccaaggtcc aagtgaccca ctgcttctag  180
```

```
tccatctagg cgccaattag gacggtactg ccattcga                                    218

<210> SEQ ID NO 47
<211> LENGTH: 205
<212> TYPE: DNA
<213> ORGANISM: hybrid
<220> FEATURE:
<221> NAME/KEY: misc_feature
<223> OTHER INFORMATION: mouse/human hybrid

<400> SEQUENCE: 47
ctagcggtac catgagatta gcagtaggcg ccttattagt atgcgcagta ctccgccatg     60
gtactctaat cgtcatccgc ggaataatca tacgcgtcat gagggattat gtctcgcaga    120
agatcaggta gatccgcggt taatcgacgg taccttatac agagcgtctt ctagtccatc    180
taggcgccaa ttagctgcca ttcga                                          205

<210> SEQ ID NO 48
<211> LENGTH: 207
<212> TYPE: DNA
<213> ORGANISM: hybrid
<220> FEATURE:
<221> NAME/KEY: misc_feature
<223> OTHER INFORMATION: mouse/human hybrid

<400> SEQUENCE: 48
ctagccgcca ccatgggatt agcagtaggc gccttattag tatgcgcagt cgccggtggt     60
accctaatcg tcatccgcgg aataatcata cgcgtcaact cggattatgt ctcgcagaag    120
atcaggtaga tccgcggtta atcgacgtga gcctaataca gagcgtcttc tagtccatct    180
aggcgccaat tagctgcgta cattcga                                        207

<210> SEQ ID NO 49
<211> LENGTH: 31
<212> TYPE: DNA
<213> ORGANISM: Artificial Sequence
<220> FEATURE:
<223> OTHER INFORMATION: synthetic DNA

<400> SEQUENCE: 49
ggaattccac catggcgacc tccacgggtc g                                    31

<210> SEQ ID NO 50
<211> LENGTH: 19
<212> TYPE: DNA
<213> ORGANISM: Artificial Sequence
<220> FEATURE:
<223> OTHER INFORMATION: synthetic DNA

<400> SEQUENCE: 50
tgaccagggt cccgtcgcg                                                  19

<210> SEQ ID NO 51
<211> LENGTH: 39
<212> TYPE: DNA
<213> ORGANISM: Artificial Sequence
<220> FEATURE:
<223> OTHER INFORMATION: synthetic DNA

<400> SEQUENCE: 51
gaggaccagg tggaccccag gctgatccac ggcaaggat                            39

<210> SEQ ID NO 52
```

-continued

```
<211> LENGTH: 13
<212> TYPE: PRT
<213> ORGANISM: Homo sapiens

<400> SEQUENCE: 52

Glu Asp Gln Val Asp Pro Arg Leu Ile Asp Gly Lys Asp
1               5                   10
```

METHODS FOR PRODUCING HIGHLY PHOSPHORYLATED LYSOSOMAL HYDROLASES

CROSS-REFERENCE TO RELATED APPLICATIONS

This application is a Divisional application of Ser. No. 09/635,872 filed Aug. 10, 2000, now U.S. Pat. No. 6,534,300 which claims the benefit of Ser. No. 60/153,831 filed Sep. 14, 1999.

BACKGROUND OF THE INVENTION

1. Field of the Invention

This invention relates generally to enzymes involved in the lysosomal targeting pathway and particularly to isolated and purified GlcNAc-phosphotransferase and phosphodiester α-GlcNAcase, nucleic acids encoding the enzymes, processes for production of recombinant GlcNAc-phosphotransferase and phosphodiester α-GlcNAcase, and the use of the enzymes for the preparation of highly phosphorylated lysosomal enzymes that are useful for the treatment of lysosomal storage diseases.

2. Description of the Prior Art

Lysosomes and Lysosomal Storage Diseases

Lysosomes are organelles in eukaryotic cells that function in the degradation of macromolecules into component parts that can be reused in biosynthetic pathways or discharged by the cell as waste. Normally, these macromolecules are broken down by enzymes known as lysosomal enzymes or lysosomal hydrolases. However, when a lysosomal enzyme is not present in the lysosome or does not function properly, the enzymes specific macromolecular substrate accumulates in the lysosome as "storage material" causing a variety of diseases, collectively known as lysosomal storage diseases.

Lysosomal storage diseases can cause chronic illness and death in hundreds of individuals each year. There are approximately 50 known lysosomal storage diseases, e.g., Pompe Disease, Hurler Syndrome, Fabry Disease, Maroteaux-Lamy Syndrome (mucopolysaccharidosis VI), Morquio Syndrome (mucopolysaccharidosis IV), Hunter Syndrome (mucopolysaccharidosis II), Farber Disease, Acid Lipase Deficiency, Krabbe Disease, and Sly Syndrome (mucopolysaccharidosis VII). In each of these diseases, lysosomes are unable to degrade a specific compound or group of compounds because the enzyme that catalyzes a specific degradation reaction is missing from the lysosome, is present in low concentrations in the lysosome, or is present at sufficient concentrations in the lysosome but is not functioning properly.

Lysosomal storage diseases have been studied extensively and the enzymes (or lack thereof) responsible for particular diseases have been identified. Most of the diseases are caused by a deficiency of the appropriate enzyme in the lysosome, often due to mutations or deletions in the structural gene for the enzyme. For some lysosomal storage diseases, the enzyme deficiency is caused by the inability of the cell to target and transport the enzymes to the lysosome, e.g., I-cell disease and pseudo-Hurler polydystrophy.

Lysosomal Storage diseases have been studied extensively and the enzymes (or lack thereof) responsible for particular diseases have been identified (Scriver, Beaudet, Sly, and Vale, eds., The Metabolic Basis of Inherited Disease, 6th Edition, 1989, Lysosomal Enzymes, Part 11, Chapters 61–72, pp. 1565–1839). Within each disease, the severity and the age at which the disease presents may be a function of the amount of residual lysosomal enzyme that exists in the patient.

Lysosomal Targeting Pathway

The lysosomal targeting pathways have been studied extensively and the process by which lysosomal enzymes are synthesized and transported to the lysosome has been well described. Kornfeld, S. (1986). "Trafficking of lysosomal enzymes in normal and disease states." *Journal of Clinical Investigation* 77: 1–6 and Kornfeld, S. (1990). "Lysosomal enzyme targeting." *Biochem. Soc. Trans.* 18: 367–374. Generally, lysosomal enzymes are synthesized by membrane-bound polysomes in the rough endoplastic reticulum ("RER") along with secretory glycoproteins. In the RER, lysosomal enzymes acquire N-linked oligosaccharides by the en-bloc transfer of a preformed oligosaccharide from dolichol phosphate containing 2 N-acetylglucosamine, 9-mannose and 3-glucose. Glycosylated lysosomal enzymes are then transported to the Golgi apparatus along with secretory proteins. In the cis-Golgi or intermediate compartment lysosomal enzymes are specifically and uniquely modified by the transfer of GlcNAc-phosphate to specific mannoses. In a second step, the GlcNAc is removed thereby exposing the mannose 6-phosphate ("M6P") targeting determinant. The lysosomal enzymes with the exposed M6P binds to M6P receptors in the trans-Golgi and is transported to the endosome and then to the lysosome. In the lysosome, the phosphates are rapidly removed by lysosomal phosphatases and the mannoses are removed by lysosomal mannosidases (Einstein, R. and Gabel, C. A. (1991). "Cell- and ligand-specific dephosphorylation of acid hydrolases: evidence that the mannose 6-phosphate is controlled by compartmentalization." *Journal of Cell Biology* 112: 81–94).

The synthesis of lysosomal enzymes having exposed M6P is catalyzed by two different enzymes, both of which are essential if the synthesis is to occur. The first enzyme is UDP-N-acetylglucosamine: lysosomal enzyme N-Acetylglucosamine-1-phosphotransferase ("GlcNAc-phosphotransferase") (E.C. 2.7.8.17). GlcNAc-phosphotransferase catalyzes the transfer of N-acetylglucosamine-1-phosphate from UDP-GlcNAc to the 6 position of α1,2-linked mannoses on the lysosonial enzyme. The recognition and addition of N-acetylgluocosamine-1-phosphate to lysosomal hydrolases by GlcNAc-phosphotransferase is the critical and determining step in lysosomal targeting. The second step is catalyzed by N-acetylglucosamine-1-phosphodiester α-N-Acetylglucosaminidase ("phosphodiester α-GlcNAcase") (E.C. 3.1.4.45). Phosphodiester α-GlcNAcase catalyzes the removal of N-Acetylglucosamine from the GlcNAc-phosphate modified lysosomal enzyme to generate a terminal M6P on the lysosomal enzyme. Preliminary studies of these enzymes have been conducted. Bao et al., in *The Journal of Biological Chemistry*, Vol. 271, Number 49, Issue of Dec. 6, 1996, pp. 31437–31445, relates to a method for the purification of bovine UDP-N-acetylglucosamine: Lysosomal enzyme N-Acetylglucosamine-1-phosphotransferase and proposes a hypothetical subunit structure for the protein. Bao et al., in *The Journal of Biological Chemistry*, Vol. 271, Number 49, Issue of Dec. 6, 1996, pp. 31446–31451, relates to the enzymatic characterization and identification of the catalytic subunit for bovine UDP-N-acetylglucosamine: Lysosomal enzyme N-Acetylglucosamine-1-phosphotransferase. Kornfeld et al., in *The Journal of Biological Chemistry*, Vol. 273, Number 36, Issue of Sep. 4, 1998, pp. 23203–23210, relates to the purification and multimeric structure of bovine N-Acetylglucosamine-1-phosphodiester α-N-Acetylglucosaminidase. However, the proprietary monoclonal antibodies required to isolate these proteins have not been made available to others and the protein sequences for the enzymes used in these preliminary studies have not been disclosed.

Although the lysosomal targeting pathway is known and the naturally occurring enzymes involved in the pathway have been partially studied, the enzymes responsible for adding M6P in the lysosomal targeting pathway are difficult to isolate and purify and are poorly understood. A better understanding of the lysosomal targeting pathway enzymes and the molecular basis for their action is needed to assist with the development of effective techniques for the utilization of these enzymes in methods for the treatment of lysosomal storage diseases, particularly in the area of targeted enzyme replacement therapy.

Treatment of Lysosomal Storage Diseases

Lysosomal storage diseases caused by the lack of enzymes can in theory be treated using enzyme replacement therapy, i.e., by administering isolated and purified enzymes to the patient to treat the disease. However, to be effective, the lysosomal enzyme administered must be internalized by the cell and transported to the lysosome. Naturally occurring enzymes and their recombinant equivalents, however, have been of limited value in enzyme replacement therapy because the purified or recombinant lysosomal enzymes do not contain adequate amounts of exposed M6P, or contain undesirable oligosaccharides which mediates their destruction. Without sufficient M6P, the administered lysosomal enzyme cannot efficiently bind to M6P receptors and be transported to the lysosome. For example, human acid α-glucosidase purified from placenta contains oligomannose oligosaccharides which are not phosphorylated (Mutsaers, J. H. G. M., Van Halbeek, H., Vliegenthart, J. F. G., Tager, J. M., Reuser, A. J. J., Kroos, M., and Galjaard, H. (1987). "Determination of the structure of the carbohydrate chains of acid α-glucosidase from human placenta." *Biochimica et Biophysica Acta* 911: 244–251), and this glycoform of the enzyme is not efficiently internalized by cells (Reuser, A. J., Kroos, M. A., Ponne, N. J., Wolterman, R. A., Loonen, M. C., Busch, H. F., Visser, W. J., and Bolhuis, P. A. (1984). "Uptake and stability of human and bovine acid alpha-glucosidase in cultured fibroblasts and skeletal muscle cells from glycogenosis type II patients." *Experimental Cell Research* 155: 178–189). As a result of the inability to purify or synthesize lysosomal enzymes with the desired oligosaccharide structures, these enzyme preparations are inefficiently targeted to affected cells and are of limited effectiveness in the treatment of these diseases. There exists, therefore, a need for enzymes that can be used in enzyme replacement therapy procedures, particularly highly phosphorylated enzymes that will be efficiently internalized by the cell and transported to the lysosome.

SUMMARY OF THE INVENTION

It is, therefore, an object of the present invention to provide biologically active GlcNAc-phosphotransferase and phosphodiester α-GlcNAcase as isolated and purified polypeptides.

It is another object of the present invention to provide nucleic acid molecules encoding GlcNAc-phosphotransferase and phosphodiester α-GlcNAcase.

It is another object of the present invention to provide expression vectors having DNA that encodes GlcNAc-phosphotransferase and phosphodiester α-GlcNAcase.

It is a further object of the present invention to provide host cells that have been transfected with expression vectors having DNA that encodes GlcNAc-phosphotransferase or phosphodiester α-GlcNAcase.

It is another object of the present invention to provide methods for producing recombinant GlcNAc-phosphotransferase and recombinant phosphodiester α-GlcNAcase by culturing host cells that have been transfected or transformed with expression vectors having DNA that encodes GlcNAc-phosphotransferase or phosphodiester α-GlcNAcase.

It is another object of the present invention to provide isolated and purified recombinant GlcNAc-phosphotransferase and recombinant phosphodiester α-GlcNAcase.

It is another object of the present invention to provide methods for the preparation of highly phosphorlyated lysosomal enzymes that are useful for the treatment of lysosomal storage diseases.

It is a further object of the present invention to provide highly phosphorlyated lysosomal hydrolases that are useful for the treatment of lysosomal storage diseases.

It is still another object of the present invention to provide methods for the treatment of lysosomal storage diseases.

It is still another object of the present invention to provide monoclonal antibodies to capable of selectively binding to bovine GlcNAc-phosphotransferase and to bovine phosphodiester α-GlcNAcase.

These and other objects are achieved by recovering isolated and purified biologically active GlcNAc-phosphotransferase and phosphodiester α-GlcNAcase and using the enzymes to obtain nucleic acid molecules that encode for the enzymes. The nucleic acid molecules coding for either enzyme are incorporated into expression vectors that are used to transfect host cells that express the enzyme. The expressed enzyme is recovered and used to prepare highly phosphorylated lysosomal hydrolases useful for the treatment of lysosomal storage diseases. In particular, the enzymes are used to produce highly phosphorylated-lysosomal hydrolases that can be effectively used in enzyme replacement therapy procedures.

Lysosomal hydrolases having high mannose structures are treated with GlcNAc-phosphotransferase and phosphodiester α-GlcNAcase resulting in the production of asparagine-linked oligosaccharides that are highly modified with mannose 6-phosphate ("M6P"). The treated hydrolase binds to M6P receptors on the cell membrane and is transported into the cell and delivered to the lysosome where it can perform its normal or a desired function.

Other aspects and advantages of the present invention will become apparent from the following more detailed description of the invention taken in conjunction with the accompanying drawings.

BRIEF OF DESCRIPTION OF THE DRAWINGS

FIG. 1 shows a model of the subunit structure of GlcNAc-phosphotransferase. The enzyme is a complex of six polypeptides. The α- and β-subunits are the product of a single gene. Following translation, the α- and β-subunits are separated by proteolytic cleavage between $Lys^{929}$ and $Asp^{930}$. The α-subunit is a type II membrane glycoprotein with a single amino terminal membrane spanning domain. The β-subunit is a type I membrane spanning glycoprotein with a single carboxyl terminal membrane spanning domain. The γ-subunit is the product of a second gene. The γ-subunit is a soluble protein with a cleaved signal peptide. The α-, β-, and γ-subunits are all tightly associated.

Figure 2:
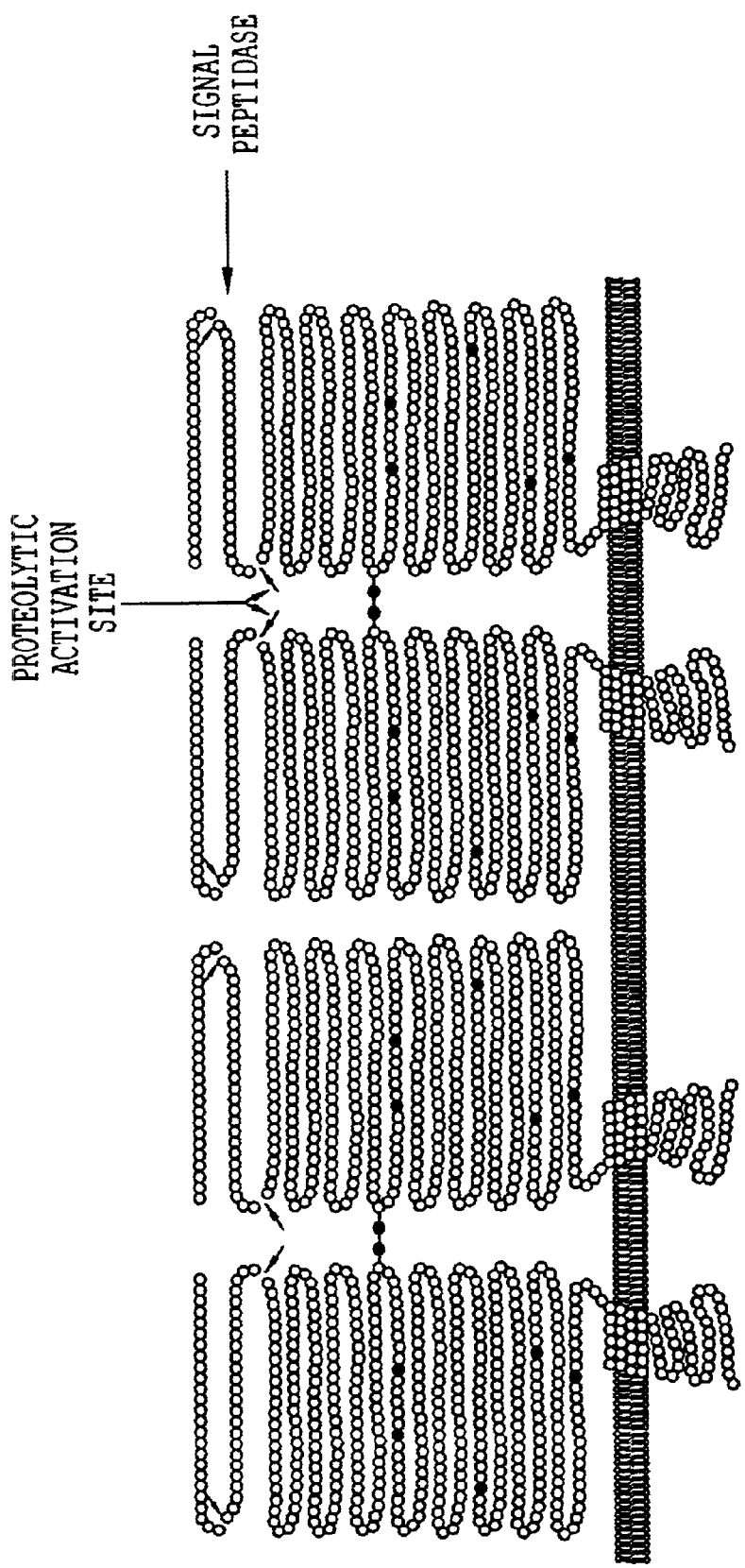

FIG. 2 shows a model of the subunit structure of phosphodiester α-GlcNAcase. The enzyme is a tetramer composed of four identical subunits arranged as two non-covalently-associated dimers which are themselves disulfide-linked. The single subunit is a type I membrane protein containing a signal peptide, a pro region not present in the mature enzyme and a single carboxyl terminal membrane spanning domain.

Figure 3:
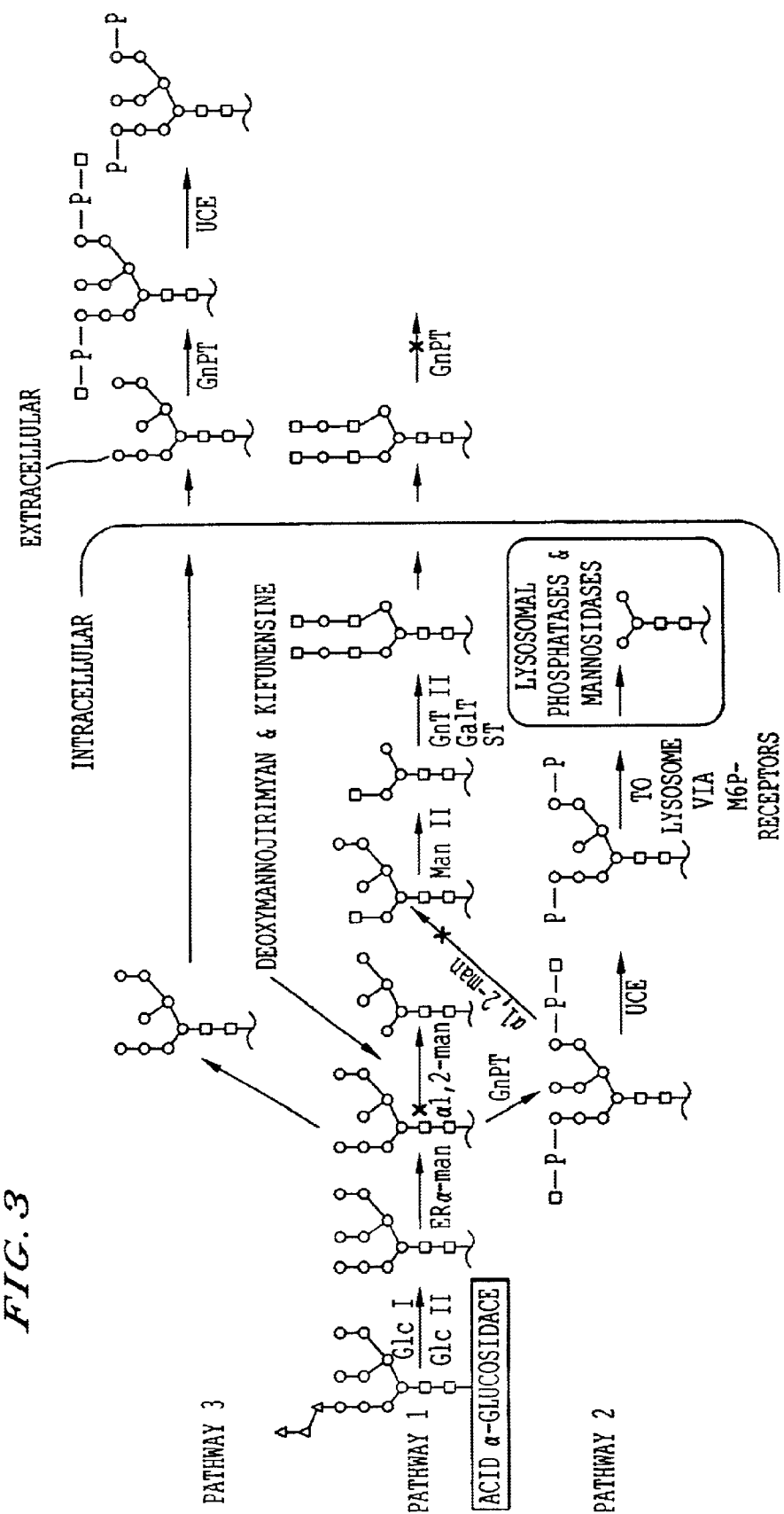

FIG. 3 shows a diagram of recombinant glycoprotein expression in CHO cells. In overexpressing CHO cells, the rh-GAA is processed along the pathways 1 and 2, depending on whether or not the enzyme is acted upon by GlcNAc-phosphotransferase (GnPT). Secreted GAA contains predominantly sialylated biantenniary complex-type glycans and is not a substrate for GlcNAc-phosphotransferase. In the presence of the α1,2-mannosidase inhibitors, 1-deoxymannojirimycin or kifunensine conversion of MAN9 to MAN5 structures is blocked, resulting in secretion of GAA-bearing MAN7-9 structures which can be modified with GlcNAc-phosphotransferase and phosphodiester α-GlcNAcase (UCE) generating phosphorylated species (pathway 3).

FIG. 4 shows transient expression analysis of various plasmid constucts of the α/β and γ subunits of human GlcNAc-phosphotransferase. Plasmids containing the α/β and/or the γ subunits were transfected into 293T cells, the expressed protein was purified from the culture at 23, 44.5 and 70 hours after transfection and relative amounts of expression were assessed by measuring phosphotransferase activity using methyl-α-D-mannoside and [β-$^{32}$P] UDP-GlcNAc as substrates.

DETAILED DESCRIPTION OF THE INVENTION

The term "GlcNAc-phosphotransferase" as used herein refers to enzymes that are capable of catalyzing the transfer of N-acetylglucosamine-1-phosphate from UDP-GlcNAc to the 6' position of α1,2-linked mannoses on lysosomal enzymes.

The term "phosphodiester α-GlcNAcase" as used herein refers to enzymes that are capable of catalyzing the removal of N-Acetylglucosamine from GlcNAc-phosphate-mannose diester modified lysosomal enzymes to generate terminal M6P.

The terms "GlcNAc-phosphotransferase" and "phosphodiester α-GlcNAcase" as used herein refer to enzymes obtained from any eukaryotic species, particularly mammalian species such as bovine, porcine, murine, equine, and human, and from any source whether natural, synthetic, semi-synthetic, or recombinant. The terms encompass membrane-bound enzymes and soluble or truncated enzymes having less than the complete amino acid sequence and biologically active variants and gene products.

The term "naturally occurring" as used herein means an endogenous or exogenous protein isolated and purified from animal tissue or cells.

The term "isolated and purified" as used herein means a protein that is essentially free of association with other proteins or polypeptides, e.g., as a naturally occurring protein that has been separated from cellular and other contaminants by the use of antibodies or other methods or as a purification product of a recombinant host cell culture.

The term "biologically active" as used herein means an enzyme or protein having structural, regulatory, or biochemical functions of a naturally occurring molecule.

The term "nucleotide sequence" as used herein means a polynucleotide molecule in the form of a separate fragment or as a component of a larger nucleic acid construct that has been derived from DNA or RNA isolated at least once in substantially pure form (i.e., free of contaminating endogenous materials) and in a quantity or concentration enabling identification, manipulation, and recovery of its component nucleotide sequences by standard biochemical methods. Such sequences are preferably provided in the form of an open reading frame uninterrupted by internal non-translated sequences, or introns that are typically present in eukaryotic genes. Sequences of non-translated DNA may be present 5' or 3' from an open reading frame where the same do not interfere with manipulation or expression of the coding region.

The term "nucleic acid molecule" as used herein means RNA or DNA, including cDNA, single or double stranded, and linear or covalently closed molecules. A nucleic acid molecule may also be genomic DNA corresponding to the entire gene or a substantial portion therefor to fragments and derivatives thereof. The nucleotide sequence may correspond to the naturally occurring nucleotide sequence or may contain single or multiple nucleotide substitutions, deletions and/or additions including fragments thereof All such variations in the nucleic acid molecule retain the ability to encode a biologically active enzyme when expressed in the appropriate host or an enzymatically active fragment thereof. The nucleic acid molecule of the present invention may comprise solely the nucleotide sequence encoding an enzyme or may be part of a larger nucleic acid molecule that extends to the gene for the enzyme. The non-enzyme encoding sequences in a larger nucleic acid molecule may include vector, promoter, terminator, enhancer, replication, signal sequences, or non-coding regions of the gene.

The term "variant" as used herein means a polypeptide substantially homologous to a naturally occurring protein but which has an amino acid sequence different from the naturally occurring protein (human, bovine, ovine, porcine, murine, equine, or other eukaryotic species) because of one or more deletions, insertions, derivations, or substitutions. The variant amino acid sequence preferably is at least 50% identical to a naturally occurring amino acid sequence but is most preferably at least 70% identical. Variants may comprise conservatively substituted sequences wherein a given amino acid residue is replaced by a residue having similar physiochemical characteristics. Conservative substitutions are well known in the art and include substitution of one aliphatic residue for another, such as Ile, Val, Leu, or Ala for one another, or substitutions of one polar residue for another, such as between Lys and Arg; Glu and Asp; or Gln and Asn. Conventional procedures and methods can be used for making and using such variants. Other such conservative substitutions such as substitutions of entire regions having similar hydrophobicity characteristics are well known. Naturally occurring variants are also encompassed by the present invention. Examples of such variants are enzymes that result from alternate mRNA splicing events or from proteolytic cleavage of the enzyme that leave the enzyme biologically active and capable of performing its catalytic function. Alternate splicing of mRNA may yield a truncated but biologically active protein such as a naturally occurring soluble form of the protein. Variations attributable to proteolysis include differences in the N- or C-termini upon expression in different types of host cells due to proteolytic removal of one or more terminal amino acids from the protein.

The term "substantially the same" as used herein means nucleic acid or amino acid sequences having sequence variations that do not materially affect the nature of the protein, i.e., the structure and/or biological activity of the protein. With particular reference to nucleic acid sequences, the term "substantially the same" is intended to refer to the coding region and to conserved sequences governing expression and refers primarily to degenerate codons encoding the same amino acid or alternate codons encoding conservative substitute amino acids in the encoded polypeptide. With reference to amino acid sequences, the term "substantially the same" refers generally to conservative substitutions and/or variations in regions of the polypeptide nor involved in determination of structure or function.

The term "percent identity" as used herein means comparisons among amino acid sequences as defined in the UWGCG sequence analysis program available from the University of Wisconsin. (Devereaux et al., Nucl. Acids Res. 12: 387–397 (1984)).

The term "highly phosphorylated lysosomal hydrolase" as used to herein means a level of phosphorylation on a purified lysosomal hydrolase which could not be obtained by only isolating the hydrolase from a natural source and without subsequent treatment with the GlcNAc-phosphotransferase and phosphodiester-α-GlcNAcase. In particular, "highly phosphorylated lysosomal hydrolase" means a lysosomal hydrolase that contains from about 6% to about 100% bis-phosphorylated oligosaccharides.

This invention is not limited to the particular methodology, protocols, cell lines, vectors, and reagents described because these may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a host cell") includes a plurality of such host cells.

Because of the degeneracy of the genetic code, a multitude of nucleotide sequences encoding GlcNAc-phosphotransferase, phosphodiester α-GlcNAcase, or other sequences referred to herein may be produced. Some of these sequences will be highly homologous and some will be minimally homologous to the nucleotide sequences of any known and naturally occurring gene. The present invention contemplates each and every possible variation of nucleotide sequence that could be made by selecting combinations based on possible codon choices. These combinations are made in accordance with the standard triplet genetic code as applied to the nucleotide sequence of naturally occurring GlcNAc-phosphotransferase or phosphodiester α-GlcNAcase, and all such variations are to be considered as being specifically disclosed.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents and publications mentioned herein are incorporated herein by reference to the extent allowed by law for the purpose of describing and disclosing the proteins, enzymes, vectors, host cells, and methodologies reported therein that might be used with the present invention. However, nothing herein is to be construed as an admission that the invention is not entitled to antedate such disclosure by virtue of prior invention.

The Invention

GlcNAc-phosphotransferase

In one aspect, the present invention provides isolated and purified biologically active GlcNAc-phosphotransferase, nucleic acid molecules encoding GlcNAc-phosphotransferase and its subunits, expression vectors having a DNA that encodes GlcNAc-phosphotransferase, host cells that have been transfected or transformed with expression vectors having DNA that encodes GlcNAc-phosphotransferase, methods for producing recombinant GlcNAc-phosphotransferase by culturing host cells that have been transfected or transformed with expression vectors having DNA that encodes GlcNAc-phosphotransferase, isolated and purified recombinant GlcNAc-phosphotransferase, and methods for using GlcNAc-phosphotransferase for the preparation of highly phosphorylated lysosomal enzymes that are useful for the treatment of lysosomal storage diseases.

To obtain isolated and purified GlcNAc-phosphotransferase and its subunits and the nucleic acid molecules encoding the enzyme according to the present invention, bovine GlcNAc phosphotransferase was obtained and analyzed as follows. Splenocytes from mice immunized with a partially purified preparation of bovine GlcNAc-phosphotransferase were fused with myeloma cells to generate a panel of hybridomas. Hybridomas secreting monoclonal antibodies specific for GlcNAc-phosphotransferase were identified by immunocapture assay. In this assay, antibodies which could capture GlcNAc-phosphotransferase from a crude source were identified by assay of immunoprecipitates with a specific GlcNAc-phosphotransferase enzymatic assay. Hybridomas were subcloned twice, antibody produced in ascites culture, coupled to a solid support and evaluated for immunoaffinity chromatography. Monoclonal PT18-Emphaze was found to allow a single step purification of GlcNAc-phosphotransferase to homogeneity. Bao, et al., The Journal of Biological Chemistry, Vol. 271, Number 49, Issue of Dec. 6, 1996, pp. 31437–31445 relates to a method for the purification of bovine UDP-N-acetylglucosamine:Lysosomal-enzyme N-Acetylglucosamine-1-phosphotransferase and proposes a hypothetical subunit structure for the protein. Bao, et. al., *The Journal of Biological Chemistry, Vol.* 271, Number 49, Issue of Dec. 6, 1996, pp. 31446–31451. Using this technique, the enzyme was purified 488,000-fold in 29% yield. The eluted GlcNAc-phosphotransferase has a specific activity of $>10^6$, preferably $>5\times10^6$, more preferably $>12\times 10^6$ pmol/h/mg and is apparently a homogenous, multi-subunit enzyme based on silver-stained SDS-PAGE. The monoclonal antibody labeled PT18 was selected for use in further experiments. A hybridoma secreting monoclonal antibody PT 18 was deposited with the American Type Culture Collection, 10801 Univerisity Blvd., Manassas, Va. 20110 and assigned ATCC Accession No. PTA-2432.

GlcNAc-phosphotransferase was determined to be a complex of six polypeptides with a subunit structure $\alpha_2\beta_2\gamma_2$. FIG. 1 shows a model of the subunit structure obtained from quantitative amino acid sequencing, immunoprecipitation with subunit-specific monoclonal antibodies, SDS-PAGE, and cDNA sequences. The evidence for the model is summarized below. The molecular mass of the complex estimated by gel filtration is 570,000 Daltons. The 166,000 Dalton α-subunit is found as a disulfide-linked homodimer. Likewise, the 51,000 Dalton γ-subunit is found as a disulfide-linked homodimer. Because both the α- and γ-subunits are found in disulfide-linked homodimers, each molecule must contain at least one α- and one γ homodimer. Although the 56,000 Dalton β-subunit is not found in a disulfide-linked homodimer, two independent lines of evidence strongly suggest each complex contains two β-subunits as well. First, quantitative aminoterminal sequencing demonstrates a 1:1 molar ratio between the β- and γ-subunits. Secondly, since the α- and β-subunits are encoded by a single cDNA and divided by proteolytic processing, two β-subunits are produced for each α-subunit dimer. The predicted mass of the complex based on the composition $α_2β_2γ_2$ is 546,000 Daltons (2×166,000+2×56,000+2×51,000) in excellent agreement with the mass estimated by gel filtration.

GlcNAc-phosphotransferase was purified using an assay for the transfer of GlcNAc-1-Phosphate to the synthetic acceptor α-methylmannoside. However, the natural acceptors for GlcNAc-phosphotransferase are the high mannose oligosaccharides of lysosomal hydrolases. To evaluate the ability of the purified GlcNAc-phosphotransferase to utilize glycoproteins as acceptors, the transfer of GlcNAc-1-P to the lysosomal enzymes uteroferrin and cathepsin D, the nonlysosomal glycoprotein RNAse B, and the lysosomal hydrolase β-glucocerebrosidase (which is trafficked by a M6P independent pathway), were investigated. Both uteroferrin and cathepsin D are effectively utilized as acceptors by purified GlcNAc-phosphotransferase with $K_m$s below 20 μm. In contrast, neither RNAse B nor β-glucocerebrosidase is an effective acceptor.

The ineffectiveness of RNAse B, which contains a single high mannose oligosaccharide, as an acceptor is especially notable since the $K_m$ was not reached at the solubility limit of the protein (at 600 μm). This data clearly demonstrates the specific phosphorylation of Lysosomal hydrolases previously observed with crude preparations (Waheed, Pohlmann A., R., et al. (1982). "Deficiency of UDP-N-acetylglucosamine:lysosomal enzyme N-Acetylglucosamine-1phosphotransferase in organs of I-Cell patients." *Biochemical and Biophysical Research Communications* 105(3): 1052–10580 is a property of the GlcNAc-phosphotransferase itself.

The α-subunit was identified as containing the UDP-GlcNAc binding site since this subunit was specifically photoaffinity-labeled with [β-$^{32}$P]-5-azido-UDP-Glc.

The amino-terminal and internal (tryptic) protein sequence data was obtained for each subunit. N-terminal sequence was obtained from each subunit as follows. Individual subunits of GlcNAc-phosphotransferase were resolved by polyacrylamide gel electrophoresis in the presence of sodium dodecyl sulfate before and after disulfide bond reduction. Subunits were then transferred to a PVDF membrane by electroblotting, identified by Coomassie blue staining, excised, and subjected to N-terminal sequencing. To obtain internal sequence, GlcNAc-phosphotransferase was denatured, reduced, and alkylated, and individual subunits were resolved by gel filtration chromatography. Isolated subunits were then digested with trypsin and the tryptic peptides fractionated by reverse phase HPLC. Peaks which appeared to contain only a single peptide were analyzed for purity by MALDI and subjected to N-terminal amino acid sequencing.

The amino acid sequence for the human α-subunit is shown in amino acids 1–928 of SEQ ID NO: 1; the human β-subunit in amino acids 1–328 of SEQ ID NO:2; and the human γ-subunit in amino acids 25–305 of SEQ ID NO:3. The γ-subunit has a signal sequence shown in amino acids 1–24 of SEQ ID NO:3.

Comparison with the databases using the blast algorithms demonstrate these proteins have not been previously described although several EST sequences of the corresponding cDNAs are present.

Using these peptide sequences and a combination of library screening, RACE, PCR and Blast searching of expressed sequence tag ("EST") files, full-length human cDNAs encoding each subunit were cloned and sequenced.

The nucleotide sequence for the human α/β-subunit precursor cDNA is shown in nucleotides 165–3932 of SEQ ID NO:4; the nucleotide sequence for the α-subunit is shown in nucleotides 165–2948 of SEQ ID NO:4; the nucleotide sequence for the β-subunit is shown in nucleotides 2949–3932 of SEQ ID NO:4; and the nucleotide sequence for the γ-subunit is shown in nucleotides 96–941 of SEQ ID NO:5. The nucleotide sequence for the γ-subunit signal peptide is shown in nucleotides 24–95 of SEQ ID NO:5.

For each subunit a N-terminal peptide and two internal peptide sequences have been identified in the respective cDNA sequence. Although the protein sequence data is from the bovine protein and the cDNA sequences are human, the sequences are highly homologous (identities: α-subunit 43/50; β-subunit 64/64; γ-subunit 30/32), confirming the cloned cDNAs represent the human homologs of the bovine GlcNAc-phosphotransferase subunits. The α- and β-subunits were found to be encoded by a single cDNA whose gene is on chromosome 12. The γ-subunit is the product of a second gene located on chromosome 16. The α/β-subunits precursor gene has been cloned and sequenced. The gene spans ~80 kb and contains 21 exons. The γ-subunit gene has also been identified in data reported from a genome sequencing effort. The γ-subunit gene is arranged as 11 exons spanning 12 kb of genomic DNA.

Using the human cDNAs, the homologous murine cDNAs for the α-, β- and γ-subunits were isolated and sequenced using standard techniques. The murine α- β-subunit precursor cDNA is shown in SEQ ID NO:16. The deduced amino acid sequence for the murine α-subunit is shown in SEQ ID NO: 15 and the β-subunit in SEQ ID NO:8.

The mouse γ-subunit cDNA was isolated from a mouse liver library in λZap II using the γ-human γ-subunit cDNA as a probe. The human γ-subunit cDNA was random hexamer-labeled with $^{32}$P-dCTP and used to screen a mouse liver cDNA library in λZap II. The probe hybridized to three of 500,000 plaques screened. Each was subcloned to homogeneity, the insert excised, cloned into pUC19, and sequenced using standard methods Sambrook, J., Fritsch E. F., et al. (1989). *Molecular Cloning. A Laboratory Manual.* Cold Spring Harbor, Cold Spring Harbor Laboratory Press. The mouse γ-subunit cDNA sequence is shown in SEQ ID NO:10 and the deduced amino acid sequence for the mouse γ-subunit is shown in SEQ ID NO:9.

Comparison of the deduced amino acid sequences of the human and mouse α-, β-, and γ-subunits demonstrates that the proteins are highly homologous with about an 80 percent identity.

To confirm that these enzymes were substantially the same between species, a partial homologous rat cDNA for the α- and β-subunits was isolated and sequenced using standard techniques. The partial rat α- and β-subunit cDNA is shown in SEQ ID NO:12. The deduced amino acid sequence corresponding to the cDNA is shown in SEQ ID NO:11. Further, a partial homologous Drosophila cDNA for the α- and β-subunits was isolated and sequenced using standard techniques. The partial Drosophila α- and β-subunit cDNA is shown in SEQ ID NO:17. The deduced amino acid sequence corresponding to the cDNA is shown in SEQ ID NO:13. Comparisons of the deduced amino acid sequences of the partial human, rat, and Drosophila α- and β-subunits show that the proteins are highly homologous.

Phosphodiester α-GlcNAcase

In another aspect, the present invention provides isolated and purified biologically active phosphodiester α-GlcNAcase, nucleic acid molecules encoding phosphodiester α-GlcNAcase, expression vectors having a DNA that encodes phosphodiester α-GlcNAcase, host cells that have been transfected or transformed with expression vectors having DNA that encodes phosphodiester α-GlcNAcase, methods for producing recombinant phosphodiester α-GlcNAcase by culturing host cells that have been transfected or transformed with expression vectors having DNA that encodes phosphodiester α-GlcNAcase, isolated and purified recombinant phosphodiester α-GlcNAcase, and methods for using phosphodiester α-GlcNAcase for the preparation of highly phosphorylated lysosomal enzymes that are useful for the treatment of lysosomal storage diseases.

To obtain isolated and purified phosphodiester α-GlcNAcase and the nucleic acid molecules encoding the enzyme according to the present invention, bovine phosphodiester α GlcNAcase was obtained and analyzed as follows. Mice were immunized with a partially purified preparation of phosphodiester α-GlcNAcase and a functional screening strategy was utilized to identify and isolate a monoclonal antibody specific for phosphodiester α-GlcNAcase. Immunogen was prepared by partially purifying phosphodiester α-GlcNAcase ~6000-fold from a bovine pancreas membrane pellet using chromatography on DEAE-Sepharose, iminodiacetic acid Sepharose, and Superose 6. Two BALBlc mice were each injected intraperitoneally with 5 μg partially purified phosphodiester α-GlcNAcase emulsified in Freunds complete adjuvant. On day 28, the mice were boosted intraperitoneally with 5 μg phosphodiester α-GlcNAcase emulsified in Freunds incomplete adjuvant. On day 42 the mice were bled and an phosphodiester α-GlcNAcase specific immune response was documented by "capture assay." To perform the capture assay, serum (5 μl) was incubated overnight with 1.2 units partially purified phosphodiester α-GlcNAcase. Mouse antibody was then captured on rabbit antimouse IgG bound to protein A-Ultralink™ resin. Following extensive washing, bound phosphodiester α-GlcNAcase was determined in the Ultralink pellet by assay of cleavage of [$^3$H]-GlcNAc-1-phosphomannose α-methyl.

Following a second intravenous boost with phosphodiester α-GlcNAcase, the spleen was removed and splenocytes fused with SP2/0 myeloma cells according to our modifications (Bag, M., Booth J. L., et al. (1996). "Bovine UDP-N-acetylglucosamine: lysosomal enzyme N-acetylglucosamine-1-phosphotransferase. I. Purification and subunit structure." *Journal of Biological Chemistry* 271: 31437–31445) of standard techniques; Harlow, E. and Lane, D. (1988). *Antibodies: a laboratory manual,* Cold Spring Harbor Laboratory). The fusion was plated in eight 96-well plates in media supplemented with recombinant human IL-6 (Bazin, R. and Lemieux, R. (1989). "Increased proportion of B cell hybridomas secreting monoclonal antibodies of desired specificity in cultures containing macrophage-derived hybridoma growth factor (IL-6)." *Journal of Immunological Methods* 116: 245–249) and grown until hybridomas were just visible. Forty-eight pools of 16-wells were constructed and assayed for antiphosphodiester α-GlcNAcase activity using the capture assay. Four pools were positive. Subpools of 4-wells were then constructed from the wells present in the positive 16-well pools. Three of the four 16-well pools contained a single 4-well pool with anti-phosphodiester α-GlcNAcase activity. The 4 single wells making up the 4-well pools were then assayed individually identifying the well containing the anti-phosphodiester α-GlcNAcase secreting hybridomas. Using the capture assay, each hybridoma was subcloned twice and antibody prepared by ascites culture. Monoclonals UC2 and UC3 were found to be low affinity antibodies. UC1, a high affinity IgG monoclonal antibody, was prepared by ascites culture and immobilized on Emphaze for purification of phosphodiester α-GlcNAcase. The monoclonal antibody labeled UC1 was selected for use in further experiments. A hybridoma secreting monoclonal antibody UC1 was deposited with the American Type Culture Collection, 10801 Univerisity Blvd., Manassas, Va. 20110 and assigned ATCC Accession No. PTA 2431.

To purify phosphodiester α-GlcNAcase, a solubilized membrane fraction was prepared from bovine liver. Phosphodiester α-GlcNAcase was absorbed to monoclonal antibody UC1 coupled to Emphaze resin by incubation overnight with gentle rotation. The UC1-Emphaze was then packed in a column, washed sequentially with EDTA and NaHCO$_3$ at pH 7.0, then phosphodiester α-GlcNAcase was eluted with NaHCO$_3$ at pH 10. Fractions containing phosphodiester α-GlcNAcase at specific activities >50,000 μ/mg were pooled and adjusted to pH 8.0 with ⅛th volume of 1 M Tris HCI, pH 7.4. Following chromatography on UCI-Emphaze the phosphodiester α-GlcNAcase was purified 92,500-fold in 32% yield.

The phosphodiester α-GlcNAcase from UC1-Emphaze was concentrated and chromatographed on Superose 6. Phosphodiester α-GlcNAcase eluted early in the chromatogram as a symmetric activity peak with a coincident protein peak. Following chromatography on Superose 6, the enzyme was purified ~715,000-fold in 24% yield. The purified enzyme catalyzed the cleavage of 472 μmols/hr/mg [$^3$H]-GlcNAc-1-phosphomannose-α-methyl, corresponding to a specific activity of 472,000 units/mg.

The purified phosphodiester α-GlcNAcase was subjected to SDS-PAGE and protein was detected by silver staining (Blum, H., Beier H., et al. (1987). "Improved silver staining of plant proteins, RNA and DNA in polyacrylamide gels." *Electrophoresis:* 93–99). A diffuse band was observed with a molecular mass of approximately 70 kDa whose intensity varies with the measured phosphodiester α-GlcNAcase activity. The diffuse appearance of the band suggests the protein may be heavily glycosylated. A faint band with a molecular mass of ~150,000, which does not correlate with activity, was also present.

A model for the subunit structure of phosphodiester α-GlcNAcase was determined by gel filtration chromatography and SDS-PAGE with and without disulfide bond reduction. The mass by gel filtration is about 300,000. SDS-PAGE without disulfide bond reduction is ~140,000. Following disulfide bond reduction, the apparent mass is 70,000. Together these data show phosphodiester α-GlcNAcase is a tetramer composed of disulfide linked homodimers. FIG. 2 shows a model of the subunit structure of phosphodiester α-GlcNAcase.

The amino terminal amino acid sequence of affinity purified, homogeneous bovine phosphodiester α-GlcNAcase was determined using standard methods (Matsudaira, P., Ed. (1993). *A Practical Guide to Protein*

*and Peptide Purification for Microsequencing.* San Diego, Academic Press, Inc.). The pure enzyme was also subjected to trypsin digestion and HPLC to generate two internal tryptic peptides which were sequenced. The amino acid sequences of these three peptides are:

```
Peptide 1-Amino Terminal DXTRVHAGRLEHESWPPAAQTAGAHRPSVRTFV;  (SEQ ID NO:23)

Peptide 2- Tryptic RDGTLVTGYLSEEEVLDTEN: and                 (SEQ ID NO:24)

Peptide 3- Tryptic GINLWEMAEFLLK.                            (SEQ ID NO:25).
```

The protein, nucleotide, and EST data bases were searched for sequences that matched these peptide sequences and several human and mouse ESTs were found that had the sequence of the third peptide at their amino termini. Three human infant brain EST clones and one mouse embryo clone were obtained from ATCC and sequenced. The three human clones were all identical except for total length at their 3' ends and virtually identical to the mouse clone, except that the mouse EST contained a 102 bp region that was absent from all three human brain ESTs. An EcoRI-HindIII fragment of about 700 bp was excised from the human cDNA clone (ATCC # 367524) and used to probe a human liver cDNA library directionally cloned in TriplEx vector (Clontech). Of the positive clones isolated from the library and converted to plasmids (pTriplEx), the largest (2200 bp) was represented by clone 6.5 which was used for the rest of the analysis.

The cDNA clone has been completely sequenced on both strands and is a novel sequence that predicts a mature protein of about 50 kDa which is in agreement with the size of the deglycosylated mature bovine liver phosphodiester α-GlcNAcase.

There is a unique BamH I site at base #512 and a unique Hind ID site at base # 1581. All three bovine peptide sequences (peptides 1, 2, and 3) were found. Although the sequences of peptides 2 and 3 in the human are 100% identical to the bovine sequences, the amino-terminal peptide in humans is only 67% identical to the bovine sequence. The human liver clone contains the 102 base pair insert that has the characteristics of an alternatively spliced segment that was missing in the human brain EST. The hydrophilicity plot indicates the presence of a hydrophobic membrane spanning region from amino acids 448 to 474 and another hydrophobic region from amino acid 8 to 24 which fits the motif for a signal sequence and there is a likely signal sequence cleavage site between G24 and G25. There are six Asn-X-Ser/Thr potential N-linked glycosylation sites, one of which is within the 102 bp insert. All of these sites are amino terminal of the putative trans-membrane region. These features indicate that the phosphodiester α-GlcNAcase is a type I membrane spanning glycoprotein with the amino terminus in the lumen of the Golgi and the carboxyl terminus in the cytosol. This orientation is different from that of other glycosyltransferases and glycosidases involved in glycoprotein processing, which to date have been shown to be type II membrane spanning proteins.

The amino acid sequence for the phosphodiester α-GlcNAcase monomer is shown in amino acids 50–515 of SEQ ID NO:6. The signal peptide is shown in amino acids 1–24 of SEQ ID NO:6 and the pro segment is shown in amino acids 25–49 of SEQ ID NO:6. The human cDNA was cloned using the techniques described above. The nucleotide sequence for the monomer that associates to form the phosphodiester α-GlcNAcase tetramer is shown in nucleotides 151–1548 of SEQ ID NO:7. The nucleotide sequence for the signal sequence is shown in nucleotides 1–72 of SEQ ID NO:7. The nucleotide sequence for the propeptide is shown in nucleotides 73–150 of SEQ ID NO:7.

The murine cDNA for phosphodiester α-GlcNAcase is shown in SEQ ID NO:18. The deduced amino acid sequence for the murine phosphodiester α-GlcNAcase is shown in SEQ ID NO:19. Comparison of the deduced amino acid sequences of the human and mouse enzymes demonstrates that the proteins are highly homologous with about an 80 percent identity. This is especially true in the region of the active site where identity exceeds 90%. The murine gene for phosphodiester α-GlcNAcase is shown in SEQ ID NO:14.

The human phosphodiester α-GlcNAcase gene has been identified by database searching. The sequence was determined during the sequencing of clone 165E7 from chromosome 16.13.3, GenBank AC007011.1, gi4371266. Interestingly, the phosphodiester α-GlcNAcase gene was not identified by the SCAN program used to annotate the sequence.

Because of the degeneracy of the genetic code, a DNA sequence may vary from that shown in SEQ ID NO:4, SEQ ID NO:5, and SEQ ID NO:7 and still encode a GlcNAc phosphotransferase and a phosphodiester α-GlcNAcase enzyme having the amino acid sequence shown in SEQ ID NO: 1, SEQ ID NO:2, SEQ ID NO:3, and SEQ ID NO:6. Such variant DNA sequences may result from silent mutations, e.g., occurring during PCR amplification, or may be the product of deliberate mutagenesis of a native sequence. The invention, therefore, provides equivalent isolated DNA sequences encoding biologically active GlcNAc-phosphotransferase and phosphodiester α-GlcNAcase selected from: (a) the coding region of a native mammalian GlcNAc-phosphotransferase gene and phosphodiester α-GlcNAcase gene; (b) cDNA comprising the nucleotide sequence presented in SEQ ID NO:4, SEQ ID NO:5, and SEQ ID NO:7; (c) DNA capable of hybridization to the native mammalian GlcNAc-phosphotransferase gene and phosphodiester α-GlcNAcase gene under moderately stringent conditions and which encodes biologically active GlcNAc-phosphotransferase and phosphodiester α-GlcNAcase; and (d) DNA which is degenerate as a result of the genetic code to a DNA defined in (a), (b), or (c) and which encodes biologically active GlcNAc-phosphotransferase and phosphodiester α-GlcNAcase. GlcNAc-phosphotransferase and phosphodiester α-GlcNAcase proteins encoded by such DNA equivalent sequences are encompassed by the invention.

Those sequences which hybridize under stringent conditions and encode biologically functional GlcNAc-phosphotransferase and phosphodiester α-GlcNAcase are preferably at least 50–100% homologous, which includes 55, 60, 65, 70, 75, 75, 80, 85, 90, 95, 99% and all values and subranges therebetween. Homology may be determined with the software UWCG as described above. Stringent hybridization conditions are known in the art and are meant to include those conditions which allow hybridization to those sequences with a specific homology to the target sequence.

An example of such stringent conditions are hybridization at 65° C. in a standard hybridization buffer and subsequent washing in 0.2×concentrate SSC and 0.1% SDS at 42–65° C., preferably 60° C. This and other hybridization conditions are disclosed in Sambrook, J., Fritsch E. F., et al. (1989). *Molecular Cloning. A Laboratory Manual.* Cold Spring Harbor, Cold Spring Harbor Laboratory Press. Alternatively, the temperature for hybridization conditions may vary dependent on the percent GC content and the length of the nucleotide sequence, concentration of salt in the hybridization buffer and thus the hybridization conditions may be calculated by means known in the art.

Recombinant Expression for GlcNAc-phosphotransferase and Phosphodiester α-GlcNAcase Isolated and purified recombinant GlcNAc-phosphotransferase and phosphodiester α-GlcNAcase enzymes are provided according to the present invention by incorporating the DNA corresponding to the desired protein into expression vectors and expressing the DNA in a suitable host cell to produce the desired protein.

Expression Vectors

Recombinant expression vectors containing a nucleic acid sequence encoding the enzymes can be prepared using well known techniques. The expression vectors include a DNA sequence operably linked to suitable transcriptional or translational regulatory nucleotide sequences such as those derived from mammalian, microbial, viral, or insect genes. Examples of regulatory sequences include transcriptional promoters, operators, enhancers, mRNA ribosomal binding sites, and appropriate sequences which control transcription and translation initiation and termination. Nucleotide sequences are "operably linked" when the regulatory sequence functionally relates to the DNA sequence for the appropriate enzyme. Thus, a promoter nucleotide sequence is operably linked to a GlcNAc-phosphotransferase or phosphodiester a GlcNAcase DNA sequence if the promoter nucleotide sequence controls the transcription of the appropriate DNA sequence.

The ability to replicate in the desired host cells, usually conferred by an origin of replication and a selection gene by which transformants are identified, may additionally be incorporated into the expression vector.

In addition, sequences encoding appropriate signal peptides that are not naturally associated with GlcNAc-phosphotransferase or phosphodiester α-GlcNAcase can be incorporated into expression vectors. For example, a DNA sequence for a signal peptide (secretory leader) may be fused in-frame to the enzyme sequence so that the enzyme is initially translated as a fusion protein comprising the signal peptide. A signal peptide that is functional in the intended host cells enhances extracellular secretion of the appropriate polypeptide. The signal peptide may be cleaved from the polypeptide upon secretion of enzyme from the cell.

Host Cells

Suitable host cells for expression of GlcNAc-phosphotransferase and phosphodiester at α-GlcNAcase include prokaryotes, yeast, archae, and other eukaryotic cells. Appropriate cloning and expression vectors for use with bacterial, fungal, yeast, and mammalian cellular hosts are well known in the art, e.g., Pouwels et al. Cloning Vectors: A Laboratory Manual, Elsevier, N.Y. (1985). The vector may be a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsulated virus by well known techniques for infection and transduction. Viral vectors may be replication competent or replication defective. In the latter case viral propagation generally will occur only in complementing host cells. Cell-free translation systems could also be employed to produce the enzymes using RNAs derived from the present DNA constructs.

Prokaryotes useful as host cells in the present invention include gram negative or gram positive organisms such as *E. coli* or Bacilli. In a prokaryotic host cell, a polypeptide may include a N-terminal methionine residue to facilitate expression of the recombinant polypeptide in the prokaryotic host cell. The N-terminal Met may be cleaved from the expressed recombinant GlcNAc-phosphotransferase or phosphodiester α-GlcNAcase polypeptide. Promoter sequences commonly used for recombinant prokaryotic host cell expression vectors include β-lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector.

Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., Nature 275:615, (1978); and Goeddel et al., Nature 281:544, (1979)), tryptophan (trp) promoter system (Goeddel et al., Nucl. Acids Res. 8:4057, (1980)), and tac promoter (Maniatis, Molecular Cloning: A Laboratory Manual, Cold Spring Harbor Laboratory, p. 412 (1982)).

Yeasts useful as host cells in the present invention include those from the genus Saccharomyces, Pichia, K. Actinomycetes and Kluyveromyces. Yeast vectors will often contain an origin of replication sequence from a $2\mu$ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvatee decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285–195 (1991). Other suitable promoters and vectors for yeast and yeast transformation protocols are well known in the art.

Yeast transformation protocols are known to those of skill in the art. One such protocol is described by Hinnen et al., *Proceedings of the National Academy of Sciences USA*, 75:1929 (1978). The Hinnen protocol selects for Trp.sup.+ transformants in a selective medium, wherein the selective medium consists of 0.67% yeast nitrogen base, 0.5% casamino acids, 2% glucose, 10 µg/ml adenine, and 20 µg/ml uracil.

Mammalian or insect host cell culture systems well known in the art could also be employed to express recombinant GlcNAc-phosphotransferase or phosphodiester α-GlcNAcase polypeptides, e.g., Baculovirus systems for production of heterologous proteins in insect cells (Luckow and Summers, Bio/Technology 6:47 (1988)) or Chinese hamster ovary (CHO) cells for mammalian expression may be used. Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

The enzymes of the present invention may, when beneficial, be expressed as a fusion protein that has the enzyme attached to a fusion segment. The fusion segment often aids in protein purification, e.g., by permitting the fusion protein to be isolated and purified by affinity chromatography. Fusion proteins can be produced by culturing a recombinant cell transformed with a fusion nucleic acid sequence that encodes a protein including the fusion segment attached to either the carboxyl and/or amino terminal end of the enzyme. Preferred fusion segments include, but are not limited to, glutathione-S-transferase, β-galactosidase, a poly-histidine segment capable of binding to a divalent metal ion, and maltose binding protein. In addition, the HPC-4 epitope purification system may be employed to facilitate purification of the enzymes of the present invention. The HPC-4 system is described in U.S. Pat. No. 5,202,253, the relevant disclosure of which is herein incorporated by reference.

Expression by Gene Activation Technology

In addition to expression strategies involving transfection of a cloned cDNA sequence, the endogenous GlcNAc-phophotransfease and phosphodiester α-GlcNAcase genes can be expressed by altering the promoter.

Methods of producing the enzymes of the present invention can also be accomplished according to the methods of protein production as described in U.S. Pat. No. 5,968,502, the relevant disclosure of which is herein incorporated by reference, using the sequences for GlcNAc-phosphotransferase and phosphodiester α-GlcNAcase as described herein.

Expression and Recovery

According to the present invention, isolated and purified GlcNAc-phosphotransferase or phosphodiester α-GlcNAcase enzymes may be produced by the recombinant expression systems described above. The method comprises culturing a host cell transformed with an expression vector comprising a DNA sequence that encodes the enzyme under conditions sufficient to promote expression of the enzyme. The enzyme is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium. When expression systems that secrete the recombinant protein are employed, the culture medium first may be concentrated. Following the concentration step, the concentrate can be applied to a purification matrix such as a gel filtration medium. Alternatively, an anion exchange resin can be employed, e.g., a matrix or substrate having pendant diethylaminoethyl (DEAE) groups. The matrices can be acrylamide, agarose, dextran, cellulose, or other types commonly employed in protein purification. Also, a cation exchange step can be employed. Suitable cation exchangers include various insoluble matrices comprising sulfopropyl or carboxymethyl groups. Further, one or more reversed-phase high performance liquid chromatography (RP-HPLC) steps employing hydrophobic RP-HPLC media (e.g., silica gel having pendant methyl or other aliphatic groups) can be employed to further purify the enzyme. Some or all of the foregoing purification steps, in various combinations, are well known in the art and can be employed to provide an isolated and purified recombinant protein.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification, or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Preparation of Highly Phosphorylated Lysosomal Enzymes

In another aspect, the present invention provides highly phosphorylated lysosomal hydrolases and methods for the preparation of such hydrolases. The highly phosphorylated lysosomal hydrolases can be used in clinical applications for the treatment of lysosomal storage diseases.

The method comprises obtaining lysosomal hydrolases having asparagine-linked oligosaccharides with high mannose structures and modifying the α1,2-linked or other outer mannoses by the addition of M6P in vitro to produce a hydrolase that can be used for the treatment of lysosomal storage diseases because it binds to cell membrane M6P receptors and is readily taken into the cell and into the lysosome. Typically, the high mannose structures consist of from six to nine molecules of mannose and two molecules of N-acetylglucosamine (GlcNAc). In the preferred embodiment, the high mannose structure is a characteristic MAN7($D_2D_3$) isomer structure consisting of seven molecules of mannose and two molecules of N-acetylglucosamine (GlcNAc).

Highly phosphorylated Lysosomal hydrolases are produced by treating the high mannose hydrolases with GlcNAc-phosphotransferase which catalyzes the transfer of N-acetylglucosamine-1-phosphate from UDP-GlcNAc to the 6' position of α1,2-linked or other outer mannoses on the hydrolase. This GlcNAc-phosphotransferase modified hydrolase is then treated with phosphodiester α-GlcNAcase which catalyzes the removal of N-Acetylglucosamine to generate terminal M6P on the hydrolase.

In one embodiment of the invention, the GlcNAc-phosphotransferase treated hydrolase may be isolated and stored without any subsequent treatment. Subsequently, the GlcNAc-phosphotransferase treated hydrolase may be modified further by treating the hydrolase with a phosphodiester α-GlcNAcase.

Surprisingly, it has been found that the hydrolases containing M6P generated by this method are highly phosphorylated when compared to naturally occurring or known recombinant hydrolases. The highly phosphorylated lysosomal hydrolases of the present invention contain from about 6% to about 100% bis-phosphorylated oligosaccharides compared to less that about 5% bis-phosphorylated oligosaccharides on known naturally occurring or recombinant hydrolases.

These highly phosphorylated hydrolases have a higher affinity for the M6P receptor and are therefore more efficiently taken into the cell by plasma membrane receptors. (Reuser, A. J., Kroos, M. A., Ponne, N. J., Wolterman, R. A., Loonen, M. C., Busch, H. F., Visser, W. J., and Bolhuis, P. A. (1984). "Uptake and stability of human and bovine acid alpha-glucosidase in cultured fibroblasts and skeletal muscle cells from glycogenosis type II patients." *Experimental Cell Research* 155:178–189).

The high-affinity ligand for the cation-independent M6P receptor is an oligosaccharide containing two M6P groups (i.e., a bis-phosphorylated oligosaccharide). Since a bisphosphorylated oligosaccharides binds with an affinity 3500-fold higher than a monophosphorylated oligosaccharides, virtually all the high-affinity binding of a lysosomal enzyme to the M6P receptor will result from the content of bis-phosphorylated oligosaccharides (Tong, P. Y., Gregory, W., and Kornfeld, S. (1989)). "Ligand interactions of the cation-independent mannose 6-phosphate receptor. The stoichiometry of mannose 6-phosphate binding." *Journal of Biological Chemistry* 264: 7962–7969). It is therefore appropriate to use the content of bis-phosphorylated oligosaccharides to compare the binding potential of different preparations of lysosomal enzymes.

The extent of mannose 6-phosphate modification of two different lysosomal enzymes has been published. The oligosaccharide composition of human α-galactosidase A secreted from Chinese hamster ovary cells has been published (Matsuura, F., Ohta, M., Ioannou, Y. A., and Desnick, R. I. (1998). "Human alpha-galactosidase A: characterization of the N-linked oligosaccharides on the intracellular and secreted glycoforms overexpressed by Chinese hamster ovary cells." *Glycobiology* 8(4): 329–39). Of all oligosaccharides on α-gal A released by hydrazinolysis, only 5.2% were bis-phosphorylated. Zhao et al. partially characterized the oligosaccharide structures on recombinant human α-iduronidase secreted by CHO cells (Zhao, K. W., Faull, K. F., Kakkis, E. D., and Neufeld, E. F. (1997). "Carbohydrate structures of recombinant human alpha-L-iduronidase secreted by Chinese hamster ovary cells." *J Biol Chem* 272(36): 22758–65) and demonstrated a minority of the oligosaccharides were bisphosphorylated. The qualitative techniques utilized precluded the determination of the fraction of oligosaccharides phosphorylated.

The production and secretion of human acid α-glucosidase by CHO cells has been reported (Van Hove, J. L., Yang, H. W., Wu, J. Y., Brady, R. O., and Chen, Y. T. (1996). "High level production of recombinant human lysosomal acid alpha-glucosidase in Chinese hamster ovary cells which targets to heart muscle and corrects glycogen accumulation in fibroblasts from patients with Pompe disease." *Proceedings of the National Academy of Sciences USA*, 93(1): 6570). The carbohydrate structures of this preparation were not characterized in this publication. However, this preparation was obtained and analyzed. The results, given in the examples below, showed that less than 1% of the oligosaccharides contained any M6P and bis-phosphorylated oligosaccharides were not detectable. Together, these data show that known preparations of recombinant lysosomal enzymes contain no more than 5.2% phosphorylated oligosaccharides. It appears that the preparation of more highly phosphorylated lysosomal enzymes is unlikely to be achieved with known techniques. Naturally occurring human acid α-glucosidase purified from human placenta contains very low levels of M6P (Mutsaers, I. H. G. M., Van Halbeek, H., Vliegenthart, J. F. G., Tager, J. M., Reuser, A. J. J., Kroos, M., and Galjaard, H. (1987). "Determination of the structure of the carbohydrate chains of acid α-glucosidase from human placenta." *Biochimica et Biophysica Acta* 911: 244–251). The arrangement of the phosphates as either bis- or monophosphorylated oligosaccharides has not been determined, but less than 1% of the oligosaccharides contain any M6P.

The highly phosphorylated hydrolases of the present invention are useful in enzyme replacement therapy procedures because they are more readily taken into the cell and the lysosome. (Reuser, A. J., Kroos, M. A., Ponne, N. J., Wolterman, R. A., Loonen, M. C., Busch, H. F., Visser, W. J. and Bolhuis, P. A. (1984). "Uptake and stability of human and bovine acid alpha-glucosidase in cultured fibroblasts and skeletal muscle cells from glycogenosis type II patients." *Experimental Cell Research* 155: 178–189).

Any lysosomal enzyme that uses the M6P transport system can be treated according to the method of the present invention. Examples include α-glucosidase (Pompe Disease), α-L-iduronidase (Hurler Syndrome), α-galactosidase A (Fabry Disease), arylsulfatase (Maroteaux-Lamy Syndrome), N-acetylgalactosamine-6-sulfatase or β-galactosidase (Morquio Syndrome), iduronate 2-sulfatase (Hunter Syndrome), ceramidase (Farber Disease), galactocerebrosidase (Krabbe Disease), β-glucuronidase (Sly Syndrome), Heparan N-sulfatase (Sanfilippo A), N-Acetyl-α-glucosaminidase (Sanfilippo B), Acetyl CoA-α-glucosaminide N-acetyl transferase, N-acetyl-glucosamine-6 sulfatase (Sanfilippo D), Galactose 6-sulfatase (Morquio A), Arylsulfatase A, B, and C (Multiple Sulfatase Deficiency), Arylsulfatase A Cerebroside (Metachromatic Leukodystrophy), Ganglioside (Mucolipidosis IV), Acid β-galactosidase $G_{M1}$ Galglioside ($G_{M1}$ Gangliosidosis), Acid β-galactosidase (Galactosialidosis), Hexosaminidase A (Tay-Sachs and Variants), Hexosaminidase B (Sandhoff), α-fucosidase (Fucsidosis), α-N-Acetyl galactosaminidase (Schindler Disease), Glycoprotein Neuraminidase (Sialidosis), Aspartylglucosamine amidase (Aspartylglucosaminuria), Acid Lipase (Wolman Disease), Acid Ceramidase (Farber Lipogranulomatosis), Lysosomal Sphingomyelinase and other Sphingomyelinase (Nieman-Pick).

Methods for treating any particular lysosomal hydrolase with the enzymes of the present invention are within the skill of the artisan. Generally, the lysosomal hydrolase at a concentration of about 10 mg/ml and GlcNAc-phosphotransferase at a concentration of about 100,000 units/mL are incubated at about 37° C. for 2 hours in the presence of a buffer that maintains the pH at about 6–7 and any stabilizers or coenzymes required to facilitate the reaction. Then, phosphodiester α-GlcNAcase is added to the system to a concentration of about 1000 units/mL and the system is allowed to incubate for about 2 more hours. The modified lysosomal enzyme having highly phosphorylated oligosaccharides is then recovered by conventional means.

In a preferred embodiment, the lysosomal hydrolase at 10 mg/ml is incubated in 50 mm Tris-HCl, pH 6.7, 5 mM $MgCl_2$, 5 mM $MnCl_2$, 2 mM UDP-GlcNAc with GlcNAc phosphotransferase at 100,000 units/mL at 37° C. for 2 hours. Phosphodiester α-GlcNAcase, 1000 units/mL, is then added and the incubation continued for another 2 hours. The modified enzyme is then repurified by chromatography on Q-Sepharose and step elution with NaCl.

Methods for Obtaining High Mannose Lysosomal Hydrolases

High mannose lysosomal hydrolases for treatment according to the present invention can be obtained from any convenient source, e.g., by isolating and purifying naturally occurring enzymes or by recombinant techniques for the production of proteins. High mannose lysosomal hydrolases can be prepared by expressing the DNA encoding a particular hydrolase in any host cell system that generates a oligosaccharide modified protein having high mannose structures, e.g., yeast cells, insect cells, other eukaryotic cells, transformed Chinese Hamster Ovary (CHO) host cells, or other mammalian cells.

In one embodiment, high mannose lysosomal hydrolases are produced using mutant yeast that are capable of expressing peptides having high mannose structures. These yeast include the mutant *S. cervesiae* Δoch1 , Δmnn1 (Nakanishi-Shindo, Y., Nakayama, K. I., Tanaka, A., Toda, Y. and Jigami, Y. (1993). "Structure of the N-linked oligosaccharides that show the complete loss of α-1,6-polymannose outer chain from och1, och1 mnn1, and och1 mnn1 alg3 mutants of *Saccharomyces cerevisiae.*" *Journal of Biological Chemistry* 268: 26338–26345).

Preferably, high mannose lysosomal hydrolases are produced using over-expressing transformed insect, CHO, or other mammalian cells that are cultured in the presence of certain inhibitors. Normally, cells expressing lysosomal hydrolases secrete acid α-glucosidase that contains predominantly sialylated biantenniary complex type glycans that do not serve as a substrate for GlcNAc-phosphotransferase and therefore cannot be modified to use the M6P receptor.

According to the present invention, a new method has been discovered for manipulating transformed cells containing DNA that expresses a recombinant hydrolase so that the cells secrete high mannose hydrolases that can be modified according to the above method. In this method, transformed cells are cultured in the presence of α1,2-mannosidase inhibitors and the high mannose recombinant hydrolases are recovered from the culture medium. Inhibiting alpha 1,2-mannosidase prevents the enzyme from trimming mannoses and forces the cells to secrete glycoproteins having the high mannose structure. High mannose hydrolases are recovered from the culture medium using known techniques and treated with GlcNAc-phosphotransferase and phosphodiester α-GlcNAcase according to the method herein to produce hydrolases that have M6P and can therefore bind to membrane M6P receptors and be taken into the cell. Preferably, the cells are CHO cells and the hydrolases are secreted with the $MAN7(D_2D_3)$ structure. FIG. 3 shows the reaction scheme for this method.

In a preferred embodiment, recombinant human acid alpha glucosidase ("rh-GAA") is prepared by culturing CHO cells secreting rh-GAA in Iscove's Media modified by the addition of an alpha 1,2-mannosidase inhibitor. Immunoprecipitation of rh-GAA from the media followed by digestion with either N-glycanase or endoglycosidase-H demonstrates that in the presence of the alpha 1,2-mannosidase inhibitor the rh-GAA retains high mannose structures rather than the complex structures found on a preparation secreted in the absence of the inhibitor. The secreted rh-GAA bearing high mannose structures is then purified to homogeneity, preferably by chromatography beginning with ion exchange chromatography on ConA-Sepharose, Phenyl-Sepharose and affinity chromatography on Sephadex G-100. The purified rh-GAA is then treated in vitro with GlcNAc-phosphotransferase to convert specific mannoses to GlcNAc-phospho-mannose diesters. The GlcNAc-phosphomannose diesters are then converted to M6P groups by treatment with phosphodiester α GlcNAcase. Experiments show that 74% of the rh-GAA oligosaccharides were phosphorylated, 62% being bis-phosphorylated, and 12% monophosphorylated. Since each molecule of rh-GAA contains 7 N-linked oligosaccharides, 100% of the rh-GAA molecules are likely to contain the mannose-phosphate modification.

Any alpha 1,2-mannosidase inhibitor can function in the present invention. Preferably, the inhibitor is selected from the group consisting of deoxymannojirimycin (dMM), kifunensine, D-Mannonolactam eamidrazone, and N-butyl-deoxymannojirimycin. Most preferably the inhibitor is deoxymannojimycin.

Treatment of Lysosomal Storage Diseases

In a further aspect, the present invention provides a method for the treatment of lysosomal storage diseases by administering a disease treating amount of the highly phosphorylated lysosomal hydrolases of the present invention to a patient suffering from the corresponding lysosomal storage disease. While dosages may vary depending on the disease and the patient, the enzyme is generally administered to the patient in amounts of from about 0.1 to about 1000 milligrams per 50 kg of patient per month, preferably from about 1 to about 500 milligrams per 50 kg of patient per month. The highly phosphorylated enzymes of the present invention are more efficiently taken into the cell and the lysosome than the naturally occurring or less phosphorylated enzymes and are therefore effective for the treatment of the disease. Within each disease, the severity and the age at which the disease presents may be a function of the amount of residual lysosomal enzyme that exists in the patient. As such, the present method of treating lysosomal storage diseases includes providing the highly phosphorylated lysosomal hydrolases at any or all stages of disease progression.

The lysosomal enzyme is administered by any convenient means. For example, the enzyme can be administered in the form of a pharmaceutical composition containing the enzyme and any pharmaceutically acceptable carriers or by means of a delivery system such as a liposome or a controlled release pharmaceutical composition. The term "pharmaceutically acceptable" refers to molecules and compositions that are physiologically tolerable and do not typically produce an allergic or similar unwanted reaction such as gastric upset or dizziness when administered. Preferably, "pharmaceutically acceptable" means approved by a regulatory agency of the Federal or a state government or listed in the U.S. Pharmacopoeia or other generally recognized pharmacopoeia for use in animals, preferably humans. The term "carrier" refers to a diluent, adjuvant, excipient, or vehicle with which the compound is administered. Such pharmaceutical carriers can be sterile liquids, such as saline solutions, dextrose solutions, glycerol solutions, water and oils emulsions such as those made with oils of petroleum, animal, vegetable, or synthetic origin (peanut oil, soybean oil, mineral oil, or sesame oil). Water, saline solutions, dextrose solutions, and glycerol solutions are preferably employed as carriers, particularly for injectable solutions.

The enzyme or the composition can be administered by any standard technique compatible with enzymes or their compositions. For example, the enzyme or composition can be administered parenterally, transdermally, or transmucosally, e.g. orally or nasally. Preferably, the enzyme or composition is administered by intravenous injection.

The following Examples provide an illustration of embodiments of the invention and should not be construed to limit the scope of the invention which is set forth in the appended claims. In the following Examples, all methods described are conventional unless otherwise specified.

EXAMPLES

Materials and Methods

Lactating bovine udders were obtained from Mikkelson Beef, Inc. (Oklahoma City, Okla.). Ultrasphere ODS columns were obtained from Beckman Instruments. Microsorb MV-NH$_2$ columns were obtained from Rainin Instrument Co., Inc. (Woburn, Mass.). [$\gamma^{32}$P]ATP (7000 Ci/mmol; end labeling grade), Na$^{125}$I, and Lubrol (C$_{16}$H$_{33}$(CH$_2$CH$_2$O)$_{23}$H) were obtained from ICN (Costa Mesa, Calif.). Superose 6 (prep grade), DEAE-Sepharose FF, QAE-Sephadex A-25, molecular mass standards for SDS-PAGE, HiTrap-protein G columns, and Mono Q columns were obtained from Pharmacia Biotech Inc. 3M-Emphaze Biosupport Medium AB1, IODO GEN iodination reagent, and the BCA protein assay reagent were obtained from Pierce. Glycerol, sucrose, α-methylmannoside, α-methylglucoside, reactive green 19-agarose, sodium deoxycholate, benzamidine, UDP-GlcNAc, phenylmethylsulfonyl fluoride, Tris, rabbit anti-mouse IgG, and mouse monoclonal antibody isotyping reagents were obtained from Sigma.

POROS 50 HQ was obtained from Perseptive Biosystems (Cambridge, Mass.). ProBlott polyvinylidene difluoride membranes were obtained from Applied Biosystems Inc. (Foster City, Calif.). A Model QT12 rotary tumbler was obtained from LORTONE, Inc. (Seattle, Wash.). A mouse immunoglobulin standard panel was obtained from Southern Biotechnology Associates, Inc. (Birmingham, Ala.). Recombinant interleukin-6, porcine uteroferrin, and monoclonal antibody BP95 were gifts from colleagues. Other chemicals were reagent grade or better and were from standard suppliers.

Example 1

Preparation of Monoclonal Antibodies Specific for Bovine GlcNAc-phosphotransferase Bovine GlcNAc-phosphotransferase was partially purified 30,000 fold as described (Bao, M., Booth J. L., et al. (1996). "Bovine UDP-N-acetylglucosamine: Lysosomal enzyme N-acetylglucosamine-1-phosphotransferase. I. Purification and subunit structure." *Journal of Biological Chemistry* 271: 31437–31445) and used to immunize mice. Spleens of immune mice were removed and spenocytes fused with SP2/0 myeloma cells according to Harlow (Harrow, E. and Lane, D. (1988). *Antibodies: a laboratory manual,* Cold Spring Harbor Laboratory). The fusion was plated into 96 well plates and cultured in HAT media until hybridomas were visible.

Hybridomas secreting monoclonal antibodies capable of capturing GlcNAc-phosphotransferase from a crude sample were identified by incubation of hybridoma media (200 μl) with 200 units. Partially purified GlcNAc-phosphotransferase and capturing the resulting immune complex on rabbit anti-mouse IgG bound to protein A coupled to Ultralink™ matrix. Immune complexes which contained monoclonal antibodies directed against GlcNAc-phosphotransferase were then identified by assay of the immune complex for GlcNAc-phosphotransferase activity. By this strategy, four monoclonals directed against GlcNAc-phosphotransferase were identified in the fifth fusion screened. The hybridomas identified were subcloned twice using the same assay and ascites was produced in BALBc mice according to standard techniques (Harlow, E. and Lane, D. (1988). *Antibodies: a laboratory manual,* Cold Spring Harbor Laboratory). The monoclonal antibody labeled PT18 was selected for use in further experiments.

Example 2

Purification of Bovine GlcNAc-phosphotransferase

Lactating bovine mammary gland (6 kg) was collected at slaughter and immediately sliced into 10 cm thick slices and chilled in ice. Following homogenization in a Waring commercial blender, the post-nuclear supernatant fraction was prepared by centrifugation. Membrane fragments were collected by high speed centrifugation (39,000×g, 45 minutes) and membrane proteins were solubilized in 4% Lubrol, 0.5% deoxycholate. GlcNAc-phosphotransferase was specifically adsorbed from the solubilized membrane fraction by incubation overnight with 10 ml of monoclonal antibody PT 18 coupled to Ultralink™ matrix (substitution 5 mg/ml). The matrix was then collected by low speed centrifugation, washed with 0.025 M Tris-HCl, pH 7.4, 0.005 M MgCl$_2$, 0.3% Lubrol buffer containing 1 M NaCl. The column was then washed with 2 column volumes of 0.01 M Tris-HCl, pH 7.4, 0.005 M MgCl$_2$, 0.3% Lubrol buffer. GlcNAc-phosphotransferase was then eluted from the column with 0.10 M Tris-HCl, pH 10.0, 0.005 M MgCl$_2$, 0.3% Lubrol and neutralized with ¹/₁₀th volume of 1 M Tris-HCl, pH 6.0. Recovery is typically 20–50% of the GlcNAc-phosphotransferase activity present in the homogenized tissue, and approximately 0.5 mg of enzyme is recovered per 10 kg of tissue processed.

Example 3

Amino Acid Sequencing of Bovine GlcNAc-phosphotransferase

Example 3A

Reduction, Alkylation and Separation of Individual Subunits

Bovine GlcNAc-phosphotransferase, 1.9 mg was desalted on a column of Sephadex G-25 superfine equilibrated in 9% formic acid and lyophilized. The lyophilized protein was dissolved in 1 ml of 500 mM Tris-HCl, pH 8.6, 6 M guanidine-HCl, 10 mM EDTA, 2 mM DTT degassed by bubbling N₂ gas through the solution and incubated at 37° C. for 1 hour. The solution was made 5 mM in iodoacetic acid and incubated at 37° C. in the dark for a further 2½ hours. The solution was then made 15 mM in β-mercaptoethanol and chromatographed on a column of Sephadex G-25 superfine equilibrated in 9% formic acid. The void fraction was pooled and lyophilized. The individual subunits were resolved by chromatography on a 1.0×30 cm column of Superose 12 equilibrated with 9% formic acid.

Example 3B

Amino Terminal Sequencing of Individual Subunits

Bovine GlcNAc-phosphotransferase, 0.5 mg was equilibrated with sodium dodecyl sulfate, electrophoresed on a 6% polyacrylamide gel in the presence of sodium dodecyl sulfate. The resolved subunits were then electro-transferred to a PVDF membrane and the protein bands detected by staining with Coomassie Blue. The bands corresponding to the individual subunits were then excised with a razor blade and subjected to amino-terminal sequencing in an Applied Biosystems Model 492 protein sequencer. The amino terminal sequence of the α-subunit was Met Leu Leu Lys Leu Leu Gin Arg Gin Arg Gin Thr Tyr (SEQ ID NO:26). The amino terminal sequence of the β Subunit is Asp Thr Phe Ala Asp Ser Leu Arg Tyr Val Asn Lys Ile Leu Asn Ser Lys Phe Gly Phe Thr Ser Arg Lys Val Pro Ala His (SEQ ID NO:27). The amino terminal sequence of the γ-subunit is Ala Lys Met Lys Val Val Glu Glu Pro Asn Thr Phe Gly Leu Asn Asn Pro Phe Leu Pro Gin (SEQ ID NO:28).

Example 3C

Internal Amino Acid Sequence of the β- and γ-subunits

The resolved β- and γ-subunits from example 3B were treated with trypsin at a 1/40 mass ratio overnight at 37° C. in 0.1 M Tris-HCI, pH 8.0. The tryptic fragments were then resolved by reverse phase chromatography on a C18 column equilibrated with 0.1% trifluoroacetic acid and developed with a linear gradient in acetonitrile. Well resolved peaks were then subjected to amino terminal sequencing as described in example 3B. The peptides sequenced from the β-subunit had the sequences Ile Leu Asn Ser Lys (SEQ ID NO:29), Thr Ser Phe His Lys (SEQ ID NO:30), Phe Gly Phe The Ser Arg (SEQ ID NO:31), and Ser Leu Val Thr Asn Cys Lys Pro Val Thr Asp Lys (SEQ ID NO:32). The peptide sequenced from the γ-subunit had the sequence Leu Ala His Val Ser Glu Pro Ser Thr Cys Val Tyr (SEQ ID NO:33). A second peptide sequence from the γ-subunit was obtained by chymotryptic digestion with the sequence Asn Asn Pro Phe Leu Pro Gln Thr Ser Arg Leu Gin Pro (SEQ ID NO:34).

Example 3D

Internal Amino Acid Sequence of the α-subunit

Internal peptide sequences of the α-subunit were obtained as follows. Bovine GlcNAc phosphotransferase was reduced, alkylated, electrophoresed and transferred to PVDF as previously described. The α-subunit band was excised and tryptic peptides generated by in situ digestion with trypsin, eluted with acetonitrile/trifluoroacetic acid and fractionated by reverse phase HPLC. Individual peaks were then examined by Matrix Associated Laser Desorption-Ionization-Mass Spectroscopy (MALDI-MS) and peaks containing a single mass were subjected to amino terminal sequencing as above. The peptide sequences determined from the α-subunit are Val Pro Met Leu Val Leu Asp Xaa Ala Xaa Pro Thr Xaa Val Xaa Leu Lys (SEQ ID NO:35) and Glu Leu Pro Ser Leu Tyr Pro Ser Phe Leu Ser Ala Ser Asp Val Phe Asn Val Ala Lys Pro Lys (SEQ ID NO:36).

Example 4

Cloning the Human GlcNAc-phosphotransferase α/β-subunit cDNA

The amino-terminal protein sequence determined from the isolated bovine β-subunit was used to search the Expressed Sequence Tag (EST) data base using the program tblastn. Altschul, S. F., Gish W., et al. (1990). "Basic Local Alignment Search Tool." *Journal of Molecular Biology* 215: 403–410. This search identified a partial mouse cDNA previously identified during a positional cloning strategy. Cordes, S. P. and Barsh, G. S. (1994). "The mouse segmentation gene kr encodes a novel basic domain-leucine zipper transcription factor." *Cell* 79: 1025–11034.

A forward PCR primer was designed based on the mouse sequence and used with an oligo dT reverse primer for RT-PCR amplification of a 1,848 bp product using mouse liver poly A RNA as template. The PCR product was cloned and sequenced and proved to contain all the determined β-subunit sequences, demonstrating it encoded the murine β-subunit.

The human β-subunit cDNA was cloned by screening a size selected human placental cDNA library (Fischman, K., Edman J. C., et al. (1990). "A murine fer testis-specific transcript (ferT encodes a truncated fer protein." *Molecular and Cellular Biology* 10: 146–153) obtained from ATCC with the random hexamer labeled murine β-subunit cDNA under conditions of reduced stringency (55° C., 2×SSC). The remaining portion of the α/β-subunit precursor cDNA was cloned by a combination of a walking strategy beginning with the portion of the cDNA encoding the human β-subunit and standard library screening strategies. Additionally, EST data base searches were used to identify clones containing portions of the human α/β cDNA, which were obtained from the corresponding repositories and sequenced. Together these strategies allowed the determination of the full length human α/β-subunits precursor cDNA sequence. A clone containing this sequence was assembled using the appropriate fragments and cloned into pUC19. The 5597 bp sequence is given in Sequence NO:4 and contains DNA sequences predicted to encode protein sequences homologous to all of the amino terminal and internal peptide sequences determined from the bovine α- and β-subunits.

Example 5

Cloning the Human GlcNAc-phosphotransferase γ-subunit cDNA

The γ-subunit amino terminal and tryptic peptide sequences were used to search the Expressed Sequence Tag (EST) data base using the program tblastn. Altschul, S. F., Gish W., et al. (1990). "Basic Local Alignment Search Tool." *Journal of Molecular Biology* 215: 403–10. Three human EST sequences were identified which were highly homologous to the determined bovine protein sequences. cDNA clone 48250 from which EST sequence 280314 was determined was obtained from Genome Systems and sequenced using standard techniques. This clone contained a 1191 bp insert which contained all the determined protein sequences and appeared to contain a signal sequence 5' of the determined amino terminal sequence. The clone however lacked an initiator methionine or any 5' non-coding sequence. The 5' portion of the cDNA was obtained by PCR. the reverse primer 5'GCGAAGATGAAGGTGGTGGAGGACC-3' (SEQ ID NO:37) and a T7 promoter primer were used in a reaction along with template DNA from a human brain cDNA library in pCMV-SPORT(GIBCO). A 654 bp product was obtained, cloned in pCR2.1 and sequenced. The sequence demonstrated the amplified product contained 23 bp of 5' non-coding sequence, the initiator methionine and the signal peptide identified in EST 280314. A full length cDNA for the γ-subunit (pBC36) was assembled by ligating a 75 bp EcoRI-ApaI fragment from the cloned PCR product, an ApaI-NotI fragment from clone 48250 and EcoRI-NotI cut pcDNA3 (Invitrogen).

Example 6

Cloning the Human GlcNAc-phosphotransferase α/β-subunit Gene

Plasmid DNA was prepared from a human brain cDNA library (Life Technologies) according to the manufacturers protocol. This DNA was used as template for PCR using primers with the sequences 5'-TGCAGAGACAGACCTATACCTGCC-3' (SEQ ID NO:38) and 5' ACTCACCTCTCCGAACTG-GAAAG-3' (SEQ ID NO:39) using Taq DNA polymerase and buffer A from Fischer Scientific using 35 cycles of 94° C. 1 minute, 55° C. 1 minute, and 79° C. 1 minute. A 106 bp product was obtained, purified by agarose gel electrophoresis, isolated by GeneClean (Bio101) and cloned into pCR2. DNA sequencing determined the resulting plasmid pAD39 contained a 106 bp insert which was excised by digestion with EcoRI and submitted to Genome Systems for screening of a human genomic BAC library. Four human BACs were identified and BAC #14951 was sequenced. For sequencing BAC #14951 was submitted to a colleague's laboratory at the University of Oklahoma. The BAC was then fragmented by nebulization, and fragments cloned into pUC18 and shotgun sequenced. Contigs were generated by computer analysis and gaps closed by primer walking strategies. The sequence of the BAC spans 177,364 bp. The GlcNAc-phosphotransferase α/β-subunits precursor gene spans ~80 kb and is arranged as 21 exons.

Example 7

Cloning the Human GlcNAc-phosphotransferase γ-subunit Gene

The human γ-subunit gene was identified by blastn searching of the NCBI High Throughput Genomic Sequence (HGTS) database with the full length human Subunit cDNA sequence. The search identified a clone HS316G12(gi 4495019) derived from human chromosome 16 which contained the human γ-subunit gene. The human GlcNAc-phosphotransferase γ-subunit gene spans about 12 kb and is arranged as 11 exons. Exons 1–3 and 4–11 are separated by a large intron of about 9 kb.

Example 8

Preparation of Modified Expression Plasmid for the Human GlcNAc-phosphotransferase α/β-subunits Precursor cDNA An expression vector for the GlcNAc-phosphotransferase α/β cDNA was constructed in pcDNA3.1(+) as follows. Two upstream ATG's in the 5'-noncoding sequence of the human GlcNAc-phosphotransferase cDNA were removed and the Kozak sequence were modified as follows. Two fragments from pAD98, which was the human GlcNAc-phosphotransferase α/β cDNA cloned into pcDNA3.1(+), were excised. A 1068 bp XhoI-PstI fragment and a 9746 bp NheI-XhoI fragment were ligated with oligonucleotides with sequences 5'-CTAGCCACCATGGGGTTCAAGCTCTTGCA-3' (SEQ ID NO:40) and 5'-AGAGCTTGAACCCCATGGTGG-3' (SEQ ID NO:41) generating pAD105. The poly A sequence near the 3' end of the cDNA clone was removed by ligating a NheI-BglII fragment from the cDNA with NheI-BamHI cut vector pcDNA3.1(+) generating pAD128.

Example 9

Preparation of an Expression Plasmids for the Human GlcNAc-phosphotransferase α/β Subunits Precursor cDNA DNA sequencing of pAD128 identified deletion of an A in an AAAAA sequence (positions 2761–2765 shown in SEQ ID NO:4) that disrupted the coding sequence. Plasmid pAD130 was constructed in an attempt to correct this by ligating a 5929 bp NheI-MfeI fragment and a 2736 bp NheI-AgeI fragment (both from pAD128 with a 515 bp MfeI-AgeI fragment derived from pAD124). Plasmid pAD130 was then grown and subsequent sequencing of plasmid pAD130 demonstrated that the AAAAA sequence had reverted to AAAA again indicating instability in the sequence at this point.

In order to eliminate this instability the first AAA (position 2761–2763 shown in SEQ ID NO:4) that codes for lysine was changed to AAG (also coding for lysine) so that the unstable AAAAA sequence was changed to a stable AAGAA without altering the encoded amino acid. Plasmid pAD130 was corrected by removing a 214 bp MfeI-DraIII fragment and replacing it with a fragment with the correct sequence. The correct MfeI-DraIII fragment was prepared by PCR using pAD130 as a template with forward primer 5'-GAAGACACAATTGGCATACTTCACTGATAGC <u>AAGAA</u>TACTGGGAGGC AACTAAAAGATAC-3' (SEQ ID NO:42) (oligo TTI 25 with desired AAGAA sequence as underlined) and reverse primer 5'-ACTGCATATCCTCAGAATGG-3' (SEQ ID NO:43) (oligo TTI 24). The PCR fragment was subcloned into the EcoRV site of pBluescript KS II(+) (Stratagene) generating pMK16. The insert was sequenced for confirmation and the 215 bp MfeI-DraIII fragment was prepared. To avoid MfeI-DraIII sites on the vector pcDNA 3.1(+) (Invitrogen), the NheI-XbaI fragment was prepared from pAD130 and subcloned into the XbaI site of pUC19 (Life Technologies) to construct pMK15. pMK15 was cleaved with MfeI and DraIII and the 6317 bp fragment was purified and ligated with the MfeI-DraIII fragment from pMK16 to form pMK19 containing the desired stable sequence in pUC19.

The corrected cDNA for the α/β subunit was excised from pMK19 as a KpnI-XbaI fragment and subcloned between the KpnI and XbaI sites of pcDNA6/V5/His-A and designated pMK25. Plasmid pMK25 containing the cDNA as shown in SEQ ID NO:20 where the nucleotide sequence for the modified human α/β-subunit precursor cDNA is shown in nucleotides 1–3768. This sequence corresponds to and is a modification of the nucleotide sequence 165–3932 shown in SEQ ID NO:4.

Example 10

Construction of Expression Vectors for Soluble, Human GlcNAc-phosphotransferase α/β Subunits Precursor cDNA Plasmid pMK19 was digested with BglII (cutting at positions 255 and 2703 shown in SEQ ID NO:20) and self-ligated to reduce the length of the cDNA to be amplified from approx. 3.5 kb to 1 kb so that the 5' and 3' ends of the cDNA can be modified by PCR to remove the transmembrane domains of the α and β subunits of human GlcNAc-phosphotransferase and used to construct expression vectors to produce soluble GlcNAc-phosphotransferase. This plasmid was designated pMK21. The strategy is that the nucleotides encoding the first 44 amino acids containing the transmembrane domain of the α subunit (nucleotides 1–132 of SEQ ID NO:20) are replaced with a HindIII site, and nucleotides encoding the last 47 amino acids containing the transmembrane domain of the β subunit (nucleotides 3628–3768 of SEQ ID NO:21) are replaced with a stop codon and a XbaI site.

Plasmid pMK21 was used as a template for PCR with the following primers: A forward primer (5'-TGGTTCTG AAGCTTAGCCGAGATCAATACCATG-3' (SEQ ID NO:44), oligo TTI 76) containing a HindIII site (underlined) and a sequence complementary to nucleotides 133 to 151 of SEQ ID NO:20 (italics), which will produce the 5'-end of a PCR fragment that removes the coding sequence of the first 44 amino acids comprising the putative transmembrane domain of the α subunit. A reverse primer (5'-TAGTACAC TCTAGActactaCTTCAATTTGTCTCGATAAG-3' (SEQ ID NO:45), oligo TTI 78) containing a XbaI site (underlined), two stop codons (lower case) and a sequence complementary to nucleotides 3608 to 3627 of SEQ ID NO:21 (italics), which will produce the 3'-end of a PCR fragment that removes the coding sequence of the last 47 amino acids comprising the putative transmembrane domain of the β subunit and replaces it with two stop codons. The resulting PCR fragment was subcloned into the EcoRV site of pBluescript KS II+(Stratagene). This plasmid, designated pMK42, was sequenced to ensure no errors were introduced by PCR. The BglII-BglII fragment (positions 255–2703 shown in SEG ID NO:20) which was previously removed was subcloned back into the BglII site of pMK42. The orientation of this fragment was determined to be correct and this plasmid was designated pMK49. Thus, plasmid pMK49 contained a cDNA comprising a 5' HindIII site and a 3' XbaI site flanking a coding region for the human GlcNAc-phosphotransferase α/β subunits precursor cDNA with the α subunit putative transmembrane domain deleted and the putative transmembrane domain of the β subunit replaced with two stop codons (soluble α/β-cDNA).

This "soluble α/β-cDNA" can now be conveniently subcloned into vectors constructed to contain the HPC4 epitope (used for rapid purification of the soluble enzyme) and different secretion signal peptides. These pcDNA6/V5/His-A+tag) vectors were constructed as follows:

Synthetic oligonucleotide cassettes containing a 5'-NheI site and a 3'-HindIII site flanking nucleotide sequences coding for different secretion signal peptides and the nucleotide sequence coding for the HPC4 epitope were inserted into plasmid pcDNA6/V5/His-A cut with NheI and HindIII. The following plasmids were prepared with the indicated cassette:

1. pMK45—mouse immunoglobulin Kappa chain signal peptide (sequence in italics) and HPC4 epitope (sequence underlined)

```
CTAGCCGCCACC ATGGAGACAGACACACTC CTGCTATGGGTACTGCTGCTC      (SEQ ID NO:46)
    GGCGGTGGTACC TC TGTCT GTGTGAGGACGATACCCATGACGACGAG
TGGGTTCC AGGT TC CACTGGTGA CGAAGATCAGGTAGATCCGCGGTT AATC
ACCCAAGGTCCAAGGTGACCACTGCTTC TAGTCCAT CTAGGCGCCAATTAG
GACGGTA
CT GCCATTCGA
```

1. pMK44—a transferrin signal peptide sequence (in italics) and HPC4 epitope (sequence underlined)

```
CTAGCGGTACCATGAGATT AGCAGTAGGCGCC TT ATTAG TATGCGC AGTACT C   (SEQ ID NO:47)
    CGCCATGGTACTCTAATCGTCATCCGCGGAATAATCATACGCGTCATGAG
GGATTAT GTC TCGCAG AAGATCAGGTAGATCCGC GGTT AATCGACGGTA
CCTTATACAGAGCGTCTTCTAG TCCAT CTAGGCGCCAAT TAGCTGCCATTCGA
```

1. pMK43—a transferrin secretion peptide sequence modified to satisfy a Kozak's sequence(sequence in italics) and HPC4 epitope (sequence underlined),

```
CTAGCCGCCACCATGGGATT AGCAGTAGGCGCCTT ATT AGT ATGCGC AGT     (SEQ ID NO:48)
   CGCCGGTGGTACCCTAATCGTCATCCGCGGAATAATCATACGCGTCA
ACT CGGATTAT GT C TCGCA GAAGATCAGGTAGATCCGC GGTTAATCGACG
TGAGCCTAATACAGAGCGTCTT CTAGT CCATCTAGGCGCCAAT TAGCTGC
GTA
CATTCGA
```

The cDNA encoding "soluble α/β subunits" can be obtained as a HindIII-XbaI fragment from pMK49 and inserted into the plasmid pMK43 to form pMK50; pMK44 to form pMK51, and into pMK45 to form pMK52, plasmids capable of encoding the α/β subunits of human GlcNAc-phosphotransferase with putative transmembrane domains deleted, with different signal peptides and all having the HPC4 epitope tag to facilitate purification of the soluble, secreted enzyme.

Example 11

Construction of Expression Vectors for the Human GlcNAc-phosphotransferase γ Subunit Precursor cDNA The human GlcNAc-phosphotransferase γ-subunit precursor cDNA was obtained from plasmid pAD133 in pAC5.1/V5-His by cutting with EcoRI. This cDNA was inserted into EcoRI digested pcDNA6/V5/His-A to form plasmid pMK17 containing cDNA as shown in SEQ ID NO:5. Plasmid pMK17 was digested with MluI (position 124–129 as shown in SEQ ID NO:5) and EcoRI (position 1103–1108 as shown in SEQ ID NO:5) and the 980 bp MluI-EcoRI fragment was then subcloned in pBluescriptKSII(+) with a synthetic double stranded cassette having an HindIII site and a MluI site flanking a nucleotide sequence including positions corresponding to 95–123 as shown in SEQ ID NO:5 thereby removing the nucleotide sequence encoding the amino terminal, 24-amino acid signal peptide in plasmid pMK26. Plasmid pMK26 was sequenced to ensure its sequence. The correct cDNA from pMK26, which encodes amino acids for the human GlcNAc-phosphotransferase γ subunit with the signal peptide removed, is then excised from pMK26 by HindIII and EcoRI digestion and placed into plasminds pMK43 to form pMK58; pMK44 to form pMK59, and into pMK45 to form pMK64, plasmids capable of encoding the γ subunit of human GlcNAc-phosphotransferase with its signal peptide deleted, with different signal peptides and all having the HPC4 epitope tag to facilitate purification of the soluble, γ subunit.

To evaluate the behavior of α/β/γ secreted products, the α/β subunit precursor and the γ subunit were co-expressed in the bi-cistronic vector pIRES (Clontech). This was accomplished by subcloning α/β and γ cDNAs expressing the desired subunit with a selected signal peptide and the HPC4 Tag into NheI site (MCS-A) and XbaI site (MCS-B) of pIRES, respectively.

Example 12

Transient Expression of the α/β and γ Subunits of Human GlcNAc-phosphotransferase in 293T Cells Plasmids were transfected into 293T cells using Fugene6 (Roche) according to manufacturer's instructions. Culture media was collected 23 h, 44.5 h and 70 h after transfection. Aliquots of media containing expressed protein was captured on anti-HPC4 monoclonal antibody (U.S. Pat. No. 5,202,253) conjugated with Ultralink beads (Pierce) by overnight incubation at 4° C. The beads were washed to remove unbound protein and assayed directly for phosphotransferase activity as described previously (REF).

Plasmids used for expression all containing a sequence encoding for the HPC4 tag were as follows:
1. pMK50—modified transferrin secretion peptide and α/β subunit in pcDNA6/V5/His4
2. pMK51—transferrin secretion peptide and α/β subunit in pcDNA6/V5/His4
3. pMK52—mouse immunoglobulin secretion peptide and α/β subunit in pcDNA6/V5/His4
4. pMK75—modified transferrin secretion peptide and α/β subunit and modified transferrin secretion peptide and γ subunit in pIRES
5. pMK81—transferrin secretion peptide and α/β subunit and transferrin secretion peptide and γ subunit in pIRES
6. pMK76—mouse immunoglobulin secretion peptide and α/β subunit and mouse immunoglobulin secretion peptide and γ in pIRES The relative amounts of expression detected by assay for phosphotransferase using methyl-α-D-mannoside and UDP-[P-$^{32}$P]-GlcNAc as substrates with cell transfected with pcDNA6/V5/His-4 as controls is shown in FIG. 4.

Example 13

Expression and Purification GlcNAc-phosphotransferase α/β/γ

For expression and purification of the enzyme, a modified expression plasmid is constructed in a modified expression vector derived from pEE14. The plasmid directs the synthesis of a soluble epitope tagged GlcNAc-phosphotransferase molecule. The α/β-subunit precursor is modified as follows: The 5' portion of the cDNA which encodes the α-subunit cytoplasmic and transmembrane domain is deleted and replaced with nucleotides which encode the transferrin signal peptide followed by amino acids which encode the epitope for monoclonal antibody HPC4. The 3' portion of the cDNA is modified by the insertion of a stop codon before the β-subunit transmembrane segment. The vector pEE14.1 (Lonza Biologics) is modified by the insertion of a 850 bp MluI-NcoI fragment containing a modified vascular endothelial growth factor (VEGF) promoter at the unique MluI site in pEE14.1 This vector encoding the modified GlcNAc-phosphotransferase α/β-subunit precursor is co-transfected with a wild type γ-subunit construct containing the VEGF promoter in pEE14. 1 into CHO-K1 cells using Fugene6 and plated into 96 well plates. Transfectants are selected in 25 μm methionine sulfoximine and the plasmid amplified by selection in 96 well plates with 50 μM, 100 μM, 250 μM, and 500 μM methionine sulfoximine. Clones are picked into duplicate 96 well plate and the highest expressing clones selected by dot blotting media and immuno-detection with monoclonal antibody HPC4. The highest expressing clone is expanded into cell factories. The recombinant soluble epitope tagged GlcNAc-phosphotransferase is purified from the media by chromatography on monoclonal antibody HPC4 coupled to Ultralink in the presence of 5 mM $MgCl_2$ and 1 mM $CaCl_2$. The soluble epitope tagged GlcNAc-phosphotransferase is eluted with 5 mM EGTA and 5 mM $MgCl_2$.

Example 14

Preparation of Monoclonal Antibodies Specific for Bovine Phosphodiester α-GlcNAcase Murine monoclonal antibodies specific for bovine phosphodiester α-GlcNAcase were generated by immunization of mice with a partially purified preparation of phosphodiester α-GlcNAcase. Spleens were then removed from immune mice and fused with SP2/O myeloma cells according to standard techniques (Harrow, E. and Lane, D. (1988). *Antibodies: a laboratory manual*, Cold Spring Harbor Laboratory). Hybridomas were plated in eight 96-well plates and grown until hybridomas were visible. Hybridomas secreting antibodies to phosphodiester α-GlcNAcase were identified measuring phosphodiester α-GlcNAcase activity in immunoprecipitates prepared by incubation of a partially purified preparation of phosphodiester α-GlcNAcase with pooled hybridoma supernatants. Pools from 16 and 4 wells were assayed followed by individual wells. Monoclonal UC1 was identified by this protocol and coupled to Ultralink™ for use in purification of phosphodiester α-GlcNAcase.

Example 15

Purification of Bovine Phosphodiester α-GlcNAcase

Bovine calf liver (1 kg) was homogenized in 0.05 M Imidazole-HCl, pH 7.0, 0.15 M NaCl, 0.01 M EDTA and a washed post-nuclear supernatant was prepared. Membranes were collected by centafugation at 30,000×g for 30 minutes and washed three times with the above buffer. Membrane proteins were then solubilized in buffer containing 2% Triton X-100, 0.05% deoxycholate and insoluble material removed by centrifugation, as before. The solubilized membrane fraction was incubated with 20 ml of monoclonal antibody UC1 coupled to Ultralink™ (substitution 5 mg/ml) with constant rotation for 16 hours at 4° C. The UC1-Ultralink™ was collected by low speed centrifugation packed into a column and washed with 0.025 M Tris-HCl, pH 7.4, 0.3% Lubrol, followed by two column volumes of 0.5 M NaHCO3, pH 8.0, 0.3% Lubrol. Phosphodiester α-GlcNAcase was then eluted with 0.5 M NaHCO3, pH 10.0, 0.3% Lubrol and collected in 1/10 volume of 1.0 M Tris-HCl, pH 5.5.

Example 16

Amino Acid Sequencing of Bovine Phosphodiester α-GlcNAcase

Example 16A

Amino-terminal Sequence of Bovine Phosphodiester α-GlcNAcase

Bovine phosphodiester α-GlcNAcase was bound to a 0.25 ml column of POROS HQ and step-eluted with buffer containing 0.5 M NaCl. Fractions containing phosphodiester α-GlcNAcase activity were identified by phosphodiester α-GlcNAcase assay, pooled and absorbed to a ProSorb Sample Preparation Cartridge (Perkin Elmer) and subjected to amino acid sequencing in an Applied Biosystems Model 492 Protein Sequencer operated according to the manufacturer's instructions. The sequence Asp-Xaa-Thr-Arg-Val-His-Ala-Gly-Arg-Leu-Glu-His-Glu-Ser-Trp-Pro-Pro-Ala-Ala-Gln-Thr-Ala-Gly-Ala-His-Arg-Pro-Ser-Val-Arg-Thr-Phe-Val was obtained.

Example 16B

Internal Sequence of Bovine Phosphodiester α-GlcNAcase

Bovine liver phosphodiester α-GlcNAcase was concentrated to 10 μl in a Speed Vac, combined with 30 μl 0.1 M Tris-HCl, pH 7.4, 8 M guanidine-HCl, and 2–4 μl 25 mM DTT and incubated at 50° C. for 1 hour. Iodoacetamide 2.4 μl 50 μM was then added and the incubation was continued for 1 hour. The reaction mixture was then desalted on a column of Sephadex G25 superfine as described for GlcNAc-phosphotransferase and digested with trypsin. The peptides were fractionated by HPLC and sequenced as described for GlcNAc-phosphotransferase. The sequences determined are Arg Asp Gly Thr Leu Val Thr Gly Tyr Leu Ser Glu Glu Glu Val Leu Asp Thr Glu Asn and Gly Ile Asn Leu Trp Glu Met Ala Glu Phe Leu Leu Lys.

Example 17

Cloning the Human Phosphodiester α-GlcNAcase cDNA

The phosphodiester α-GlcNAcase tryptic peptide sequences were used to search the EST data bases as described for GlcNAc-phosphotransferase above. Three EST sequences were identified which contained the human phosphodiester α-GlcNAcase cDNA and clone ATCC #367524 was obtained and a ~700 bp EcoRI-NotI fragment was excised from this clone and used to probe a human liver cDNA library in the vector TriplEx. Several clones were identified and sequenced, one of which (clone 6.5) proved to contain a nearly full length cDNA for the human phosphodiester α-GlcNAcase. The genomic clone described in Example 18 demonstrated that clone 6.5 was missing only the initiator methionine.

Example 18

Cloning the Human Phosphodiester α-GlcNAcase Gene

The human phosphodiester α-GlcNAcase gene was identified by searching the NCBI database nr with the human phosphodiester α-GlcNAcase cDNA using the program blastn. The genomic sequence was determined during the sequencing of a clone from chromosome 16p13.3 and deposited Mar. 6, 1999 in GenBank as an unidentified sequence of 161264 bp with the accession number AC007011. The gene spans about 12 kb of genomic DNA on chromosome 16.13 and is arranged in 11 exons.

Example 19

Construction of an Expression Vector for Human Phosphodiester or α-GlcNAcase An expression vector for human phosphodiester α-GlcNAcase was prepared as follows: The 5' end of the sequence of clone 6.5 was modified by PCR amplification of the 5' end of the cDNA with a forward primer with the sequence 5'-GGAATTCCACCATGGCGACCTCCACGGGTCG-3' (SEQ ID NO:49) and a reverse primer 5'-TGACCAGGGTCCCGTCGCG-3' (SEQ ID NO:49). This served to add a consensus Kozak sequence and initiator methionine to the sequence of clone 6.5. The ~500 bp PCR product was purified, digested with EcoRI and BamHI and ligated into pcDNA3.1(−) which was sequenced. This construct was then digested with BamHI and HindIII and ligated with a ~1600 bp BamHI-HindIII fragment containing the 3' portion of the cDNA from clone 6.5 generating the full length expression plasmid.

Example 20

Host Cell Preparation for Human Phosphodiester α-GlcNAcase

Cos cells were grown in 60 mm plates in Dulbeccos minimal essential media (DMEM) at 37° C. in 5% $CO_2$ until they reached 50–80% confluence. The plates were then washed with OptiMEM I and the cells transfected with the expression vector described in Example 19 using Lipofectamine Plus (GIBCO BRL Life Technologies) according to the manufacturers instructions. Cells were harvested at 48 hours, a solubilized membrane fraction prepared and assayed for phosphodiester α-GlcNAcase activity.

Example 21

Expression and Purification of Soluble Recombinant Human Phosphodiester α-GlcNAcase For expression and purification of the enzyme, a modified expression plasmid is constructed in a modified expression vector derived from pEE14.1. The plasmid directs the synthesis of a soluble epitope tagged phosphodiester α-GlcNAcase molecule. The phosphodiester α-GlcNAcase precursor is modified as follows: The 3' portion of the cDNA which encodes the phosphodiester α-GlcNAcase transmembrane and cytoplasmic domains is deleted and replaced with nucleotides which encode the epitope for monoclonal antibody HPC4 followed by a stop codon. The vector pEE14.1 (Lonza Biologics) is modified by the insertion of a 850 bp MluI-NcoI fragment containing a modified vascular endothelial growth factor (VEGF) promoter at the unique MluI site in pEE14.1. This vector encoding the epitope tagged soluble phosphodiester α-GlcNAcase precursor is transfected into CHO-K1 cells using Fugene6 and plated into 96 well plates. Transfectants are selected in 25 μm methionine sulfoximine, and the plasmid amplified by selection in 96 well plates with 50 μM, 100 μM, 250 μM, and 500 μM methionine sulfoximine. Clones are picked into duplicate 96 well plate and the highest expressing clones selected by dot blotting media and immuno-detection with monoclonal antibody HPC4. Media from clones demonstrating the highest level of epitope tag expression is assayed for phosphodiester α-GlcNAcase activity. The highest expressing clone is expanded into cell factories. The recombinant soluble epitope tagged phosphodiester α-GlcNAcase is purified from the media by chromatography on monoclonal antibody HPC4 coupled to Ultralink™ in the presence of 5 mM $MgCl_2$ and 1 mM $CaCl_2$. The soluble epitope tagged phosphodiester α-GlcNAcase is eluted with 5 mM EGTA and 5 mM $MgCl_2$.

Example 22

Construction of an Expression Vector for Soluble, Human Phosphodiester α-GlcNAcase For expression and purification of the enzyme, a modified expression plasmid is constructed in a modified expression vector derived from the pEE14.1 vector (Lonza Biologics). The plasmid directs the synthesis of a soluble epitope tagged phosphodiester α-GlcNAcase molecule. The phosphodiester α-GlcNAcase precursor is modified as follows: The 3' portion of the cDNA (1342–1548 of SEQ ID NO: 7) which encodes the phosphodiester α-GlcNAcase transmembrane and cytoplasmic domains was deleted and replaced with nucleotide sequence GAGGACCAGGTGGACCCCAG-GCTGATCCAC GGCAAGGAT (SEQ ID NO:51) that encodes the epitope for monoclonal antibody HPC4 (EDQVDPRLIDGKD (SEQ ID NO:52)) followed by a stop codon.

This expression vector was constructed by generating two intermediate plasmids and ligating a fragment from each into pEE14.1 vector (Lonza Biologics) to yield the final expression vector. The first intermediate plasmid designated pKB4 was constructed by ligating the 1034 bp FseI>>Bsu36I fragment of phosphodiester α-GlcNAcase (lacking the C-terminal transmembrane and cytoplasmic domains) from clone 6.5, and a Bsu36I-XbaI oligonucleotide fragment that contains the HPC4 epitope into a modified pUC19 vector. The second intermediate plasmid designated pKB5, was constructed by ligating a 850 bp MluI-NcoI fragment containing a modified vascular endothelial growth factor (VEGF) promoter from pcDNA4/HisMax (Invitrogen), a 256 bp BseI-FseI fragment encoding the N-terminus of human phosphodiester α-GlcNAcase from clone 6.5, and an oligonucleotide linker into a modified pUC19 vector. The final expression vector designated pKB6 was constructed by ligating the MluI-FseI fragment from pKB5, and the FseI-HindIII fragment from pKB4 into a MluI/HindIII digested pEE14.1 vector. The plasmid pKB6 contains the nucleotide sequence shown in SEQ ID NO:22.

Expression and Purification of Soluble Recombinant Human Phosphodiester α-GlcNAcase Approximately $10^8$ 293T cells were plated in a cell factory using Dulbecco's modified eagle's medium (DMEM) containing 10% fetal bovine serum in a humidified atmosphere at 37° C. with 5% CO2. These cells were transfected with approximately 700 g of pKB6 using 2 ml of transfection reagent Fugene-6 (Roche) for the transient expression of soluble human phosphodiester α-GlcNAcase. After three days of culturing the transfected cells, the medium containing soluble, epitope-tagged, human phosphodiester α-GlcNAcase was collected and applied in the presence of 1 mM CaCl2 to a column of monoclonal antibody HPC4 coupled to Ultralink (Pierce). Affinity purified, epitope-tagged, human phosphodiester α-GlcNAcase (approximately 11 mg) was eluted with buffer containing 5 mM EDTA and stored at −20° C. in 50 mM Tris, 150 mM NaCl, 2 mM CaCl2, 50% glycerol, pH 7.2. The enzyme had a specific activity of 500,000 units/mg with [$^3$H]GlcNAc-phosphomannose-α-methyl as a substrate (Kornfeld R, et al., JBC 273:23203–23210).

Example 23

CHO Cells Expressing Recombinant Human Acid α-glucosidase

The human acid α-glucosidase cDNA was obtained from Dr. Frank Martinuk (Martiniuk, F., Mehler, M., Tzall, S., Meredith, G. and Hirschhorn, R. (1990). "Sequence of the cDNA and 5'-flanking region for human acid alpha-glucosidase, detection of an intron in the 5' untranslated leader sequence, definition of 18-bp polymorphisms, and differences with previous cDNA and amino acid sequences." *DNA Cell Biol* 9(2): 85–94) and cloned into the expression vector pEE14.1. This vector was used to transfect CHO-K1 cells using Fugene6 and plated into 96 well plates. Transfectants were selected in 25 μm methionine sulfoxirnine, and clones picked and plated into 96 well plates. The plasmid was amplified by selection with 50 μM, 100 μM, 250μM, and 500 μM methionine sulfoximine. Clones were picked into duplicate 96 well plates and the highest expressing clones selected by assay of the media for acid α-glucosidase activity and the cells for DNA content. The highest expressing clone (Clone 3.49.13) based on acid α-glucosidase activity to DNA content ratio was then expanded into a cell factory. This clone was incubated at 37° C. in 5% $CO_2$ and maintained in Glasgow Minimal Essential Media containing 20 mM TES, pH 7.2, 5% fetal bovine serum.

Example 24

Growth of CHO Cells Expressing Recombinant Human Acid α-glucosidase in the Presence of α-1, 2 Mannosidase Inhibitors CHO cells expressing human acid α-glucosidase were cultured in Glasgow Modified Minimal Essential Media containing 5% Fetal Bovine Serum, 25 μM methionine sulfoximine, 20 mM TES, pH 7.2, and 7.5 mM 1-deoxymannojirimycin-HCl. Alternatively, the cells can be cultured in the above media containing 100 μg/mL 1-deoxymannojirimycin-HCl and 25 μg/mL kifunensine.

Example 25

Isolation of Recombinant Human Acid α-glucosidase

Recombinant human acid α-glucosidase was purified from spent tissue culture media as follows: Media was concentrated 10 fold by tangential ultrafiltration with a 30,000 dalton cutoff membrane and dialyzed into 50 mM sodium phosphate, pH 6.5, and applied to a column of ConA Sepharose (Pharmacia). Following a wash with the same buffer to remove the unbound proteins, acid α-glucosidase was eluted with 1.0 M α-methyl glucoside, pooled, concentrated and dialyzed as before. The acid α-glucosidase was then applied to a column of Sephadex G-200 equilibrated with 50 mM sodium phosphate, pH 6.5 and eluted isocratically with the same buffer.

Example 26

Treatment of Recombinant Human Acid α-glucosidase with GlcNAc-phosphotransferase and Phosphodiester α-GlcNAcase Human acid α-glucosidase at 10 mg/ml was incubated in 50 mm Tris-HCl, pH 6.7, 5 mM $MgCl_2$, 5 mM $MnCl_2$, 2 mM UDP-GlcNAc with GlcNAc-phosphotransferase at 100,000 u/mL at 37° C. for 2 hours. Phosphodiester α-GlcNAcase, 1000 u/mL was then added and the incubation continued for another 2 hours. The acid α-glucosidase was then repurified by chromatography on Q-Sepharose, and step elution with NaCl.

Example 27

Characterization of the Oligosaccharide Structures on Modified Recombinant Human Acid α-glucosidase Recombinant acid α-glucosidase treated or untreated with GlcNAc-phosphotransferase and phosphodiester α-GlcNAcase was digested with N-glycanase (New England Biolabs) or endomannosidase H (New England Biolabs) according to the manufacturer's conditions. The released oligosaccharides were then labeled on the reducing terminus with 2-aminobenzamide and fractionated by HPLC with fluorescent detection according to the manufacturer's instructions (Oxford Glycosystems). Peaks were identified by comparison with standards chromatographed on the same system, and confirmed by digestion with linkage specific glycosidases and/or mass determination by MALDI. The results are shown in Table 1.

TABLE 1

| Enzyme Preparation | M6 | M7 | M8 | M9 | 1P-Gn | 2P-Gn | 1M6P | Complex |
|---|---|---|---|---|---|---|---|---|
| Rh-GAA (Secreted) | 0 | 0 | 0 | 0 | 0 | 0 | 1 | 99 |
| Rh-GAA (dMM/ intracellular) | 23 | 31 | 23 | 6 | 0 | 0 | 17 | 0 |
| Rh-GAA (dMM/ intracellular) Ptase-treated | 6 | 11 | 7 | 2 | 12 | 62 | 0 | 0 |

Referring to Table 1, the data (given in mole percent) show that the Lysosomal enzymes prepared using the GlcNAc-phosphotransferase and phosphodiester α-GlcNAcase of the present invention are highly phosphorylated The data shows that the present invention produces lysosomal enzymes having about 5–10 M6P groups per enzyme compared to about 0–2 for untreated enzymes and enzymes known in the art. When compared to naturally occurring or recombinant lysosomal enzymes, the in vitro-modified preparation is very highly phosphorylated. In the most highly phosphorylated lysosomal enzyme known in the art, the α-galactosidase A described by Matsuura, F., Ohta, M., Ioannou, Y. A. and Desnick. R. J. (1998). "Human alpha-galactosidase A: characterization of the N-linked oligosaccharides on the intracellular and secreted glycoforms overexpressed by Chinese hamster ovary cells." *Glycobiology* 8(4): 329–39, 5.2% of the oligosaccharides are bis-phosphorylated. In marked contrast, 62% of the oligosaccharides on the in vitro-phosphorylated acid α-glucosidase, preparation described here contains bis-phosphorylated oligosaccharides. This represents about a 12 fold increase. When the in vitro phosphorylated preparation of rh-GAA shown in Table 1 is compared with GAA secreted from CHO cells by methods known in the art, an even greater increase in phosphorylation is evident, about a 62 fold increase.

Thus, the in vitro-phosphorylated GAA is 12–62 fold more phosphorylated than any other described preparation of natural or recombinant lysosomal enzyme. This difference has a major influence on the rate and extent of internalization (Reuser, A. J., Kroos, M. A., Ponne, N. J., Wolterman, R A., Loonen, M. C., Busch, H. F., Visser, W. J. and Bolhuis, P. A. (1984). "Uptake and stability of human and bovine acid alpha-glucosidase in cultured fibroblasts and skeletal muscle cells from glycogenosis type II patients." *Experimental Cell Research* 155: 178–189).

Example 28

Comparison of Cell Uptake of Recombinant Human Acid α-glucosidase with or without Modification by GlcNAc-phosphotransferase and Phosphodiester α-GlcNAcase Human Pompe disease fibroblasts are obtained from ATCC and cultured in DMEM with 10% fetal bovine serum in 6 well plates and incubated at 37° C. in 5% $CO_2$. Recombinant human acid α-glucosidase with different carbohydrate structures are compared for the rate and extent of internalization. Controls include each preparation incubated with 5 mM mannose 6-phosphate and incubations without added recombinant human acid α-glucosidase. The different preparations to be examined include acid α-glucosidase secreted from CHO cells, acid α-glucosidase secreted from CHO cells in the presence of α1,2-mannosidase inhibitors, acid α-glucosidase secreted from CHO cells in the presence of α1,2-mannosidase inhibitors treated with GlcNAc-phosphotransferase, and acid α-glucosidase secreted from CHO cells in the presence of α1,2-mannosidase inhibitors treated with GlcNAc-phosphotransferase and phosphodiester α-GlcNAcase. Equal amounts of the four different preparations are added to each well and incubated at 37° C. for periods varying from 5 minutes to 4 hours. At the end of each incubation period the cell monolayers are washed with phosphate buffered saline containing 5 mM mannose 6-phosphate and the monolayer solubilized in 1% Triton X-100 and assayed for internalized acid α-glucosidase by enzymatic assay.

Applicant and the assignee acknowledge their responsibility to replace these cultures should they die before the end of the term of a patent issued hereon, 5 years after the last request for a culture, or 30 years, whichever is the longer, and their responsibility to notify the depository of the issuance of such a patent, at which time the deposit will be made irrevocably available to the public. Until that time the deposit will be made available to the Commissioner of Patents under the terms of 37 C.F.R 1.14 and 35 U.S.C. 112.

While the preferred embodiments are shown to illustrate the invention, numerous changes to the materials and methods can be made by those skilled in the art. All such changes are encompassed within the spirit of the invention as defined by the appended claims.

This application claims priority to U.S. Provisional application No. 60/153,831 filed Sep. 14, 1999, and is incorporated herein by reference.

What is claimed is:

1. A method of producing a modified lysosomal hydrolase comprising culturing transformed cells comprising a recombinant polynucleotide encoding a lysosomal hydrolase in the presence of an α1,2-mannosidase inhibitor;

recovering the lysosomal hydrolase from the cultured transformed cells; and contacting the recovered lysosomal hydrolase with an isolated N-acetylglucosamine-1-phosphotransferase to produce a modified lysosomal hydrolase, wherein said N-acetylglucosamine-phosphotransferase comprises SEQ ID NO:1, SEQ ID NO:2, and SEQ ID NO:3.

2. The method of claim 1, further comprising purifying said modified lysosomal hydrolase after said contacting.

3. The method of claim 1, wherein said N-acetylglucosamine-phosphotransferase catalyzes the transfer of N-acetylglucosamine-1-phosphate from UDP-N-Acetylglucosamine to a mannose on the lysosomal hydrolase.

4. The method of claim 1, wherein said N-acetylglucosamine-phosphotransferase comprises amino acids 1–928 of SEQ ID NO:1, amino acids 1–328 of SEQ ID NO:2, and amino acids 25–305 of SEQ ID NO:3.

5. The method of claim 1, wherein said lysosomal hydrolase is selected from the group consisting of α-glucosidase, α-iduronidase, α-galactosidase A, arylsulfatase, N-acetylgalactosamine-6-sulfatase, β-galactosidase, iduronate 2-sulfatase, ceramidase, galactocerebrosidase, B-glucoronidase, Heparan N-sulfatase, N-Acetyl-α-glucosaminidase, Acetyl CoA-α-glucosaminide N-acetyl transferase, N-acetyl-glucosamine-6 sulfatase, Galactose 6-sulfatase, Arylsulfatase A, Arylsulfatase B, Arylsulfatase C, Arylsulfatase A Cerebroside, Ganglioside, Acid β-galactosidase $G_{MI}$ Galglioside, Acid β-galactosidase, Hexosaminidase A, Hexosaminidase B, α-fucosidase, α-N-Acetyl galactosaminidase, Glycoprotein Neuraminidase, Aspartylglucosamine amidase, Acid Lipase, Acid Ceramidase, Lysosomal Sphingomyelinase, Sphingomyelinase, and Glucocerebrosidase β-Glucosidase.

6. The method of claim 1, further comprising contacting said modified lysosomal hydrolase with an isolated N-acetylglucosamine-1-phosphodiester α-N-Acetylglucosamindase, which comprises the amino acid sequence in SEQ ID NO:6.

7. The method of claim 6, wherein said N-acetylglucosamine-1-phosphodiester α-N-Acetylglucosamindase catalyzes the removal of N-acetylglucosamine from said modified lysosomal hydrolase and generates a terminal mannose 6-phosphate on said hydrolase.

8. The method of claim 6, wherein said N-acetylglucosamine-1-phosphodiester α-N-Acetylglucosamindase comprises amino acids 50-515 of SEQ ID NO:6.

9. The method of claim 1, wherein said alpha 1,2-mannosidase inhibitor is selected from the group consisting of deoxymannojirimycin, kifunensine, D-Mannonolactam amidrazone and N-butyl-dexoymannojirimycin.

10. The method of claim 1, wherein the alpha 1,2-mannosidase inhibitor is kifunensine.

11. The method of claim 1, wherein the alpha 1,2-mannosidase inhibitor is deoxymannojirimycin.

12. The method of claim 6, wherein said lysosomal hydrolase is α-glucosidase.

13. A modified lysosomal hydrolase obtained by the method of claim 1.

14. A modified lysosomal hydrolase obtained by the method of claim 2.

15. A modified lysosomal hydrolase obtained by the method of claim 3.

16. A modified lysosomal hydrolase obtained by the method of claim 4.

17. A modified lysosomal hydrolase obtained by the method of claim 5.

18. A modified lysosomal hydrolase obtained by the method of claim 6.

19. A modified lysosomal hydrolase obtained by the method of claim 7.

20. A modified lysosomal hydrolase obtained by the method of claim 8.

21. A modified lysosomal hydrolase obtained by the method of claim 9.

22. A modified lysosomal hydrolase obtained by the method of claim 10.

23. A modified lysosomal hydrolase obtained by the method of claim 11.

24. A modified lysosomal hydrolase obtained by the method of claim 12.

25. A method of modifying a lysosomal hydrolase comprising culturing transformed cells comprising a recombinant polynucleotide encoding a lysosomal hydrolase in the presence of an α1,2-mannosidase inhibitor;

recovering the lysosomal hydrolase from the cultured transformed cells; and contacting said recovered lysosomal hydrolase with an isolated N-acetylglucosamine-1-phosphotransferase to produce a modified lysosomal hydrolase, wherein said N-acetylglucosamine-phosphotransferase comprises an amino acid sequence that is at least 70% identical to SEQ ID NO:1, an amino acid sequence that is at least 70% identical to SEQ ID NO:2, and an amino acid sequence that is at least 70% identical to SEQ ID NO:3, and said N-acetylglucosamine-phosphotransferase catalyzes the transfer of N-acetylglucosamine-1-phosphate from UDP-N-Acetylglucosamine to a mannose on the lysosomal hydrolase.

26. The method of claim 25, further comprising purifying said modified lysosomal hydrolase after said contacting.

27. The method of claim 25, wherein said lysosomal hydrolase is selected from the group consisting of α-glucosidase, α-iduronidase, α-galactosidase A, arylsulfatase, N-acetylgalactosamine-6-sulfatase, β-galactosidase, iduronate 2-sulfatase, ceramidase, galactocerebrosidase, B-glucoronidase, Heparan N-sulfatase, N-Acetyl-α-glucosaminidase, Acetyl CoA-α-glucosaminide N-acetyl transferase, N-acetyl-glucosamine-6 sulfatase, Galactose 6-sulfatase, Arylsulfatase A, Arylsulfatase B, Arylsulfatase C, Arylsulfatase A Cerebroside, Ganglioside, Acid β-galactosidase $G_{MI}$ Galglioside, Acid β-galactosidase, Hexosaminidase A, Hexosaminidase B, α-fucosidase, α-N-Acetyl galactosaminidase, Glycoprotein Neuraminidase, Aspartylgiucosamine amidase, Acid Lipase, Acid Ceramidase, Lysosomal Sphingomyelinase, Sphingomyelinase, and Glucocerebrosidase β-Glucosidase.

28. The method of claim 25, wherein said lysosomal hydrolase is α-glucosidase.

29. The method of claim 25, further comprising contacting said modified lysosomal hydrolase with an isolated N-acetylglucosamine-1-phosphodiester α-N-Acetylglucosamindase which comprises an amino acid sequence that is at least 70% identical to SEQ ID NO:6, and wherein said N-acetylglucosamine-1-phosphodiester α-N-Acetylglucosamindase catalyzes the removal of N-acetylglucosamine from said modified lysosomal hydrolases and generates a terminal mannose 6-phosphate on said hydrolase.

30. The method of claim 29, further comprising purifying said lysosomal hydrolase after contacting with the isolated N-acetylglucosamine-1-phosphodiester α-N-Acetylglucosamindase.

31. The method of claim 25, wherein said alpha 1,2-mannosidase inhibitor is selected from the group consisting of deoxymannojirimycin, kifunensine, D-Mannonolactam amidrazone and N-butyl-dexoymannojirimycin.

32. The method of claim 25, wherein the alpha 1,2-mannosidase inhibitor is kifunensine.

33. The method of claim 25, wherein the alpha 1,2-mannosidase inhibitor is deoxymannojirimycin.

34. A modified lysosomal hydrolase obtained by the method of claim 25.

35. A modified lysosomal hydrolase obtained by the method of claim 26.

36. A modified lysosomal hydrolase obtained by the method of claim 27.

37. A modified lysosomal hydrolase obtained by the method of claim 28.

38. A modified lysosomal hydrolase obtained by the method of claim 29.

39. A modified lysosomal hydrolase obtained by the method of claim 30.

40. A modified lysosomal hydrolase obtained by the method of claim 31.

41. A modified lysosomal hydrolase obtained by the method of claim 32.

42. A modified lysosomal hydrolase obtained by the method of claim 33.

* * * * *